US012807621B2

(12) United States Patent
Ramkissoon et al.

(10) Patent No.: US 12,807,621 B2
(45) Date of Patent: Nov. 24, 2026

(54) COMPOUNDS AND USES THEREOF

(71) Applicant: The University of The West Indies, St. Augustine (TT)

(72) Inventors: Antonio Ramkissoon, Princes Town (IT); Adash Ramsubhag, St. Augustine (TT); Jayaraj Jayaraman, St. Augustine (TT)

(73) Assignee: The University of The West Indies, St. Augustine (TT)

( * ) Notice: Subject to any disclaimer, the term of this patent is extended or adjusted under 35 U.S.C. 154(b) by 630 days.

(21) Appl. No.: 18/138,452

(22) Filed: Apr. 24, 2023

(65) Prior Publication Data

US 2023/0382926 A1 Nov. 30, 2023

Related U.S. Application Data

(60) Provisional application No. 63/334,581, filed on Apr. 25, 2022.

(51) Int. Cl.
*C07D 519/00* (2006.01)
*A61K 45/06* (2006.01)
*A61P 31/04* (2006.01)

(52) U.S. Cl.
CPC ............ *C07D 519/00* (2013.01); *A61K 45/06* (2013.01); *A61P 31/04* (2018.01)

(58) Field of Classification Search
CPC ........ C07D 519/00; A61P 31/04; A61K 45/06
See application file for complete search history.

(56) References Cited

U.S. PATENT DOCUMENTS

| | | | |
|---|---|---|---|
| 8,580,843 B2 | 11/2013 | Tjalkens et al. | |
| 2010/0087504 A1 | 4/2010 | Tjalkens | |
| 2016/0037773 A1 | 2/2016 | Qian et al. | |

FOREIGN PATENT DOCUMENTS

| | | | |
|---|---|---|---|
| WO | WO-99/00381 A1 | 1/1999 | |
| WO | WO-2017161374 A1 * | 9/2017 | ......... A61K 31/5377 |
| WO | WO-2018/107201 A1 | 6/2018 | |
| WO | WO-2020104842 A1 * | 5/2020 | ............. A61K 45/06 |

OTHER PUBLICATIONS

Thornber, Chemical Society Reviews, 4, 1979 (Year: 1979).*
Zhong, Org Letters, 2022, 24, 1022-1026 (Year: 2022).*
STN Registry No. 1522361-97-2 (Year: 2014).*
STN Registry No. 1522362-10-2 (Year: 2014).*
STN Registry No. 1522362-14-6 (Year: 2014).*
STN Registry No. 1522362-20-4 (Year: 2014).*
STN Registry No. 1522362-25-9 (Year: 2014).*
STN Registry No. 23709-48 (Year: 1984).*
STN Registry No. 669771-73-7 (Year: 2004).*
Zhong, Organic Letters, vol. 24, Issue 4, Jan. 20, 2022 (Year: 2022).*
"Wauford, "Hemolysis assay." Portocols.io. Sep. 28, 2016, accessed Feb. 2, 2019. 2 pages (https://www.protocols.io/view/hemolysis-assay-fxkbpkw)."
Andrews, "Determination of minimum inhibitory concentrations," Journal of Antimicrobial Chemotherapy, Jul. 2001, vol. 48, pp. 5-16.
Berge et al., "Pharmaceutical Salts," Journal of Pharmaceutical Sciences, Jan. 1977, vol. 66, No. 1; pp. 1-19.
Buerge et al., "Handling and Restraint" Chapter 31 in The Laboratory Mouse, Academic Press, Elsevier, Nov. 11, 2004, pp. 517-526.
CLSI document M100-S24, "Performance Standards for Antimicrobial Susceptibility Testing; Twenty-Fourth Informational Supplement"Clinical and Laboratory Standards Institute (CLSI), Wayne, Pa: CLSI; Jan. 2014, vol. 34, No. 1. 230 pages.
Deb et al. "An Efficient and Clean Synthesis of Bis(indolyl)methanes in a Protic Solvent at Room Temperature," Tetrahedron Letters, Feb. 27, 2006, vol. 47(9), pp. 1441-1443.
Dong et al., "Small molecule mimics of DFTamP1, a database designed anti-Staphylococcal peptide," Bioorganic & Medicinal Chemistry (2017), available online Nov. 30, 2016, vol. 25, pp. 864-869.
Extended European Search Report mailed Jun. 27, 2022, in the European patent application No. 19887383.8. 13 pages.
Herold et al, "Ciprofloxacin induces apoptosis and inhibits proliferation of human colorectal carcinoma cells," British Journal of Cancer, Feb. 2002, vol. 86(3), pp. 443-448.
Hirashita, "Condensation of indoles and aldehydes in subcritical water without the addition of catalysts." Bulletin of the Chemical Society of Japan, Sep. 25, 2015, vol. 88(12), pp. 1760-1764.
Imran et al., "Synthesis of novel bisindolylmethane Schiff bases and their antibacterial activity," Molecules, Aug. 6, 2014, vol. 19(8), pp. 11722-11740.

(Continued)

*Primary Examiner* — Andrew D Kosar
*Assistant Examiner* — Phillip Matthew Rzeczycki
(74) *Attorney, Agent, or Firm* — Wilmer Cutler Pickering Hale and Dorr LLP

(57) ABSTRACT

A compound of Formula I

I

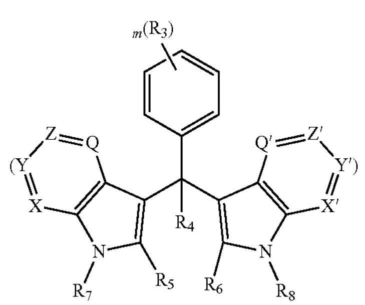

or a pharmaceutically acceptable salt thereof is described. Compositions comprising the compound and methods of using the compound or composition to treat microbial infection are also described.

60 Claims, 8 Drawing Sheets

Specification includes a Sequence Listing.

(56) References Cited

OTHER PUBLICATIONS

International Search Report and Written Opinion mailed Mar. 9, 2020, in the International Application No. PCT/IB19/01221. 14 pages.

Jassim and Al-Ibadi, "Ampicillin inhibition effect on HCT116 cell line" ResarchGate, Mar. 25, 2017. 7 pages. Retrieved from (https://www.researchgate.net/publication/315619261_Ampicillin_inhibition_effect_on_HCT116_cell_line).

Khodaverdian et al., "Discovery of antivirulence agents against methicillin-resistant *Staphylococcus aureus*," Antimicrobial Agents and Chemotherapy, Aug. 2013, vol. 57(8), pp. 3645-3652.

Mandal et al., "Novel boronic acid derivatives of bis(indolyl) methane as anti-MRSA agents," Bioorganic & Medicinal Chemistry Letters, available online Mar. 25, 2017, vol. 27, pp. 2135-2138.

Morrison et al., "The staphylococcal accessory regulator, SarA, is an RNA-binding protein that modulates the mRNA turnover properties of late-exponential and stationary phase *Staphylococcus aureus* cells," Frontiers in Cellular and Infection Microbiology, Mar. 8, 2012, vol. 2(26), pp. 1-11.

Multhoff et al., "Chronic inflammation in cancer development," Frontiers in Immunology, Jan. 12, 2012, vol. 2(98), pp. 1-17.

Nair et al., "Marine Bacteria, XLVII—Psychrotolerant Bacteria from Extreme Antarctic Habitats as Producers of Rare Bis- and Trisindole Alkaloids," Planta Medica, Jun. 2016, vol. 82(6). 9 pages.

O'Toole, "Microtiter Dish Biofilm Formation Assay," Journal of Visualized Experiments, Jan. 30, 2011, 47(2437), pp. 1-2.

Sarva et al., "Synthesis, antibacterial and anti-inflammatory activity of bis(indolyl)methanes," Chinese Chemical Letters (2016), available online Aug. 24, 2015, vol. 27, pp. 16-20.

Sharma et al., "A new class of bactericidal agents against S. aureus, MRSA and VRE derived from bisindolylmethane," Medical Chemistry Research, vol. 23, p. 1643-1653.

Velikova et al., "Walk, the Path towards New Antibacterials with Low Potential for Resistance Development," ACS Medicinal Chemistry Letters, Sep. 18, 2013, vol. 4, pp. 891-894.

Wright, "Antibiotic Adjuvants: Rescuing Antibiotics from Resistance," Trends in Microbiology, Nov. 2016, vol. 24, pp. 862-871.

Zheng et al., "The Essential WalK Histidine Kinase and WalR Regulator Differentially Mediate Autolysis of *Staphylococcus aureus* RN4220," J. Nat. Sci. Jun. 2015, 1(6). Author manuscript, pp. 1-14.

* cited by examiner

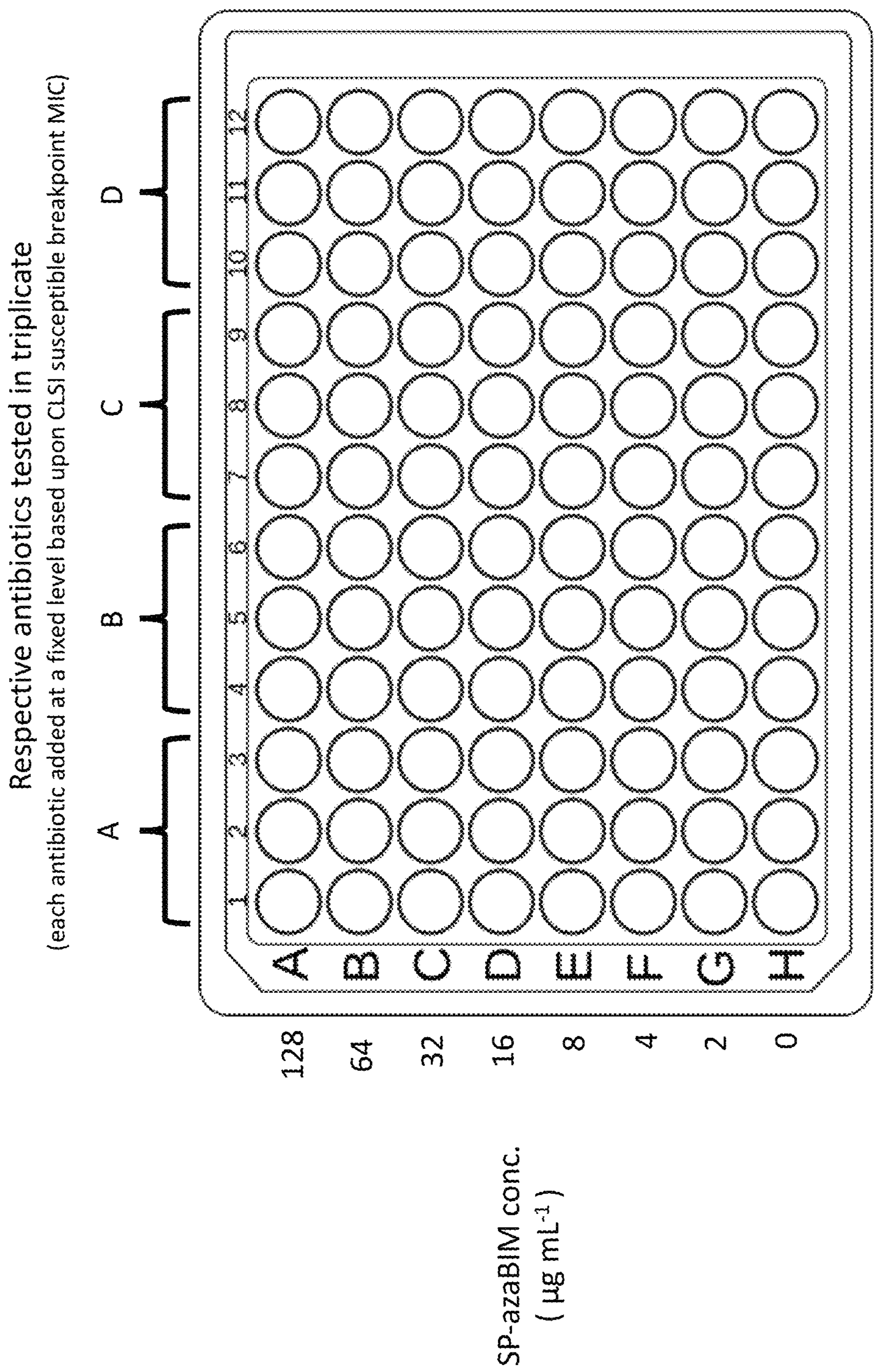
FIG. 1. In vitro assay design for testing SP-azaBIM adjuvant activity

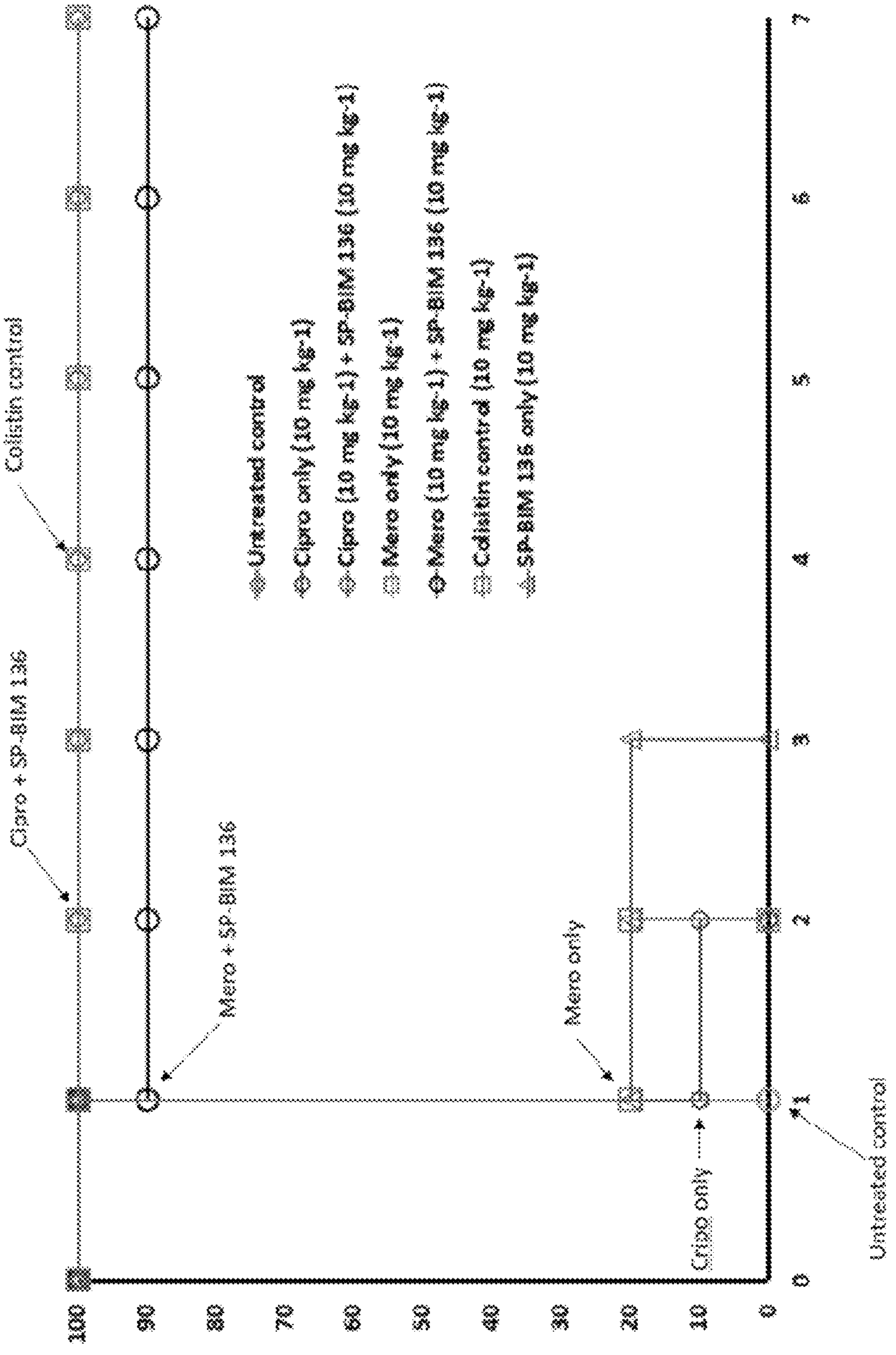
FIG. 3. Lethal peritonitis infection models

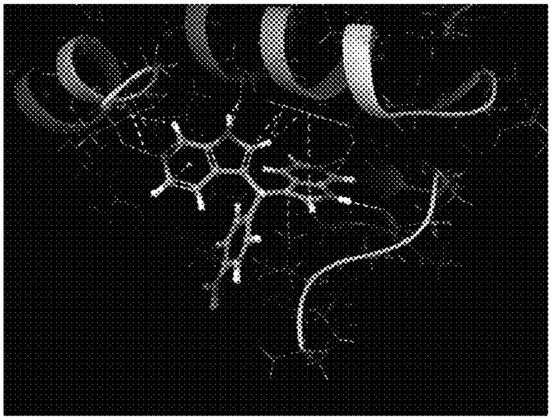
SP-6azaBIM 4
DS= - 9.05
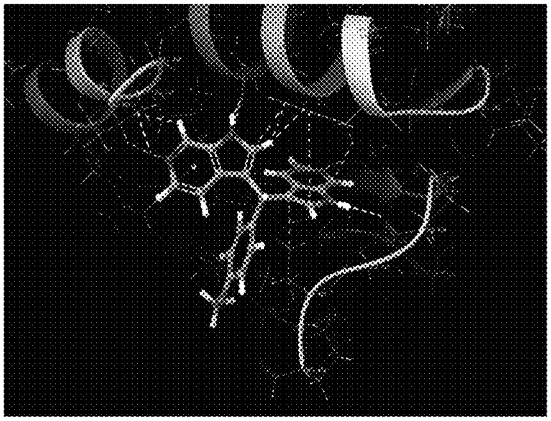
SP-6azaBIM 9
DS= -8.817
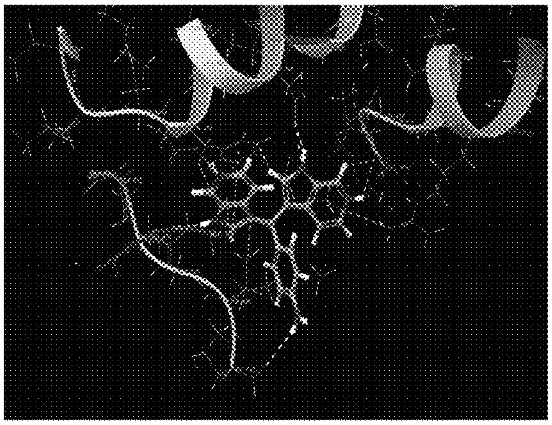
SP-6azaBIM 5
DS= -8.671
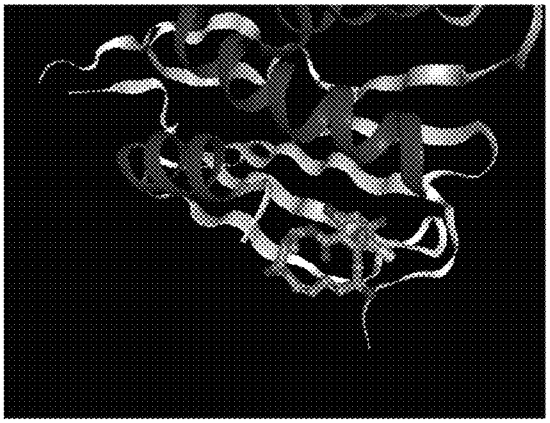
Radicicol
DS= -6.126
FIG. 5

COMPOUNDS AND USES THEREOF

INCORPORATION BY REFERENCE

This application claims the benefit of and priority under 35 U.S.C. § 119(e) to U.S. Ser. No. 63/334,581, filed Apr. 25, 2022, the contents of which is hereby incorporated by reference in its entirety. All patents, patent applications, and publications cited herein are hereby incorporated by reference in their entirety in order to more fully describe the state of the art as known to those skilled therein as of the date of the invention described herein.

SEQUENCE LISTING

The instant application contains a Sequence Listing which has been submitted electronically in XML format and is hereby incorporated by reference in its entirety. Said copy, created on Jun. 9, 2023, is named 2001543 00153US2 SL.xml and is 27,399 bytes in size.

FIELD OF THE INVENTION

This invention generally relates to compounds and pharmaceutical compositions.

BACKGROUND

There is a need to develop new antibiotics but also to develop new strategies to deal with antibiotic resistance. The problem with antibiotic therapy is that bacteria and other microorganisms will, given time, evolve to become resistant. Large pharmaceutical companies have mostly abandoned antibiotic development because it is both expensive and the investment returns are not as large as those of other chronic illnesses.

Antibiotic adjuvants, also termed "resistance breakers" or "antibiotic potentiators," when co-administered with an antibiotic either block the resistance mechanism of the bacteria or enhance the action of the antibiotic drug. The main antibiotic adjuvants currently marketed are the inhibitors of β-lactamase enzymes produced by drug resistant bacteria to break down β-lactam antibiotics, such as the penicillins. However, there are other resistance mechanisms for β-lactams and other classes of antibiotics for which these adjuvants would have no effect. It seems, then, that even though the idea of antibiotic adjuvants is promising, only a very limited number of these compounds have progressed to clinical applications.

Adjuvants offer an advantage in current antimicrobial therapies as they can either enhance the activity of antibiotics or reduce/block resistance of the pathogen. Antibiotic adjuvants have been broadly classed into three categories: 1A, 1B, and 2. Category 1A adjuvants directly inhibit antibiotic resistance by inactivating enzymes, efflux pump systems, or alternate targets while category 1B adjuvants enhance antibiotic activity by circumventing intrinsic resistance mechanisms, including metabolic pathways or physiology other than direct inhibition of specific resistance elements. Category 2 adjuvants do not directly impact bacteria but rather operate on host properties to potentiate an antibiotic's action on bacteria and other microorganisms.

SUMMARY

Described herein are novel antimicrobial agents and compounds. Also described herein are antimicrobial agents that potentiate established antibiotics. One way in which existing antimicrobial agents can become effective against drug resistant pathogens is to develop potentiators that potentiate the antibiotics.

In one aspect, a compound of Formula I or a pharmaceutically acceptable salt thereof is described,

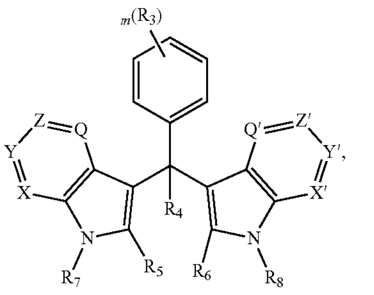

I wherein

X is N or $CR_{1a}$;

Y is N or $CR_{1b}$;

Z is N or $CR_{1c}$;

Q is N or $CR_{1d}$;

X' is N or $CR_{2a}$;

Y' is N or $CR_{2b}$;

Z' is N or $CR_{2c}$;

Q' is N or $CR_{2d}$;

$R_{1a}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{1b}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{1c}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{1d}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$; $R_{2a}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{2b}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{2c}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{2d}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

each occurrence of $R_3$ is independently H, halogen, OH, CN, CHO, $NO_2$, $OCF_3$, ($C_1$ to $C_6$) alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, in which said heterocycle comprises at least one heteroatom selected from the group consisting of nitrogen, oxygen and sulfur and is optionally substituted by alkyl or $OR_a$;

or alternatively two $R_3$ taken together with the ring atoms they are connected to form a 3-7-membered aromatic or heteroaromatic ring that is optionally substituted by 1-3 substituents each independently selected from the group consisting of halogen, OH, CN, ($C_1$ to $C_4$)alkyl, ($C_1$ to $C_4$)haloalkyl, and ($C_1$ to $C_4$)alkoxy;

$R_4$ is H, halogen, OH, CN, $NO_2$, $OCF_3$, ($C_1$ to $C_6$) alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, $(CH_2)_p$($C_3$ to $C_7$)cycloalkyl, $(CH_2)_pOR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_5$ is H, halogen, OH, CN, $OCF_3$, ($C_1$ to $C_6$) alkyl, ($C_1$ to $C_6$)alkoxy, ($C_3$ to $C_7$)cycloalkyl, 3-7-membered heterocycle, $NR_aR_b$, $(CH_2)_p$($C_3$ to $C_7$)cycloalkyl, $(CH_2)_pOR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_6$ is H, halogen, OH, CN, $OCF_3$, ($C_1$ to $C_6$) alkyl, ($C_1$ to $C_6$)alkoxy, ($C_3$ to $C_7$)cycloalkyl, 3-7-membered heterocycle, $NR_aR_b$, $(CH_2)_p$($C_3$ to $C_7$)cycloalkyl, $(CH_2)_pOR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_7$ is H, ($C_1$ to $C_6$) alkyl, ($C_3$ to $C_7$)cycloalkyl, 3-7-membered heterocycle, $COR_a$, $CONR_aR_b$, or $SO_2R_a$; in which said heterocycle comprises at least one heteroatom selected from the group consisting of nitrogen, oxygen and sulfur and is optionally substituted by alkyl or $OR_a$;

$R_8$ is H, ($C_1$ to $C_6$) alkyl, ($C_3$ to $C_7$)cycloalkyl, 3-7-membered heterocycle, $COR_a$, $CONR_aR_b$, or $SO_2R_a$; in which said heterocycle comprises at least one heteroatom selected from the group consisting of nitrogen, oxygen and sulfur and is optionally substituted by alkyl or $OR_a$;

each occurrence of $R_a$ and $R_b$ are each independently H, ($C_1$ to $C_6$)alkyl, ($C_2$ to $C_6$)alkenyl, or ($C_3$ to $C_7$)cycloalkyl;

the alkyl, alkenyl, alkynal, alkoxy, cycloalkyl, aryl, heterocycle, and alkylthio in $R_{1a}$, $R_{1b}$, $R_{1c}$, $R_{1d}$, $R_{2a}$, $R_{2b}$, $R_{2c}$, $R_{2a}$, $R_3$, $R_4$, $R_5$, $R_6$, $R_7$, or $R_8$, where applicable, are optionally substituted by 1-3 substituents each independently selected from the group consisting of halogen, OH, CN, ($C_1$ to $C_4$)alkyl, ($C_1$ to $C_4$)haloalkyl, and ($C_1$ to $C_4$)alkoxy; m is an integer from 0-5;

each occurrence of p is independently an integer from 1-4; and at least one of X, Y, Z, Q, X', Y', Z', and Q' is N.

In any one of the embodiments described herein, at least one of X, Y, Z, and Q is N; and at least one of X', Y', Z', and Q' is N.

In any one of the embodiments described herein, the compound has the structure of Formula Ia, Ib, Ic, Id, le, If, or Ig:

Ia

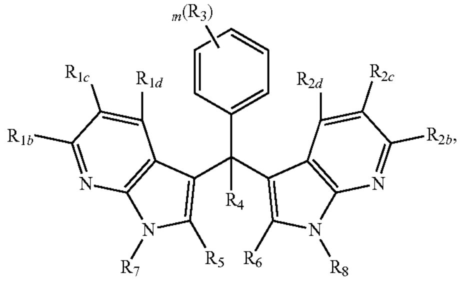

-continued
Ib
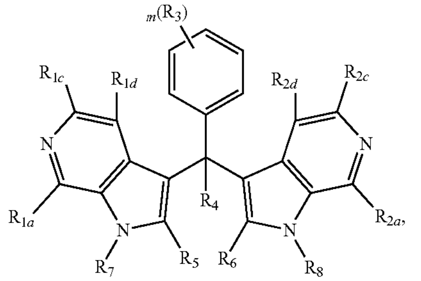
Ic
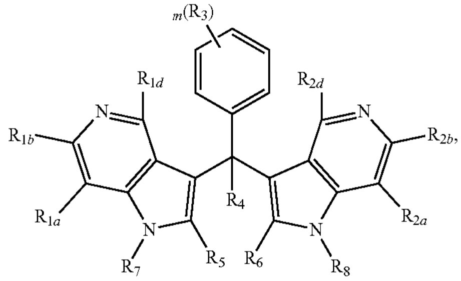
Id
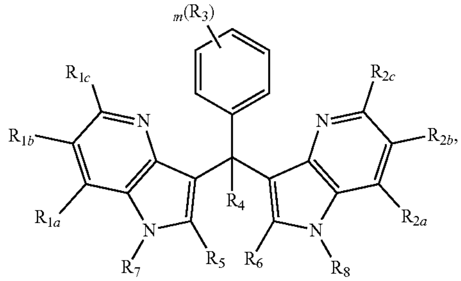
Ie
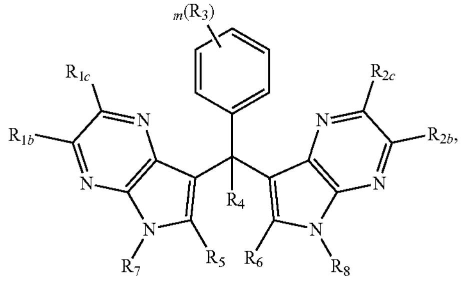
If
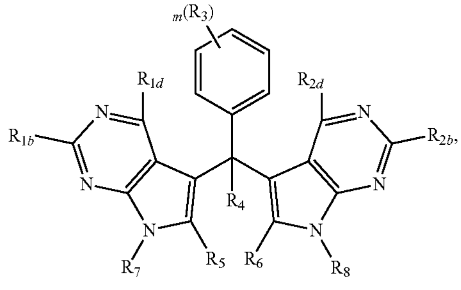
or
-continued
Ig
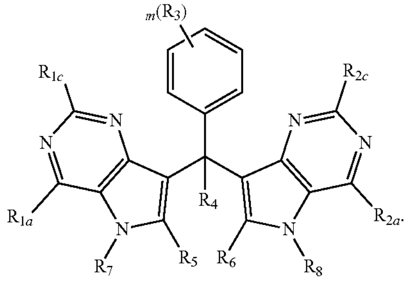
In any one of the embodiments described herein, the compound has the structure of Formula Ih, Ii, Ij, Ik, Im, In, Io, Ip, Iq, or Ir:
Ih
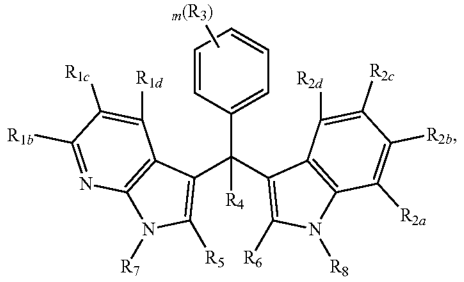
Ii
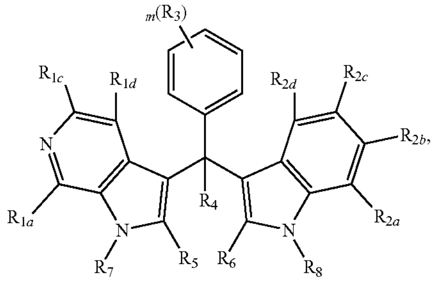
Ij
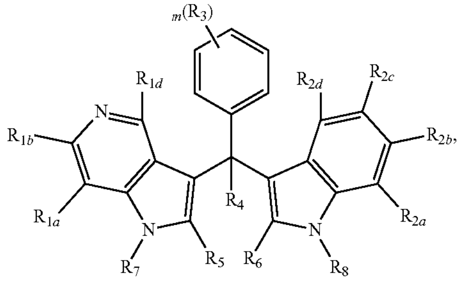
Ik
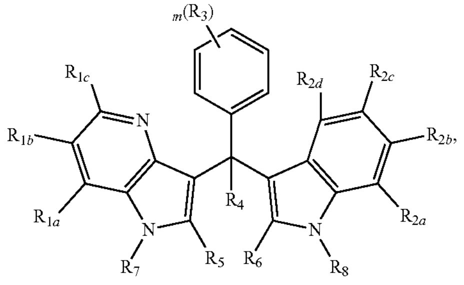

-continued

Im

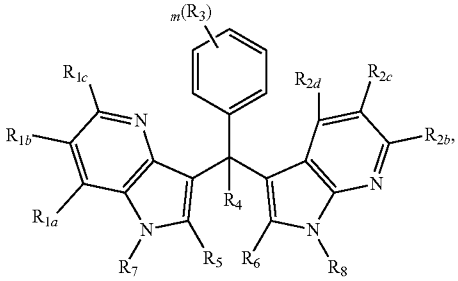

In

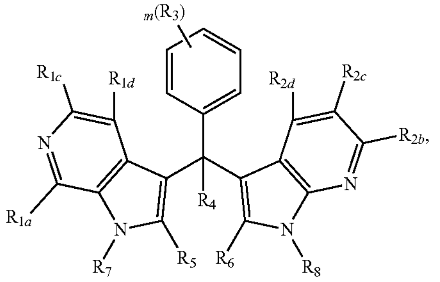

Io

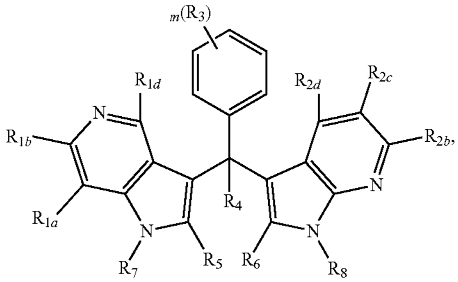

Ip

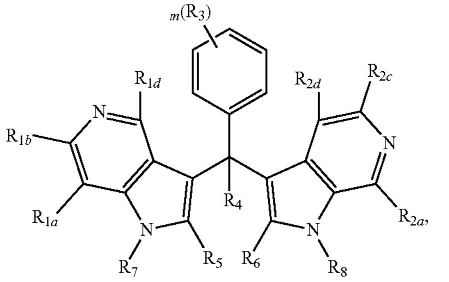

Iq

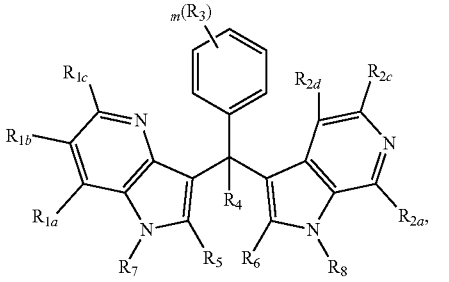

or

-continued

Ir

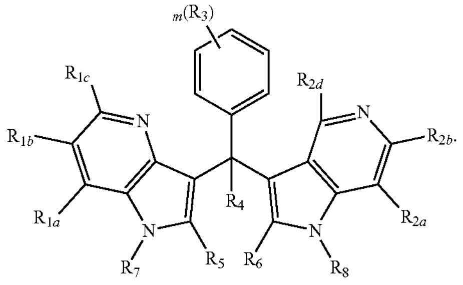

In any one of the embodiments described herein, the compound has the structure of Formula Ia:

Ia

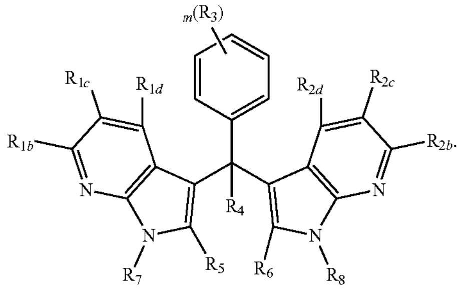

In any one of the embodiments described herein, the compound has the structure of Formula Ib:

Ib

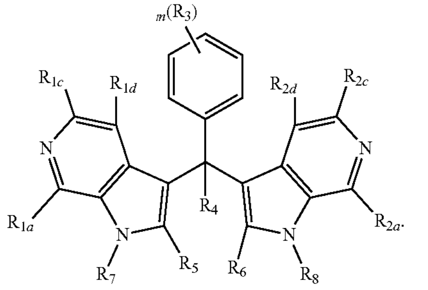

In any one of the embodiments described herein, at least one occurrence of $R_{1a}$ is H, halogen, OH, CN, $OCF_3$, $NR_aR_b$, $NO_2$, $COOR_a$, or $CONR_aR_b$.

In any one of the embodiments described herein, at least one occurrence of $R_{1a}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

In any one of the embodiments described herein, at least one occurrence of $R_{1a}$ is ($C_3$ to $C_7$)cycloalkyl, 3-7-membered heterocycle, or $(CH_2)_p$($C_3$ to $C_7$)cycloalkyl.

In any one of the embodiments described herein, at least one occurrence of $R_{1a}$ is H, OH, $OCH_3$, F, Cl, or Br.

In any one of the embodiments described herein, at least one occurrence of $R_{1b}$ is H, halogen, OH, CN, $OCF_3$, $NR_aR_b$, $NO_2$, $COOR_a$, or $CONR_aR_b$.

In any one of the embodiments described herein, at least one occurrence of $R_{1b}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

In any one of the embodiments described herein, at least one occurrence of $R_{1b}$ is ($C_3$ to $C_7$)cycloalkyl, 3-7-membered heterocycle, or $(CH_2)_p$($C_3$ to $C_7$)cycloalkyl.

In any one of the embodiments described herein, at least one occurrence of $R_{1b}$ is H, OH, $OCH_3$, F, Cl, or Br.

In any one of the embodiments described herein, at least one occurrence of $R_{1c}$ is H, halogen, OH, CN, $OCF_3$, $NR_aR_b$, $NO_2$, $COOR_a$, or $CONR_aR_b$.

In any one of the embodiments described herein, at least one occurrence of $R_{1c}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

In any one of the embodiments described herein, at least one occurrence of $R_{1c}$ is ($C_3$ to $C_7$)cycloalkyl, 3-7-membered heterocycle, or $(CH_2)_p$($C_3$ to $C_7$)cycloalkyl.

In any one of the embodiments described herein, at least one occurrence of $R_{1c}$ is H, OH, $OCH_3$, F, Cl, or Br.

In any one of the embodiments described herein, at least one occurrence of $R_{1d}$ is H, halogen, OH, CN, $OCF_3$, $NR_aR_b$, $NO_2$, $COOR_a$, or $CONR_aR_b$.

In any one of the embodiments described herein, at least one occurrence of $R_{1d}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

In any one of the embodiments described herein, at least one occurrence of $R_{1d}$ is ($C_3$ to $C_7$)cycloalkyl, 3-7-membered heterocycle, or $(CH_2)_p$($C_3$ to $C_7$)cycloalkyl.

In any one of the embodiments described herein, at least one occurrence of $R_{1d}$ is H, OH, $OCH_3$, F, Cl, or Br.

In any one of the embodiments described herein, at least one occurrence of $R_{2a}$ is H, halogen, OH, CN, $OCF_3$, $NR_aR_b$, $NO_2$, $COOR_a$, or $CONR_aR_b$.

In any one of the embodiments described herein, at least one occurrence of $R_{2a}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

In any one of the embodiments described herein, at least one occurrence of $R_{2a}$ is ($C_3$ to $C_7$)cycloalkyl, 3-7-membered heterocycle, or $(CH_2)_p$($C_3$ to $C_7$)cycloalkyl.

In any one of the embodiments described herein, at least one occurrence of $R_{2a}$ is H, OH, $OCH_3$, F, Cl, or Br.

In any one of the embodiments described herein, at least one occurrence of $R_{2b}$ is H, halogen, OH, CN, $OCF_3$, $NR_aR_b$, $NO_2$, $COOR_a$, or $CONR_aR_b$.

In any one of the embodiments described herein, at least one occurrence of $R_{2b}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

In any one of the embodiments described herein, at least one occurrence of $R_{2b}$ is ($C_3$ to $C_7$)cycloalkyl, 3-7-membered heterocycle, or $(CH_2)_p$($C_3$ to $C_7$)cycloalkyl.

In any one of the embodiments described herein, at least one occurrence of $R_{2b}$ is H, OH, $OCH_3$, F, Cl, or Br.

In any one of the embodiments described herein, at least one occurrence of $R_{2c}$ is H, halogen, OH, CN, $OCF_3$, $NR_aR_b$, $NO_2$, $COOR_a$, or $CONR_aR_b$.

In any one of the embodiments described herein, at least one occurrence of $R_{2c}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

In any one of the embodiments described herein, at least one occurrence of $R_{2c}$ is ($C_3$ to $C_7$)cycloalkyl, 3-7-membered heterocycle, or $(CH_2)_p$($C_3$ to $C_7$)cycloalkyl.

In any one of the embodiments described herein, at least one occurrence of $R_{2c}$ is H, OH, $OCH_3$, F, Cl, or Br.

In any one of the embodiments described herein, at least one occurrence of $R_{2d}$ is H, halogen, OH, CN, $OCF_3$, $NR_aR_b$, $NO_2$, $COOR_a$, or $CONR_aR_b$.

In any one of the embodiments described herein, at least one occurrence of $R_{2d}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

In any one of the embodiments described herein, at least one occurrence of $R_{2d}$ is ($C_3$ to $C_7$)cycloalkyl, 3-7-membered heterocycle, or $(CH_2)_p$($C_3$ to $C_7$)cycloalkyl.

In any one of the embodiments described herein, at least one occurrence of $R_{2d}$ is H, OH, $OCH_3$, F, Cl, or Br.

In any one of the embodiments described herein, at least one occurrence of $R_3$ is H, halogen, OH, CN, $OCF_3$, CHO, $NO_2$, $NH_2$, $COOR_a$, or $CONR_aR_b$.

In any one of the embodiments described herein, at least one occurrence of $R_3$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

In any one of the embodiments described herein, at least one occurrence of $R_3$ is ($C_3$ to $C_7$)cycloalkyl, 3-7-membered heterocycle, or $(CH_2)_p$($C_3$ to $C_7$)cycloalkyl.

In any one of the embodiments described herein, at least one occurrence of $R_3$ is H, OH, $OCH_3$, F, Cl, or Br.

In any one of the embodiments described herein, at least one occurrence of $R_3$ is OH.

In any one of the embodiments described herein, at least one occurrence of $R_3$ is Br, F, or $C_1$.

In any one of the embodiments described herein, at least one occurrence of $R_3$ is $NO_2$ or $NH_2$.

In any one of the embodiments described herein, at least one occurrence of $R_3$ is $CH_3$, $CH_2CH_3$, $CH(CH_3)_2$, $CH_2CH_2CH_3$, $OCH_3$, $OCH_2CH_3$, $OCH(CH_3)_2$, $OCH_2CH_2CH_3$, or CHO.

In any one of the embodiments described herein, m is 1.

In any one of the embodiments described herein, m is 2.

In any one of the embodiments described herein, m is 3.

In any one of the embodiments described herein, the structural moiety

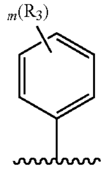

has the structure of

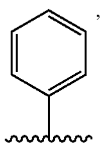, 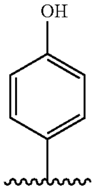, 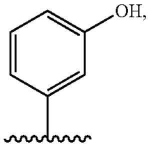

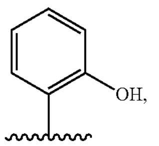 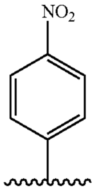, 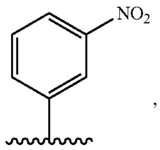,

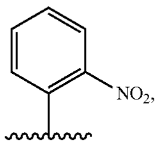 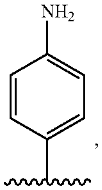, 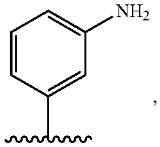,

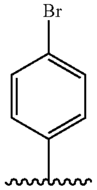, 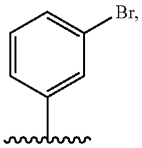 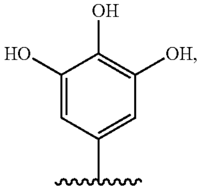

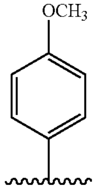, 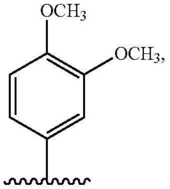 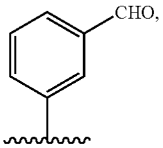

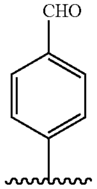, 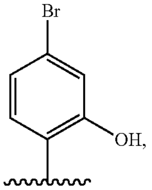 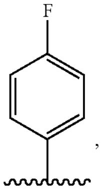, 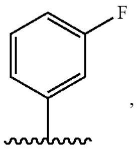,

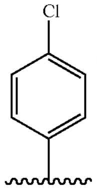, or 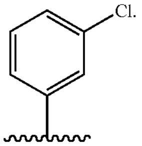

In any one of the embodiments described herein, $R_4$ is H, halogen, OH, CN, $OCF_3$, $NR_aR_b$, ($C_1$ to $C_6$) alkyl, ($C_1$ to $C_6$)alkoxy, $(CH_2)_pOR_a$, $(CH_2)_pSR_a$, or $(CH_2)_pNR_aR_b$.

In any one of the embodiments described herein, $R_4$ is H, Cl, F, Br, OH, $CH_3$, $OCH_3$, $OCF_3$, or $CH_2CH_3$.

In any one of the embodiments described herein, $R_5$ is H, halogen, OH, CN, $OCF_3$, $NR_aR_b$, ($C_1$ to $C_6$) alkyl, ($C_1$ to $C_6$)alkoxy, $(CH_2)_pOR_a$, $(CH_2)_pSR_a$, or $(CH_2)_pNR_aR_b$.

In any one of the embodiments described herein, $R_5$ is H, Cl, F, Br, $CH_3$, $OCH_3$, $OCF_3$, or $CH_2CH_3$.

In any one of the embodiments described herein, $R_6$ is H, halogen, OH, CN, $OCF_3$, $NR_aR_b$, ($C_1$ to $C_6$) alkyl, ($C_1$ to $C_6$)alkoxy, $(CH_2)_pOR_a$, $(CH_2)_pSR_a$, or $(CH_2)_pNR_aR_b$.

In any one of the embodiments described herein, $R_6$ is H, Cl, F, Br, $CH_3$, $OCH_3$, $OCF_3$, or $CH_2CH_3$.

In any one of the embodiments described herein, $R_7$ is H, ($C_1$ to $C_6$) alkyl, ($C_3$ to $C_7$)cycloalkyl, $COR_a$, $CONR_aR_b$, or $SO_2R_a$.

In any one of the embodiments described herein, $R_7$ is H, $CH_3$, $CH_2CH_3$, C(=O)$CH_3$, or C(=O)$NHCH_3$.

In any one of the embodiments described herein, $R_8$ is H, ($C_1$ to $C_6$) alkyl, ($C_3$ to $C_7$)cycloalkyl, $COR_a$, $CONR_aR_b$, or $SO_2R_a$.

In any one of the embodiments described herein, $R_8$ is H, $CH_3$, $CH_2CH_3$, C(=O)$CH_3$, or C(=O)$NHCH_3$.

In any one of the embodiments described herein, at least one occurrence of p is 1.

In any one of the embodiments described herein, at least one occurrence of p is 2 or 3.

In any one of the embodiments described herein, each occurrence of $R_{1a}$ is independently H, halogen, OH, CN, $OCF_3$, ($C_1$ to $C_6$) alkyl, or ($C_1$ to $C_6$)alkoxy; each occurrence of $R_{1b}$ is independently H, halogen, OH, CN, $OCF_3$, ($C_1$ to $C_6$) alkyl, or ($C_1$ to $C_6$)alkoxy; each occurrence of $R_{1c}$ is independently H, halogen, OH, CN, $OCF_3$, ($C_1$ to $C_6$) alkyl, or ($C_1$ to $C_6$)alkoxy; each occurrence of $R_{1d}$ is independently H, halogen, OH, CN, $OCF_3$, ($C_1$ to $C_6$) alkyl, or ($C_1$ to $C_6$)alkoxy; each occurrence of $R_{2a}$ is independently H, halogen, OH, CN, $OCF_3$, ($C_1$ to $C_6$) alkyl, or ($C_1$ to $C_6$)alkoxy; each occurrence of $R_{2b}$ is independently H, halogen, OH, CN, $OCF_3$, ($C_1$ to $C_6$) alkyl, or ($C_1$ to $C_6$)alkoxy; each occurrence of $R_{2c}$ is independently H, halogen, OH, CN, $OCF_3$, ($C_1$ to $C_6$) alkyl, or ($C_1$ to $C_6$)alkoxy; and each occurrence of $R_{2d}$ is independently H, halogen, OH, CN, $OCF_3$, ($C_1$ to $C_6$) alkyl, or ($C_1$ to $C_6$)alkoxy.

In any one of the embodiments described herein, each occurrence of $R_3$ is independently OH, halogen, CN, $NH_2$, $NO_2$, $OCF_3$, ($C_1$ to $C_6$) alkyl, ($C_1$ to $C_6$)alkoxy, or CHO; $R_4$ is H, halogen, OH, CN, $OCF_3$, ($C_1$ to $C_6$) alkyl, or ($C_1$ to $C_6$)alkoxy; $R_5$ is H, halogen, OH, CN, $OCF_3$, ($C_1$ to $C_6$) alkyl, or ($C_1$ to $C_6$)alkoxy; $R_6$ is H, halogen, OH, CN, $OCF_3$, ($C_1$ to $C_6$) alkyl, or ($C_1$ to $C_6$)alkoxy; $R_7$ is H, ($C_1$ to $C_6$) alkyl, $COR_a$, or $CONR_aR_b$; and $R_8$ is H, ($C_1$ to $C_6$) alkyl, $COR_a$, or $CONR_aR_b$.

In any one of the embodiments described herein, the compound is selected from the group consisting of compounds 34-66 as shown in Table A.

In another aspect, a compound of Formula II or a pharmaceutically acceptable salt thereof is described,

II

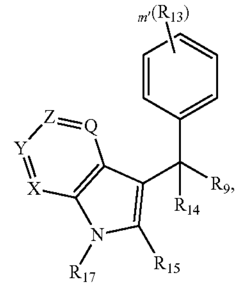

wherein

X is N or $CR_{11a}$;

Y is N or $CR_{11b}$;

Z is N or $CR_{11c}$;

Q is N or $CR_{11d}$;

$R_{11a}$ is independently H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{11b}$ is independently H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{11c}$ is independently H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{11a}$ is independently H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

each occurrence of $R_{13}$ is independently H, halogen, OH, CN, CHO, $NO_2$, $OCF_3$, ($C_1$ to $C_6$) alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, in which said heterocycle comprises at least one heteroatom selected from the group consisting of nitrogen, oxygen and sulfur and is optionally substituted by alkyl or $OR_a$;

or alternatively two $R_{13}$ taken together with the ring atoms they are connected to form a 3-7-membered aromatic or heteroaromatic ring that is optionally substituted by 1-3 substituents each independently selected from the group consisting of halogen, OH, CN, ($C_1$ to $C_4$)alkyl, ($C_1$ to $C_4$)haloalkyl, and ($C_1$ to $C_4$)alkoxy;

$R_{14}$ is independently H, halogen, OH, CN, $NO_2$, $OCF_3$, ($C_1$ to $C_6$) alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, $(CH_2)_p$($C_3$ to $C_7$)cycloalkyl, $(CH_2)_pOR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_{15}$ is H, halogen, OH, CN, $OCF_3$, ($C_1$ to $C_6$) alkyl, ($C_1$ to $C_6$)alkoxy, ($C_3$ to $C_7$)cycloalkyl, 3-7-membered heterocycle, $NR_aR_b$, $(CH_2)_p$($C_3$ to $C_7$)cycloalkyl, $(CH_2)_p OR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_{17}$ is H, ($C_1$ to $C_6$) alkyl, ($C_3$ to $C_7$)cycloalkyl, 3-7-membered heterocycle, $COR_a$, $CONR_aR_b$, or $SO_2R_a$; in which said heterocycle comprises at least one heteroatom selected from the group consisting of nitrogen, oxygen and sulfur and is optionally substituted by alkyl or $OR_a$;

$R_9$ is halogen, OH, CN, $OCF_3$, ($C_1$ to $C_6$) alkyl, ($C_1$ to $C_6$)alkoxy, ($C_3$ to $C_7$)cycloalkyl, 3-7-membered heterocycle, $OR_a$, $NR_aR_b$, $(CH_2)_p$($C_3$ to $C_7$)cycloalkyl, $(CH_2)_p$ $OR_a$, or $(CH_2)_pSR_a$, in which said heterocycle comprises at least one heteroatom selected from the group consisting of nitrogen, oxygen and sulfur and is optionally substituted by alkyl or $OR_a$;

each occurrence of $R_a$ and $R_b$ are each independently H, ($C_1$ to $C_6$)alkyl, ($C_2$ to $C_6$)alkenyl, ($C_3$ to $C_7$)cycloalkyl, heterocycle, aryl, or heteroaryl;

the alkyl, alkenyl, alkynal, alkoxy, cycloalkyl, aryl, heterocycle, and alkylthio in $R_{11a}$, $R_{11b}$, $R_{11c}$, $R_{11d}$, $R_{13}$, $R_{14}$, $R_{15}$, $R_{17}$, or $R_9$ where applicable, are optionally substituted by 1-3 substituents each independently selected from the group consisting of halogen, OH, CN, ($C_1$ to $C_4$)alkyl, ($C_1$ to $C_4$)haloalkyl, and ($C_1$ to $C_4$)alkoxy;

each occurrence of m' is independently an integer from 0-5;

each occurrence of p is independently an integer from 1-4; and at least one of X, Y, Z, and Q is N; and provided the compound is not

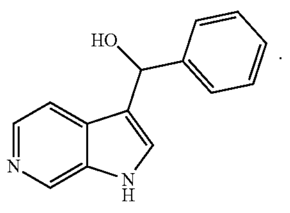 [SMILES: OC(c1ccccc1)c1c[nH]c2cnccc12]

In any one of the embodiments described herein, the compound has the structure of Formula IIa, IIb, IIc, or IId:

IIa

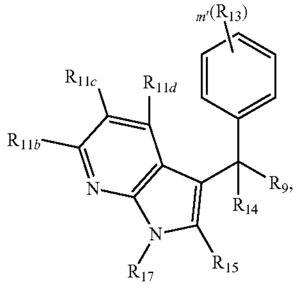

-continued

IIb

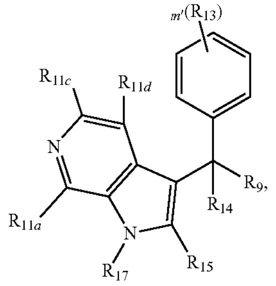

IIc

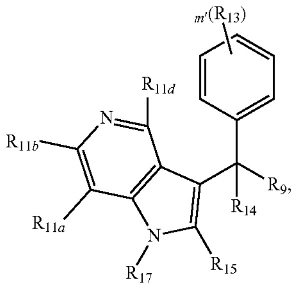 or

IId

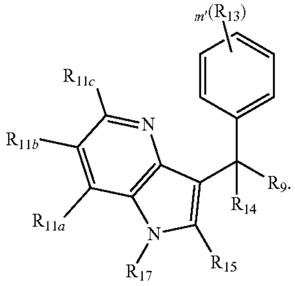

In any one of the embodiments described herein, $R_9$ is $OR_a$ or $NR_aR_b$.

In any one of the embodiments described herein, $R_9$ is selected from the group consisting of OH,

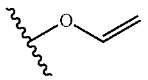, 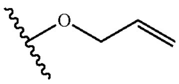, and

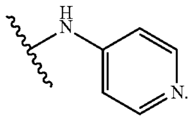

In any one of the embodiments described herein, the compound has the structure of Formula IIe:

IIe

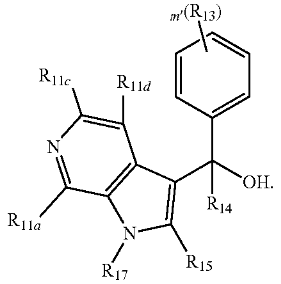

In any one of the embodiments described herein, at least one occurrence of $R_{11a}$ is H, halogen, OH, CN, $OCF_3$, or ($C_1$ to $C_6$)alkoxy.

In any one of the embodiments described herein, at least one occurrence of $R_{11a}$ is H, OH, $OCH_3$, F, Cl, or Br.

In any one of the embodiments described herein, at least one occurrence of $R_{11b}$ is H, halogen, OH, CN, $OCF_3$, or ($C_1$ to $C_6$)alkoxy.

In any one of the embodiments described herein, at least one occurrence of $R_{11b}$ is H, OH, $OCH_3$, F, Cl, or Br.

In any one of the embodiments described herein, at least one occurrence of $R_{11c}$ is H, halogen, OH, CN, $OCF_3$, or ($C_1$ to $C_6$)alkoxy.

In any one of the embodiments described herein, at least one occurrence of $R_{11c}$ is H, OH, $OCH_3$, F, Cl, or Br.

In any one of the embodiments described herein, at least one occurrence of $R_{11d}$ is H, halogen, OH, CN, $OCF_3$, or ($C_1$ to $C_6$)alkoxy.

In any one of the embodiments described herein, at least one occurrence of $R_{11d}$ is H, OH, $OCH_3$, F, Cl, or Br.

In any one of the embodiments described herein, at least one occurrence of $R_{13}$ is H, ($C_1$ to $C_6$)alkyl, ($C_1$ to $C_6$)alkoxy, halogen, OH, CN, $OCF_3$, CHO, $NO_2$, $NH_2$, $COOR_a$, or $CONR_aR_b$.

In any one of the embodiments described herein, at least one occurrence of $R_{13}$ H, OH, $OCH_3$, CHO, F, Cl, or Br.

In any one of the embodiments described herein, at least one occurrence of $R_{13}$ is $NO_2$ or $NH_2$.

In any one of the embodiments described herein, m is 1.

In any one of the embodiments described herein, the structural moiety

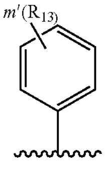

has the structure of

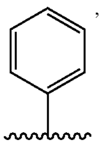, 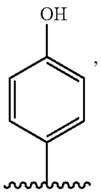, 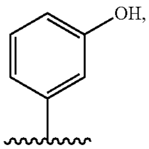

-continued

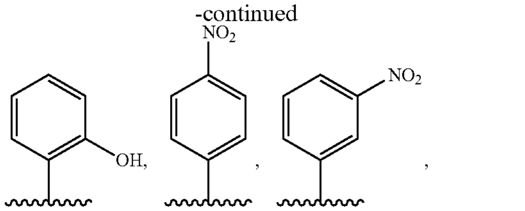

, , ,

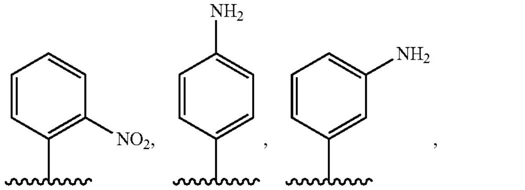

, , ,

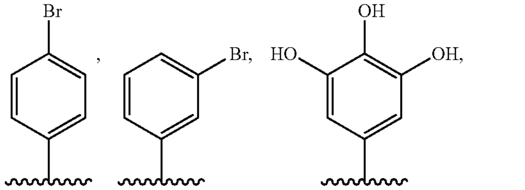

, , ,

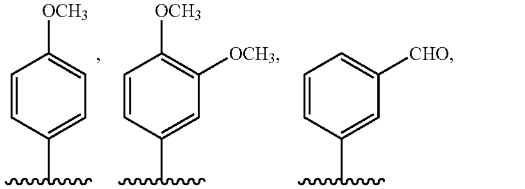

, , ,

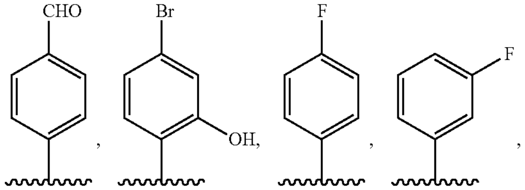

, , , ,

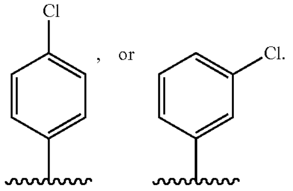

, or .

In any one of the embodiments described herein, $R_{14}$ is H, Cl, F, Br, OH, $CH_3$, $OCH_3$, $OCF_3$, or $CH_2CH_3$.

In any one of the embodiments described herein, $R_{15}$ is H, Cl, F, Br, $CH_3$, $OCH_3$, $OCF_3$, or $CH_2CH_3$.

In any one of the embodiments described herein, $R_{17}$ is H, $CH_3$, $CH_2CH_3$, $C(=O)CH_3$, or $C(=O)NHCH_3$.

In any one of the embodiments described herein, at least one occurrence of p is 1.

In any one of the embodiments described herein, at least one occurrence of p is 2 or 3.

In any one of the embodiments described herein, the compound is selected from the group consisting of compounds 1-33 as shown in Table B.

In another aspect, a pharmaceutical composition is described, comprising at least one compound according to any one of the embodiments described herein or a pharmaceutically acceptable salt thereof.

In any one of the embodiments described herein, the pharmaceutical composition further comprises an antimicrobial agent.

In any one of the embodiments described herein, the antimicrobial agent is an antibacterial agent.

In any one of the embodiments described herein, the antimicrobial agent is an antifungal agent.

In any one of the embodiments described herein, the antimicrobial agent is a macrolide, a folic acid synthesis inhibitor, a fluoroquinolone, an aminoglycoside, a monobactam, a cephalosporin, a glycopeptide, a β-lactam, a carbapenem, or a tetracycline.

In any one of the embodiments described herein, the antimicrobial agent is selected from the group consisting of ampicillin, imipenem, cephalexin, erythromycin, aztreonam, trimethoprim, streptomycin, ciprofloxacin, meropenem, vancomycin, doxycycline, chloramphenicol, and kanamycin.

In any one of the embodiments described herein, the compound is selected from the group consisting of compounds 1-66 as shown in Tables A and B, and the antimicrobial agent is selected from the group consisting of ampicillin, imipenem, cephalexin, erythromycin, streptomycin, ciprofloxacin, meropenem, vancomycin, doxycycline, and kanamycin.

In any one of the embodiments described herein, the pharmaceutical composition further comprises one or more pharmaceutically acceptable excipients.

In yet another aspect, a method of treating, preventing, or reducing the risk of a microbial infection in a subject, comprising administering to the subject a compound according to any one of the embodiments described herein.

In any one of the embodiments described herein, the method further comprises administering to the subject an antimicrobial agent.

In any one of the embodiments described herein, the microbial infection includes an infection caused by one or more bacterial.

In any one of the embodiments described herein, the method comprises treating, preventing, or reducing the risk of biofilms, hemotoxicity, and/or virulence.

In any one of the embodiments described herein, the administration is performed once daily.

In any one of the embodiments described herein, the microbial infection includes an infection caused by one or more clinically antibiotic resistant bacteria.

In any one of the embodiments described herein, the activity of the antimicrobial agent is potentiated by the compound.

In any one of the embodiments described herein, the antimicrobial agent is a macrolide, a folic acid synthesis inhibitor, a fluoroquinolone, an aminoglycoside, a monobactam, a cephalosporin, a glycopeptide, a β-lactam, a carbapenem, or a tetracycline.

In any one of the embodiments described herein, the antimicrobial agent is selected from the group consisting of erythromycin, trimethoprim, ciprofloxacin, meropenem, streptomycin, aztreonam, cefalexin, vancomycin, ampicillin, doxycycline, and kanamycin.

In any one of the embodiments described herein, the antimicrobial agent is ciprofloxacin or meropenem.

In any one of the embodiments described herein, the microbe is Gram-positive bacteria, Gram-negative bacteria, or a mixture thereof.

In any one of the embodiments described herein, the microbe is selected from the group consisting of *Bacillus cereus, Streptococcus pyogenes, Streptococcus pneumoniae, Staphylococcus aureus, Enterococcus faecium, Corynebacterium diphtheriae, Escherichia coli, Salmonella typhimurium, Pseudomonas aeruginosa, Klebsiella pneumoniae, Candida albicans, Klebsiella pneumoniae*, and mixtures thereof.

In any one of the embodiments described herein, the microbe is *Staphylococcus aureus, Enterococcus faecium, Klebsiella pneumoniae* or a mixture thereof.

In any one of the embodiments described herein, the microbe is *Staphylococcus aureus.*

In any one of the embodiments described herein, the microbe is methicillin-resistant *Staphylococcus aureus* (MRSA).

In any one of the embodiments described herein, the microbe is *Klebsiella pneumoniae.*

In any one of the embodiments described herein, the microbe is meropenem- and/or ciprofloxacin-resistant *Klebsiella pneumoniae.*

In any one of the embodiments described herein, the subject is a domestic animal.

In any one of the embodiments described herein, the subject is a mammal.

In any one of the embodiments described herein, the subject is a human.

Any one of the embodiments disclosed herein may be properly combined with any other embodiment disclosed herein. The combination of any one of the embodiments disclosed herein with any other embodiments disclosed herein is expressly contemplated. Specifically, the selection of one or more embodiments for one substituent group can be properly combined with the selection of one or more particular embodiments for any other substituent group. Such combination can be made in any one or more embodiments of the application described herein or any formula described herein.

DESCRIPTION OF THE DRAWINGS

The invention is described with reference to the following figures, which are presented for the purpose of illustration only and are not intended to be limiting. In the drawings:

FIG. 1 depicts a representative design of in vitro assay to test adjuvant activity of compounds according to one or more embodiments described herein.

FIG. 3 depicts the lethal peritonitis infection models, according to one or more embodiments described herein.

FIG. 5 depicts a visual representation of the binding poses of the top 3 binders along with the cognate ligand (radicicol), according to one or more embodiments described herein.

DETAILED DESCRIPTION

Definitions

Figure 2A:
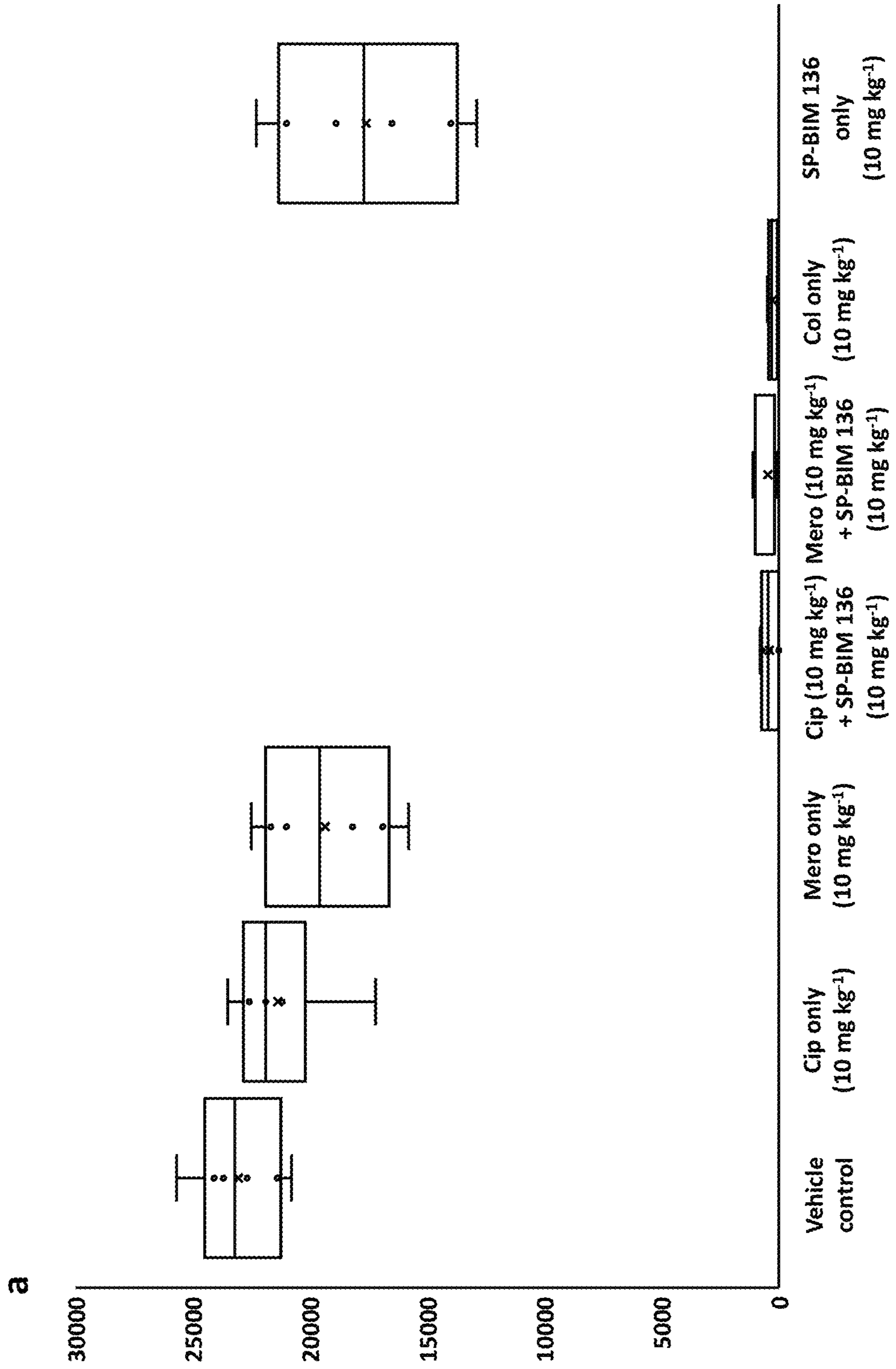
FIG. 2*a* and FIG. 2*b* depict *Klebsiella pneumoniae* load in the liver and spleen of Swiss albino mice treated with mono- and combination therapies of antibiotic and SP-azaBIM 136, according to one or more embodiments described herein.

The following are definitions of terms used in the present specification. The initial definition provided for a group or term herein applies to that group or term throughout the present specification individually or as part of another group, unless otherwise indicated.

The terms "alkyl" and "alk" refer to a straight or branched chain alkane (hydrocarbon) radical containing from 1 to 12 carbon atoms, preferably from 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "($C_1$-$C_4$) alkyl" refers to a straight or branched chain alkane (hydrocarbon) radical containing from 1 to 4 carbon atoms, such as methyl, ethyl, propyl, isopropyl, n-butyl, t-butyl, and isobutyl. The term "($C_1$-$C_6$)alkyl" refers to a straight or branched chain alkane (hydrocarbon) radical containing from 1 to 6 carbon atoms, such as n-hexyl, 2-methylpentyl, 3-methylpentyl, 4-methylpentyl, 2,3-dimethylbutyl, 2,2-dimethylbutyl, in addition to those exemplified for "($C_1$-$C_4$) alkyl." "Substituted alkyl" refers to an alkyl group substituted with one or more substituents, preferably from 1 to 4 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_e$, and Rd is independently hydrogen, alkyl, cycloalkyl, heterocycle, aryl, or said $R_b$ and $R_e$ together with the N to which they are bonded optionally form a heterocycle; and each occurrence of $R_e$ is independently alkyl, cycloalkyl, alkenyl, cycloalkenyl, alkynyl, heterocycle, or aryl. In the aforementioned exemplary substituents, groups such as alkyl, cycloalkyl, alkenyl, alkynyl, cycloalkenyl, heterocycle, and aryl can themselves be optionally substituted.

The term "alkenyl" refers to a straight or branched chain hydrocarbon radical containing from 2 to 12 carbon atoms and at least one carbon-carbon double bond. Examples of such groups include, but are not limited to, ethenyl or allyl. The term "$C_2$-$C_6$ alkenyl" refers to a straight or branched chain hydrocarbon radical containing from 2 to 6 carbon atoms and at least one carbon-carbon double bond, such as ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. "Substituted alkenyl" refers to an alkenyl group substituted with one or more substituents, preferably from 1 to 4 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2 R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_e$, and Rd is independently hydrogen, alkyl, cycloalkyl, heterocycle, aryl, or said $R_b$ and $R_e$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted.

The term "alkynyl" refers to a straight or branched chain hydrocarbon radical containing from 2 to 12 carbon atoms and at least one carbon-carbon triple bond. An example of such groups includes, but is not limited to, ethynyl. The term "$C_2$-$C_6$ alkynyl" refers to a straight or branched chain hydrocarbon radical containing from 2 to 6 carbon atoms and at least one carbon-carbon triple bond, such as ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. "Substituted alkynyl" refers to an alkynyl group substituted with one or more substituents, preferably from 1 to 4 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_e$, and Rd is independently H, alkyl, cycloalkyl, heterocycle, aryl, or said $R_b$ and $R_e$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted.

The term "cycloalkyl" refers to a fully saturated cyclic hydrocarbon group containing from 1 to 4 rings and from 3 to 8 carbons per ring. "$C_3$-$C_7$ cycloalkyl" refers to cyclopropyl, cyclobutyl, cyclopentyl, cyclohexyl, or cycloheptyl. "Substituted cycloalkyl" refers to a cycloalkyl group substituted with one or more substituents, preferably from 1 to 4 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_c$, and Rd is independently H, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle, and aryl substituents can themselves be optionally substituted.

The term "cycloalkenyl" refers to a partially unsaturated cyclic hydrocarbon group containing from 1 to 4 rings and from 3 to 8 carbons per ring. Examples of such groups include, but are not limited to, cyclobutenyl, cyclopentenyl, cyclohexenyl, etc. "Substituted cycloalkenyl" refers to a cycloalkenyl group substituted with one more substituents, preferably from 1 to 4 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_c$, and Rd is independently H, alkyl, cycloalkyl, heterocycle, aryl, or said $R_b$ and $R_e$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle, and aryl substituents can themselves be optionally substituted.

The term "aryl" refers to cyclic, aromatic hydrocarbon groups that have from 1 to 5 aromatic rings, especially monocyclic or bicyclic groups such as phenyl, biphenyl, or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably from 1 to 3 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_c$, and Rd is independently H, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include, but are not limited to, fused cyclic groups, especially fused cycloalkyl, fused cycloalkenyl, fused heterocycle, or fused aryl, where the aforementioned cycloalkyl, cycloalkenyl, heterocycle, and aryl substituents can themselves be optionally substituted.

The terms "heterocycle" and "heterocyclic" refer to fully saturated, or partially or fully unsaturated, including aromatic (i.e., "heteroaryl") cyclic groups (e.g., 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms, and/or sulfur atoms, where the nitrogen and sulfur heteroatoms may optionally be oxidized and the nitrogen heteroatoms may optionally be quaternized. The term "heteroarylium" refers to a heteroaryl group bearing a quaternary nitrogen atom and, thus, a positive charge. The heterocyclic group may be attached to the remainder of the molecule at any heteroatom or carbon atom of the ring or ring system. Exemplary monocyclic heterocyclic groups include, but are not limited to, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl, and the like. Exemplary tricyclic heterocyclic groups include, but are not limited to, carbazolyl, benzidolyl, phenanthrolinyl, acridinyl, phenanthridinyl, xanthenyl, and the like.

"Substituted heterocycle" and "substituted heterocyclic" (such as "substituted heteroaryl") refer to heterocycle or heterocyclic groups substituted with one or more substituents, preferably from 1 to 4 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_c$, and Rd is independently H, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include, but are not limited to, spiro-attached or fused cyclic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle, and aryl substituents can themselves be optionally substituted.

The term "alkylamino" refers to a group having the structure —NHR', where R' is H, alkyl or substituted alkyl, or cycloalkyl or substituted cycloalkyl, as defined herein. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', where R and R' are each independently alkyl or substituted alkyl, cycloalkyl or substituted cycloalkyl, cycloalkenyl or substituted cyclolalkenyl, aryl or substituted aryl, or heterocyclyl or substituted heterocyclyl, as defined herein. R and R' may be the same or different in an dialkylamino moiety. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In some embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

The terms "halogen" or "halo" refer to chlorine, bromine, fluorine or iodine.

Unless otherwise indicated, any heteroatom with unsatisfied valences is assumed to have hydrogen atoms sufficient to satisfy the valences.

The compounds disclosed herein may form salts which are also within the scope of this disclosure. Reference to a compound disclosed herein is understood to include reference to salts thereof, unless otherwise indicated. The term "salt(s)", as employed herein, denotes acidic and/or basic salts formed with inorganic and/or organic acids and bases. In addition, when a compound disclosed herein contains both a basic moiety, such as, but not limited to, a pyridine or imidazole, and an acidic moiety such as, but not limited to, a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of a compound disclosed herein may be formed, for example, by reacting a compound of formula A, A', or B with an amount of acid or base, such as an equivalent amount, in a medium such as one in which the salt precipitates or in an aqueous medium followed by lyophilization.

The compounds disclosed herein which contain a basic moiety, such as, but not limited to, an amine or a pyridine or imidazole ring, may form salts with a variety of organic and inorganic acids. Exemplary acid addition salts include, but are not limited to, acetates (such as those formed with acetic acid or trihaloacetic acid, e.g., trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates, such as tosylates, undecanoates, and the like.

Compounds disclosed herein which contain an acidic moiety, such as, but not limited to, a carboxylic acid, may form salts with a variety of organic and inorganic bases. Exemplary basic salts include, but are not limited to, ammonium salts, alkali metal salts, such as sodium, lithium and potassium salts, alkaline earth metal salts, such as calcium and magnesium salts, salts with organic bases (e.g., organic amines), such as benzathines, dicyclohexylamines, hydrabamines (formed with N,N-bis(dehydroabietyl) ethylenediamine), N-methyl-D-glucamines, N-methyl-D-glycamides, and t-butyl amines, and salts with amino acids such as arginine, lysine, and the like. Basic nitrogen-containing groups may be quaternized with agents such as lower alkyl halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), aralkyl halides (e.g., benzyl and phenethyl bromides), and others.

Prodrugs and solvates of the compounds disclosed herein are also contemplated herein. The term "prodrug" as employed herein denotes a compound that, upon administration to a subject, undergoes chemical conversion by metabolic or chemical processes to yield a compound as disclosed herein, or a salt and/or solvate thereof. Solvates of the compounds disclosed herein include, for example, hydrates.

Compounds disclosed herein, and salts or solvates thereof, may exist in their tautomeric form (for example, as an amide or imino ether). All such tautomeric forms are contemplated herein as part of the present disclosure.

All stereoisomers of the present compounds (for example, those which may exist due to asymmetric carbons on various substituents), including enantiomeric forms and diastereomeric forms, are contemplated within the scope of this disclosure. Individual stereoisomers of the compounds disclosed herein may, for example, be substantially free of other isomers (e.g., as a pure or substantially pure optical isomer having a specified activity), or may be admixed, for example, as racemates or with all other, or other selected, stereoisomers. The chiral centers of the compounds disclosed herein may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives, or separation by chiral column chromatography. The individual optical isomers can be obtained from the racemates by any suitable method, including, without limitation, conventional methods, such as, for example, salt formation with an optically active acid followed by crystallization.

Compounds disclosed herein are, subsequent to their preparation, preferably isolated and purified to obtain a composition containing an amount by weight equal to or greater than 90%, for example, equal to greater than 95%, equal to or greater than 99% pure ("substantially pure" compound of formula A, A', or B which is then used or formulated as described herein). Such "substantially pure" compounds as disclosed herein are also contemplated herein as part of the present disclosure.

All configurational isomers of the compounds disclosed herein are contemplated, either in admixture or in pure or substantially pure form. The definition of compounds disclosed herein embraces both cis (Z) and trans (E) alkene isomers, as well as cis and trans isomers of cyclic hydrocarbon or heterocyclic rings.

Throughout the specifications, groups, and substituents thereof may be chosen to provide stable moieties and compounds.

Definitions of specific functional groups and chemical terms are described in more detail below. For purposes of this disclosure, the chemical elements are identified in accordance with the Periodic Table of the Elements, CAS Version, *Handbook of Chemistry and Physics,* $75^{th}$ Ed., inside cover, and specific functional groups are generally defined as described therein. Additionally, general principles of organic chemistry, as well as specific functional moieties and reactivity, are described in Sorrell T, Organic Chemistry, University Science Books, Sausalito, CA: 1999, the entire contents of which are incorporated herein by reference.

Certain compounds of the present disclosure may exist in particular geometric or stereoisomeric forms. The present disclosure contemplates all such compounds, including cis- and trans-isomers, R- and S-enantiomers and diastereomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure.

Isomeric mixtures containing any of a variety of isomer ratios may be utilized in accordance with the present disclosure. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present disclosure. Those of ordinary skill in the art will readily appreciate that analogous ratios are contemplated for more complex isomer mixtures.

The compounds disclosed herein also include isotopically labeled compounds, which are identical to the compounds disclosed herein, but for the fact that one or more atoms are replaced by an atom having an atomic mass or mass number different from the atomic mass or mass number usually found in nature. Examples of isotopes that can be incorporated into compounds as disclosed herein include isotopes of hydrogen, carbon, nitrogen, oxygen, phosphorous, sulfur, fluorine, and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds disclosed herein, or an enantiomer, diastereomer, tautomer, or pharmaceutically acceptable salt or solvate thereof, which contain the aforementioned isotopes and/or other isotopes of other atoms are within the scope of this disclosure. Certain isotopically labeled compounds of the present disclosure, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds can generally be prepared by carrying out the procedures disclosed in the Schemes and/or in the Examples below, by substituting a readily available isotopically labeled reagent for a non-isotopically labeled reagent.

If, for instance, a particular enantiomer of a compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be appreciated that the compounds, as described herein, may be substituted with any number of substituents or functional moieties. In general, the term "substituted" whether preceded by the term "optionally" or not, and substituents contained in formulas of this disclosure, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. For purposes of this disclosure, heteroatoms such as nitrogen may have hydrogen substituents and/or any permissible substituents of organic compounds described herein which satisfy the valences of the heteroatoms. Furthermore, this disclosure is not intended to be limited in any manner by the permissible substituents of organic compounds. Combinations of substituents and variables envisioned by this disclosure are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "microorganism" or "microbe" as used herein includes, but is not limited to, bacteria, fungi, protozoa, yeast, mold, and mildew. The term "antimicrobial agent" as used herein refers to, but is not limited to, compounds capable of inhibiting, reducing or preventing growth of a microorganism, capable of inhibiting or reducing ability of a microorganism to produce infection in a host, or capable of inhibiting or reducing ability of a microorganism to multiply or remain infective in the environment. The term "antimicrobial agent" also refers to compounds capable of decreasing infectivity or virulence of a microorganism. In some embodiments, antimicrobial agent as used herein includes, but is not limited to, antibiotic agent, antibacterial agent, and antifungal agent.

In some embodiments, the terms "antibacterial agent" or "antibiotic agent" as used herein refers to compounds capable of inhibiting, reducing, or preventing growth of bacteria, capable of inhibiting or reducing ability of bacteria to produce infection in a host, or capable of inhibiting or reducing ability of bacteria to multiply or remain infective in the environment. The term "antibacterial agent" also refers to compounds capable of decreasing infectivity or virulence of bacteria.

In some embodiments, the term "antifungal agent" as used herein refers to compounds capable of inhibiting, reducing, or preventing growth of fungi, capable of inhibiting or reducing ability of fungi to produce infection in a host, or capable of inhibiting or reducing ability of fungi to grow or remain infective in the environment. The term "antifungal agent" also refers to compounds capable of decreasing infectivity of fungi.

In some embodiments, the term "growth" as used herein refers to the growth of microorganisms and includes reproduction or population expansion of the microorganism. The term also includes maintenance of on-going metabolic processes of a microorganism, including processes that keep the microorganism alive.

In some embodiments, the term "synergistic" or "synergy" as used herein refers to the interaction of two or more agents so that their combined effect is greater than their individual effects. In some embodiments, the term "potentiator" refer to a compound that, when co-administered with an antimicrobial agent, results in the overall increase of the anti-microbial activities. In some embodiments, the resulting anti-microbial activities are more potent, or significantly more potent, than the combined anti-microbial activities of the potentiator and the antimicrobial agent when administered separately. In some embodiments, the terms potentiator and adjuvant are used interchangeably.

Compounds

Compounds having the indole core form the base of a wide variety of natural and synthetic molecules with a plethora of biological activities. In one aspect, bis(indolyl) methanes (BIMs) containing one or more heteroatoms (e.g., N) are disclosed. It has been surprisingly found that these heteroatom-containing BIM compounds possess antibacterial, antifungal, anti-HIV, and/or antitumor activities. It has been surprisingly found that these heteroatom-containing BIM compounds potentiate other antibiotic compounds. In some embodiments, the compounds disclosed herein are antimicrobial adjuvants or potentiators.

In one aspect, the present disclosure provides a compound of Formula I or a pharmaceutically acceptable salt thereof,

I

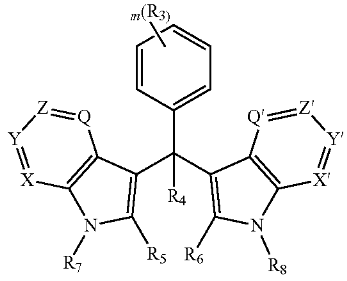

wherein

X is N or $CR_{1a}$;

Y is N or $CR_{1b}$;

Z is N or $CR_{1c}$;

Q is N or $CR_{1d}$;

X' is N or $CR_{2a}$;

Y' is N or $CR_{2b}$;

Z' is N or $CR_{2c}$;

Q' is N or $CR_{2d}$;

$R_{1a}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{1b}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{1c}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{1d}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{2a}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{2b}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{2c}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{2d}$ is H, halogen, OH, CN, $OCF_3$, ($C_1$ to $C_6$)alkyl, halogenate ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

each occurrence of $R_3$ is independently H, halogen, OH, CN, CHO, $NO_2$, $OCF_3$, ($C_1$ to $C_6$) alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, in which said heterocycle comprises at least one heteroatom selected from the group consisting of nitrogen, oxygen and sulfur and is optionally substituted by alkyl or $OR_a$;

or alternatively two $R_3$ taken together with the ring atoms they are connected to form a 3-7-membered aromatic or heteroaromatic ring that is optionally substituted by 1-3 substituents each independently selected from the group consisting of halogen, OH, CN, ($C_1$ to $C_4$)alkyl, ($C_1$ to $C_4$)haloalkyl, and ($C_1$ to $C_4$)alkoxy;

$R_4$ is H, halogen, OH, CN, $NO_2$, $OCF_3$, ($C_1$ to $C_6$) alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, $(CH_2)_p$($C_3$ to $C_7$)cycloalkyl, $(CH_2)_pOR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_5$ is H, halogen, OH, CN, $OCF_3$, ($C_1$ to $C_6$) alkyl, ($C_1$ to $C_6$)alkoxy, ($C_3$ to $C_7$)cycloalkyl, 3-7-membered heterocycle, $NR_aR_b$, $(CH_2)_p$($C_3$ to $C_7$)cycloalkyl, $(CH_2)_pOR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_6$ is H, halogen, OH, CN, $OCF_3$, ($C_1$ to $C_6$) alkyl, ($C_1$ to $C_6$)alkoxy, ($C_3$ to $C_7$)cycloalkyl, 3-7-membered heterocycle, $NR_aR_b$, $(CH_2)_p$($C_3$ to $C_7$)cycloalkyl, $(CH_2)_pOR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_7$ is H, ($C_1$ to $C_6$) alkyl, ($C_3$ to $C_7$)cycloalkyl, 3-7-membered heterocycle, $COR_a$, $CONR_aR_b$, or $SO_2R_a$; in which said heterocycle comprises at least one heteroatom selected from the group consisting of nitrogen, oxygen and sulfur and is optionally substituted by alkyl or $OR_a$;

$R_8$ is H, ($C_1$ to $C_6$) alkyl, ($C_3$ to $C_7$)cycloalkyl, 3-7-membered heterocycle, $COR_a$, $CONR_aR_b$, or $SO_2R_a$; in which said heterocycle comprises at least one heteroatom selected from the group consisting of nitrogen, oxygen and sulfur and is optionally substituted by alkyl or $OR_a$;

each occurrence of $R_a$ and $R_b$ are each independently H, ($C_1$ to $C_6$)alkyl, ($C_2$ to $C_6$)alkenyl, or ($C_3$ to $C_7$)cycloalkyl;

the alkyl, alkenyl, alkynal, alkoxy, cycloalkyl, aryl, heterocycle, and alkylthio in $R_{1a}$, $R_{1b}$, $R_{1c}$, $R_{1d}$, $R_{2a}$, $R_{2b}$, $R_{2c}$, $R_{2a}$, $R_3$, $R_4$, $R_5$, $R_6$, $R_7$, or $R_8$, where applicable, are optionally substituted by 1-3 substituents each independently selected from the group consisting of halogen, OH, CN, ($C_1$ to $C_4$)alkyl, ($C_1$ to $C_4$)haloalkyl, and ($C_1$ to $C_4$)alkoxy;

m is an integer from 0-5;

each occurrence of p is independently an integer from 1-4; and at least one of X, Y, Z, Q, X', Y', Z', and Q' is N.

In some embodiments, at least one of X, Y, Z, and Q is N; and at least one of X', Y', Z', and Q' is N. In some embodiments, one of X, Y, Z, and Q is N; and one of X', Y', Z', and Q' is N. In some embodiments, X is N; Y is $CR_{1b}$; Z is $CR_{1c}$; Q is $CR_{1d}$; X' is N; Y' is $CR_{2b}$; Z' is $CR_{2c}$; and Q' is $CR_{2d}$. In some embodiments, X is $CR_{1a}$; Y is N; Z is $CR_{1c}$; Q is $CR_{1d}$; X' is $CR_{2a}$; Y' is N; Z' is $CR_{2c}$; and Q' is $CR_{2d}$.

In some embodiments, the compound has the structure of Formula Ia, Ib, Ic, Id, Ie, If, or Ig:

Ia

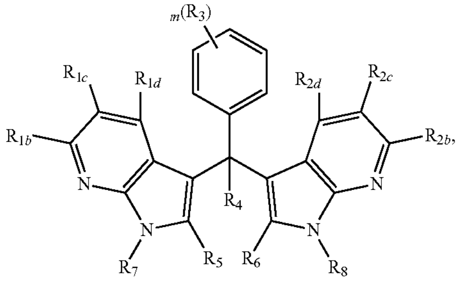

Ib

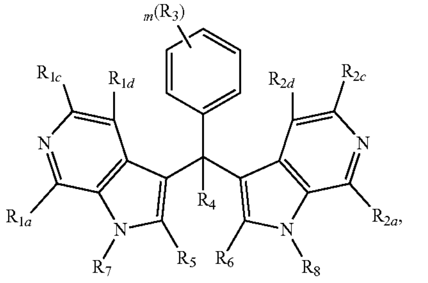

-continued

Ic

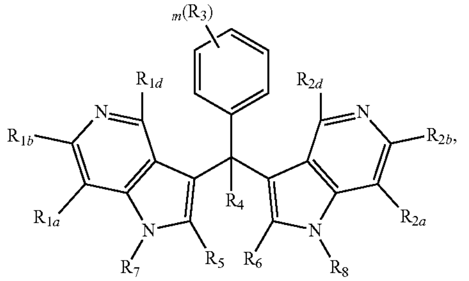

Id

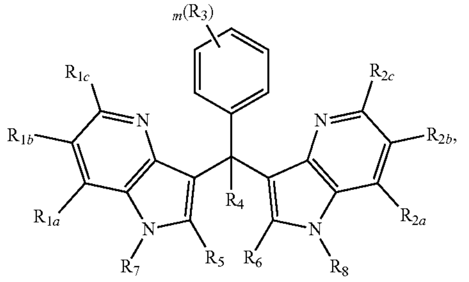

Ie

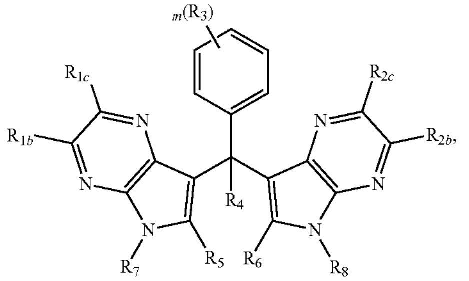

If

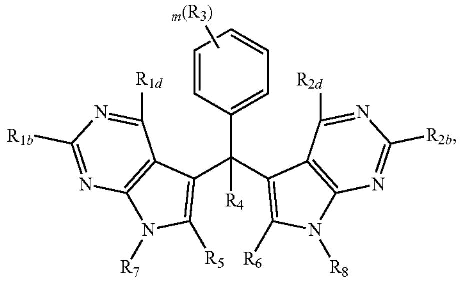

or

Ig

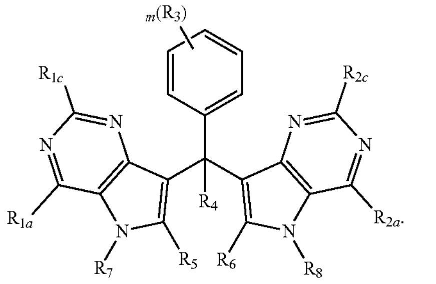

In some embodiments, wherein compound has the structure of Formula Ih, Ii, Ij, Ik, Im, In, Io, Ip, Iq, or Ir:
Ih
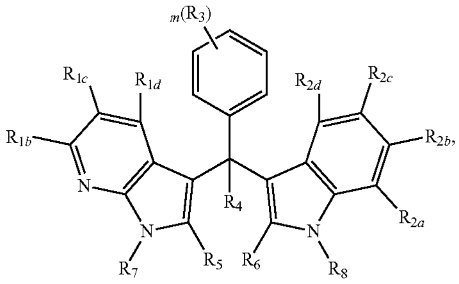
Ii
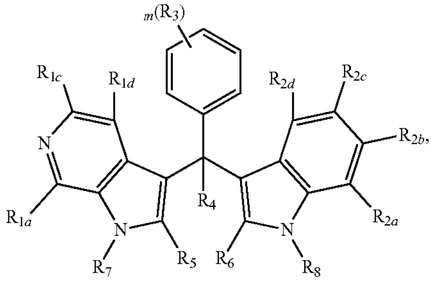
Ij
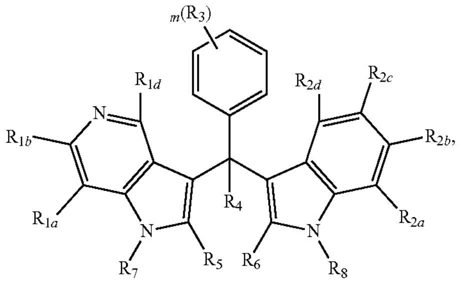
Ik
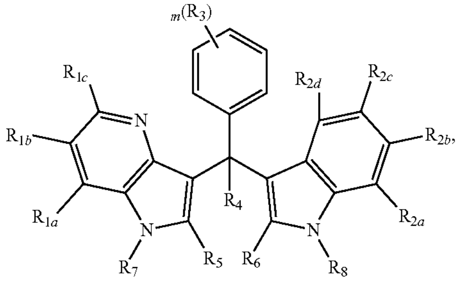
Im
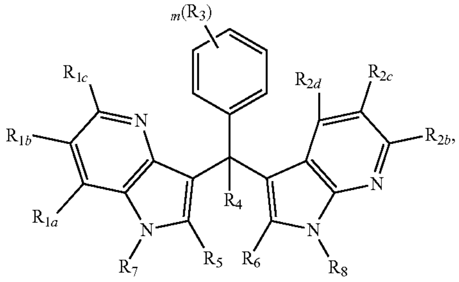
-continued
In
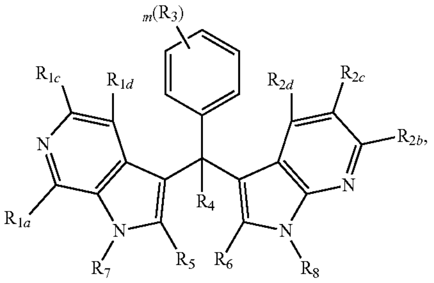
Io
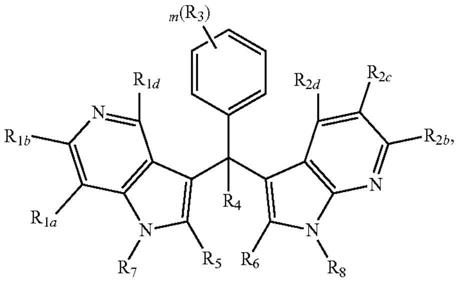
Ip
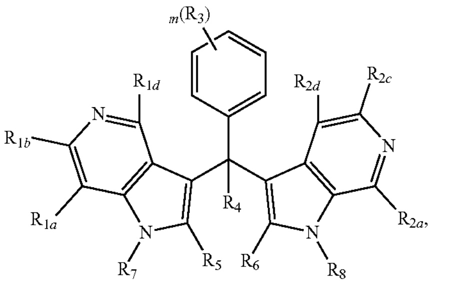
Iq
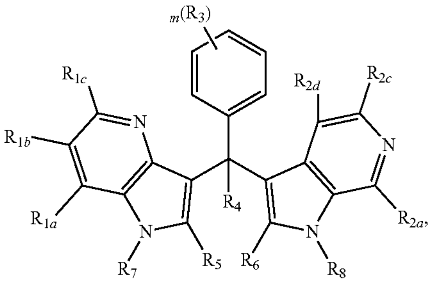
or
Ir
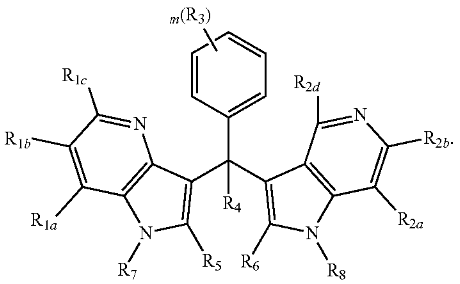

In some embodiments, wherein compound has the structure of Formula Ia:

Ia

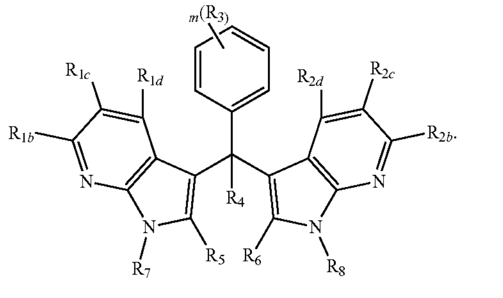

In some embodiments, wherein compound has the structure of Formula Ib:

Ib

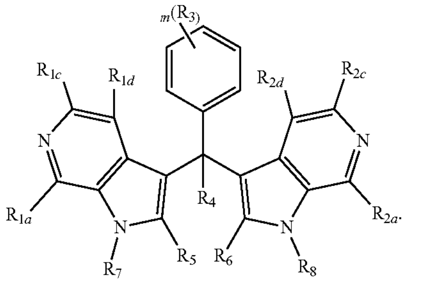

In some embodiments, at least one occurrence of $R_{1a}$ is H, halogen, OH, CN, $OCF_3$, $NR_aR_b$, $NO_2$, $COOR_a$, or $CONR_aR_b$. Non-limiting examples of halogen include F, Cl, Br, and I. In some embodiments, at least one occurrence of $R_{1a}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{1a}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

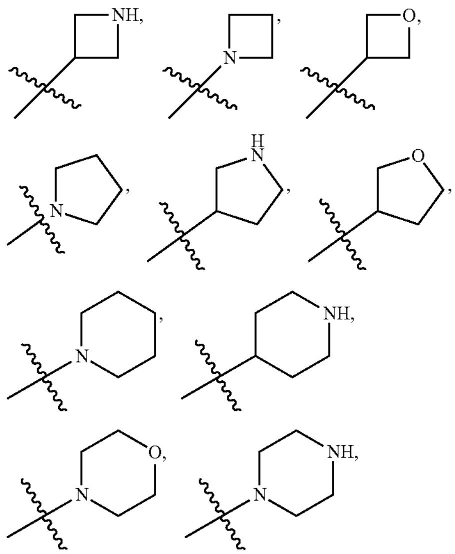

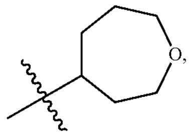 and 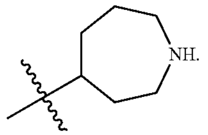

In some embodiments, each occurrence of $R_{1a}$ is independently H, halogen, OH, CN, $OCF_3$, ($C_1$ to $C_6$) alkyl, or ($C_1$ to $C_6$)alkoxy. In some embodiments, at least one occurrence of $R_{1a}$ is H, OH, $OCH_3$, F, Cl, or Br. In some embodiments, each occurrence of $R_{1a}$ is independently H, OH, $OCH_3$, F, Cl, or Br.

In some embodiments, at least one occurrence of $R_{1b}$ is H, halogen, OH, CN, $OCF_3$, $NR_aR_b$, $NO_2$, $COOR_a$, or $CONR_aR_b$. Non-limiting examples of halogen include F, Cl, Br, and I. In some embodiments, at least one occurrence of $R_{1b}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{1b}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

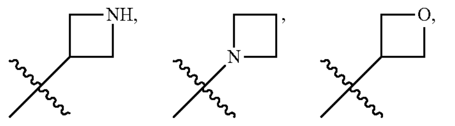,
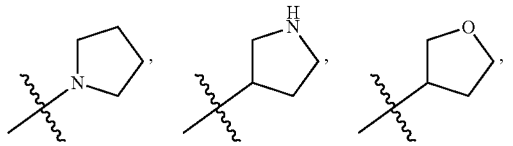,
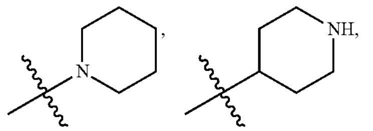,
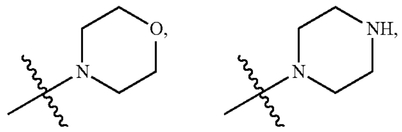,
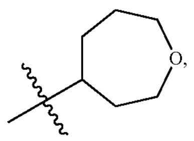 and 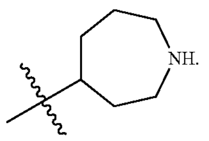.

In some embodiments, each occurrence of $R_{1b}$ is independently H, halogen, OH, CN, $OCF_3$, ($C_1$ to $C_6$) alkyl, or ($C_1$ to $C_6$)alkoxy. In some embodiments, at least one occurrence of $R_{1b}$ is H, OH, $OCH_3$, F, Cl, or Br. In some embodiments, each occurrence of $R_{1b}$ is independently H, OH, $OCH_3$, F, Cl, or Br.

In some embodiments, at least one occurrence of $R_{1c}$ is H, halogen, OH, CN, $OCF_3$, $NR_aR_b$, $NO_2$, $COOR_a$, or $CONR_aR_b$. Non-limiting examples of halogen include F, Cl, Br, and I. In some embodiments, at least one occurrence of $R_{1c}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{1c}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

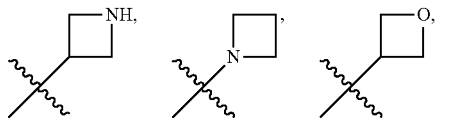,
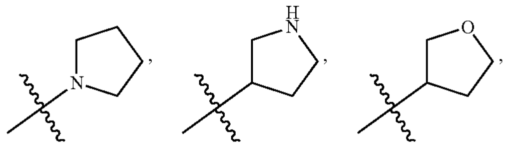,
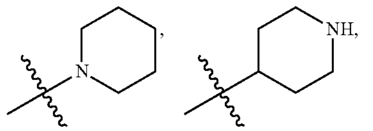,
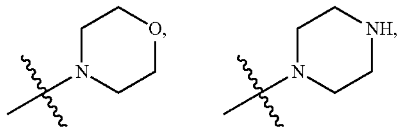,
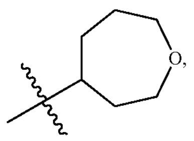 and 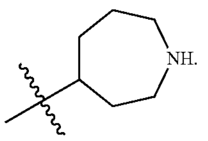.

In some embodiments, each occurrence of $R_{1c}$ is independently H, halogen, OH, CN, $OCF_3$, ($C_1$ to $C_6$) alkyl, or ($C_1$ to $C_6$)alkoxy. In some embodiments, at least one occurrence of $R_{1c}$ is H, OH, $OCH_3$, F, Cl, or Br. In some embodiments, each occurrence of $R_{1c}$ is independently H, OH, $OCH_3$, F, Cl, or Br.

In some embodiments, at least one occurrence of $R_{1d}$ is H, halogen, OH, CN, $OCF_3$, $NR_aR_b$, $NO_2$, $COOR_a$, or $CONR_aR_b$. Non-limiting examples of halogen include F, Cl, Br, and I. In some embodiments, at least one occurrence of $R_{1d}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{1d}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

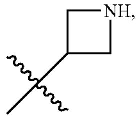, 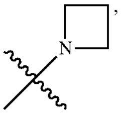, 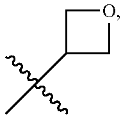, 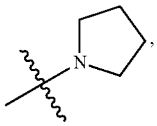, 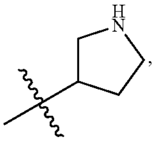, 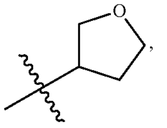, 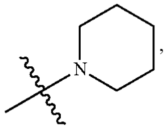, 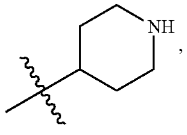, 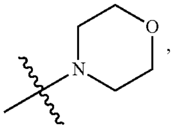, 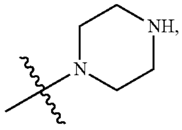, 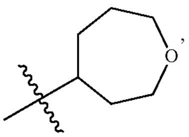, and 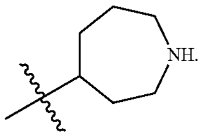.

In some embodiments, each occurrence of $R_{1a}$ is independently H, halogen, OH, CN, $OCF_3$, ($C_1$ to $C_6$) alkyl, or ($C_1$ to $C_6$)alkoxy. In some embodiments, at least one occurrence of $R_{1a}$ is H, OH, $OCH_3$, F, Cl, or Br. In some embodiments, each occurrence of $R_{1a}$ is independently H, OH, $OCH_3$, F, Cl, or Br.

In some embodiments, at least one occurrence of $R_{2a}$ is H, halogen, OH, CN, $OCF_3$, $NR_aR_b$, $NO_2$, $COOR_a$, or $CONR_aR_b$. Non-limiting examples of halogen include F, Cl, Br, and I. In some embodiments, at least one occurrence of $R_{2a}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{2a}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

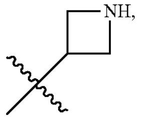, 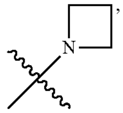, 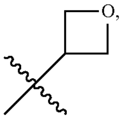, 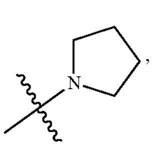, 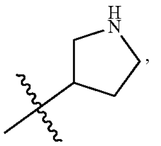, 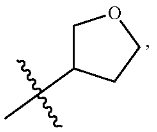, 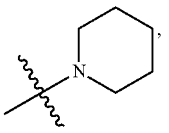, 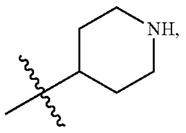, 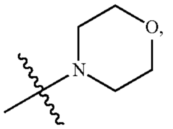, 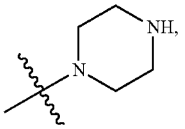, 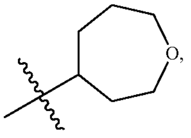, and 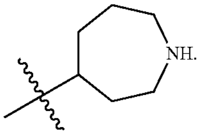.

In some embodiments, each occurrence of $R_{2a}$ is independently H, halogen, OH, CN, $OCF_3$, ($C_1$ to $C_6$) alkyl, or ($C_1$ to $C_6$)alkoxy. In some embodiments, at least one occurrence of $R_{2a}$ is H, OH, $OCH_3$, F, Cl, or Br. In some embodiments, each occurrence of $R_{2a}$ is independently H, OH, $OCH_3$, F, Cl, or Br.

In some embodiments, at least one occurrence of $R_{2b}$ is H, halogen, OH, CN, $OCF_3$, $NR_aR_b$, $NO_2$, $COOR_a$, or $CONR_aR_b$. Non-limiting examples of halogen include F, Cl, Br, and I. In some embodiments, at least one occurrence of $R_{2b}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{2b}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

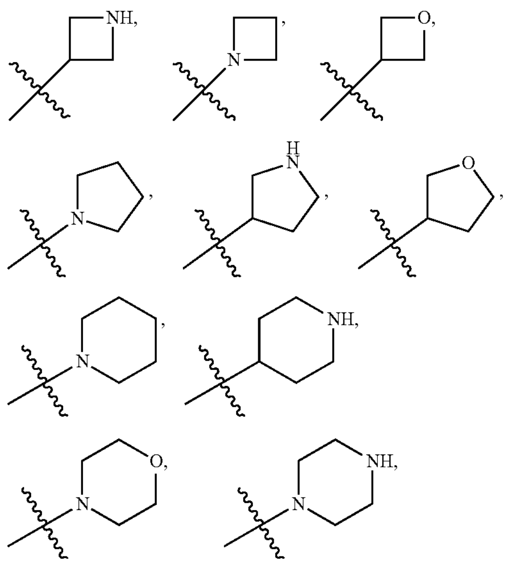

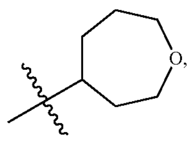

and

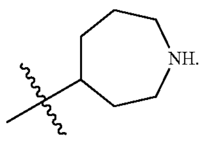

In some embodiments, each occurrence of $R_{2b}$ is independently H, halogen, OH, CN, $OCF_3$, ($C_1$ to $C_6$) alkyl, or ($C_1$ to $C_6$)alkoxy. In some embodiments, at least one occurrence of $R_{2b}$ is H, OH, $OCH_3$, F, Cl, or Br. In some embodiments, each occurrence of $R_{2b}$ is independently H, OH, $OCH_3$, F, Cl, or Br.

In some embodiments, at least one occurrence of $R_{2c}$ is H, halogen, OH, CN, $OCF_3$, $NR_aR_b$, $NO_2$, $COOR_a$, or $CONR_aR_b$. Non-limiting examples of halogen include F, Cl, Br, and I. In some embodiments, at least one occurrence of $R_{2c}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{2c}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

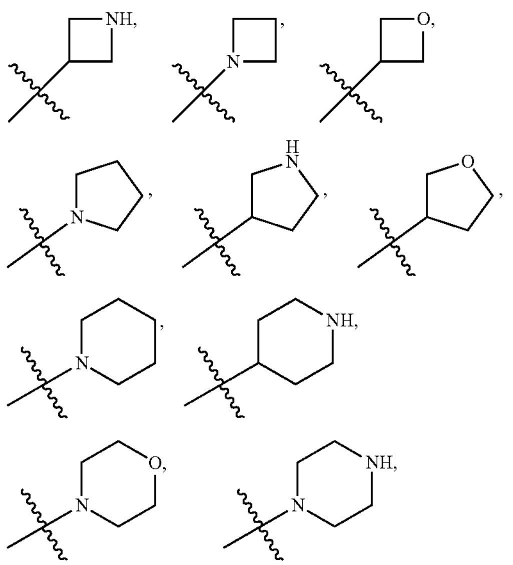

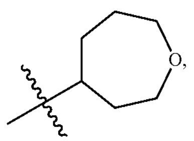

and

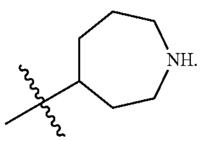

In some embodiments, each occurrence of $R_{2c}$ is independently H, halogen, OH, CN, $OCF_3$, ($C_1$ to $C_6$) alkyl, or ($C_1$ to $C_6$)alkoxy. In some embodiments, at least one occurrence of $R_{2c}$ is H, OH, $OCH_3$, F, Cl, or Br. In some embodiments, each occurrence of $R_{2c}$ is independently H, OH, $OCH_3$, F, Cl, or Br.

In some embodiments, at least one occurrence of $R_{2d}$ is H, halogen, OH, CN, $OCF_3$, $NR_aR_b$, $NO_2$, $COOR_a$, or $CONR_aR_b$. Non-limiting examples of halogen include F, Cl, Br, and I. In some embodiments, at least one occurrence of $R_{2d}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{2d}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

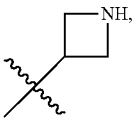, 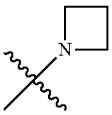, 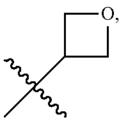, 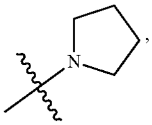, 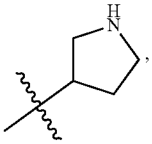, 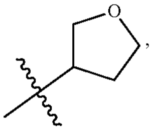, 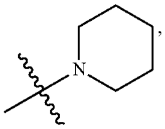, 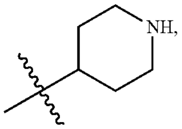, 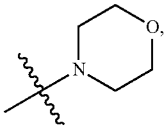, 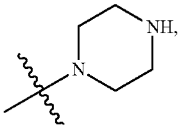, 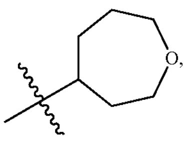 and 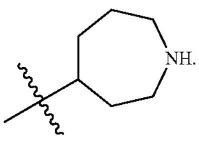.

In some embodiments, each occurrence of $R_{2d}$ is independently H, halogen, OH, CN, $OCF_3$, ($C_1$ to $C_6$) alkyl, or ($C_1$ to $C_6$)alkoxy. In some embodiments, at least one occurrence of $R_{2d}$ is H, OH, $OCH_3$, F, Cl, or Br. In some embodiments, each occurrence of $R_{2d}$ is independently H, OH, $OCH_3$, F, Cl, or Br.

In some embodiments, each occurrence of $R_{1a}$ is independently H, halogen, OH, CN, $OCF_3$, ($C_1$ to $C_6$) alkyl, or ($C_1$ to $C_6$)alkoxy; each occurrence of $R_{1b}$ is independently H, halogen, OH, CN, $OCF_3$, ($C_1$ to $C_6$) alkyl, or ($C_1$ to $C_6$)alkoxy; each occurrence of Ri, is independently H, halogen, OH, CN, $OCF_3$, ($C_1$ to $C_6$) alkyl, or ($C_1$ to $C_6$)alkoxy; each occurrence of $R_{1a}$ is independently H, halogen, OH, CN, $OCF_3$, ($C_1$ to $C_6$) alkyl, or ($C_1$ to $C_6$)alkoxy; each occurrence of $R_{2a}$ is independently H, halogen, OH, CN, $OCF_3$, ($C_1$ to $C_6$) alkyl, or ($C_1$ to $C_6$)alkoxy; each occurrence of $R_{2b}$ is independently H, halogen, OH, CN, $OCF_3$, ($C_1$ to $C_6$) alkyl, or ($C_1$ to $C_6$)alkoxy; each occurrence of $R_{2c}$ is independently H, halogen, OH, CN, $OCF_3$, ($C_1$ to $C_6$) alkyl, or ($C_1$ to $C_6$)alkoxy; and each occurrence of $R_{2d}$ is independently H, halogen, OH, CN, $OCF_3$, ($C_1$ to $C_6$) alkyl, or ($C_1$ to $C_6$)alkoxy.

In some embodiments, at least one occurrence of $R_3$ is H, halogen, OH, CN, $OCF_3$, CHO, $NO_2$, $NH_2$, $COOR_a$, or $CONR_aR_b$. Non-limiting examples of halogen include F, Cl, Br, and I. In some embodiments, at least one occurrence of $R_3$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_3$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

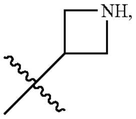, 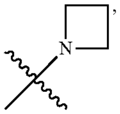, 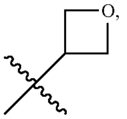, 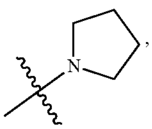, 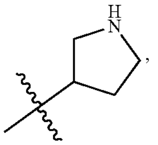, 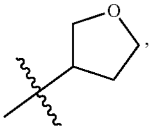, 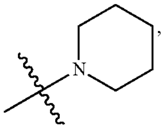, 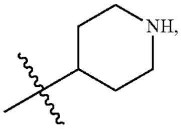, 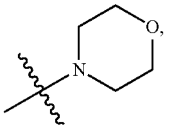, 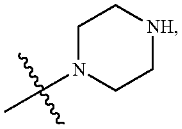 and 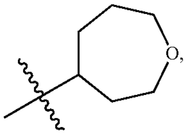.

In some embodiments, each occurrence of $R_3$ is independently OH, halogen, CN, $NH_2$, $NO_2$, $OCF_3$, ($C_1$ to $C_6$) alkyl, ($C_1$ to $C_6$)alkoxy, or CHO. In some embodiments, at least one occurrence of $R_3$ is H, OH, $OCH_3$, F, Cl, or Br. In some embodiments, at least one occurrence of $R_3$ is OH. In some embodiments, at least one occurrence of $R_3$ is Br, F, or $C_1$. In some embodiments, at least one occurrence of $R_3$ is $NO_2$ or $NH_2$. In some embodiments, at least one occurrence of $R_3$ is $CH_3$, $CH_2CH_3$, $CH(CH_3)_2$, $CH_2CH_2CH_3$, $OCH_3$, $OCH_2CH_3$, $OCH(CH_3)_2$, $OCH_2CH_2CH_3$, or CHO. In some embodiments, each occurrence of $R_3$ is independently H, OH, $CH_3$, $OCH_3$, CHO, F, $C_1$, or Br.

In some embodiments, m is 0. In some embodiments, m is 1. In some embodiments, m is 2. In some embodiments, m is 3. In some embodiments, m is 4.

In some embodiments, the structural moiety

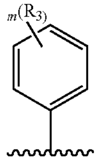

has the structure of

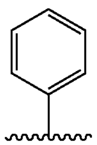, 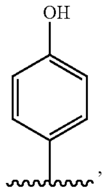, 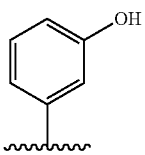, 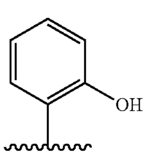,

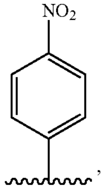, 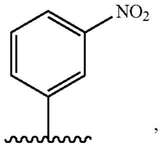, 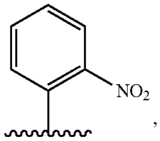,

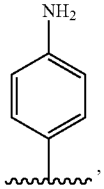, 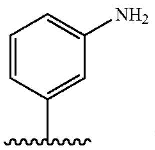, 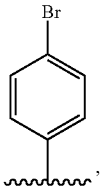, 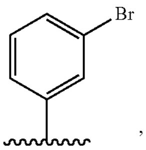,

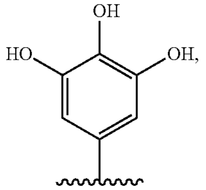 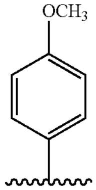, 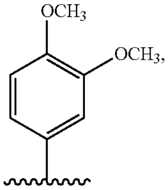

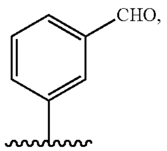 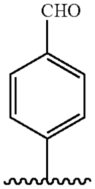, 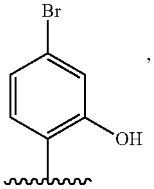,

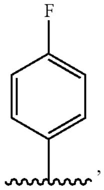, 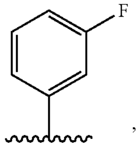, 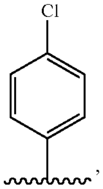, or

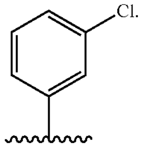

In some embodiments, $R_4$ is H, halogen, OH, CN, $OCF_3$, $NR_aR_b$, ($C_1$ to $C_6$) alkyl, ($C_1$ to $C_6$)alkoxy, $(CH_2)_pOR_a$, $(CH_2)_pSR_a$, or $(CH_2)_pNR_aR_b$. Non-limiting examples of halogen include F, Cl, Br, and I. Non-limiting examples of alkyl include methyl, ethyl, propyl, isopropyl, n-butyl, t-butyl, pentyl, isobutyl pentyl, and hexyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. In some embodiments, $R_4$ is H, OH, halogen, ($C_1$ to $C_6$) alkyl, or ($C_1$ to $C_6$)alkoxy. In some embodiments, $R_4$ is H, Cl, F, Br, OH, $CH_3$, $OCH_3$, $OCF_3$, or $CH_2CH_3$. In some embodiments, $R_4$ is H. In some embodiments, $R_4$ is Cl. In some embodiments, $R_4$ is Br. In some embodiments, $R_4$ is OH.

In some embodiments, $R_5$ is H, halogen, OH, CN, $OCF_3$, $NR_aR_b$, ($C_1$ to $C_6$) alkyl, ($C_1$ to $C_6$)alkoxy, $(CH_2)_pOR_a$, $(CH_2)_pSR_a$, or $(CH_2)_pNR_aR_b$. Non-limiting examples of halogen include F, Cl, Br, and I. Non-limiting examples of alkyl include methyl, ethyl, propyl, isopropyl, n-butyl, t-butyl, pentyl, isobutyl pentyl, and hexyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. In some embodiments, $R_5$ is H, halogen, ($C_1$ to $C_6$) alkyl, or ($C_1$ to $C_6$)alkoxy. In some embodiments, $R_5$ is H, Cl, F, Br, $CH_3$, $OCH_3$, $OCF_3$, or $CH_2CH_3$. In some embodiments, $R_5$ is H. In some embodiments, $R_5$ is Cl. In some embodiments, $R_5$ is Br.

In some embodiments, $R_6$ is H, halogen, OH, CN, $OCF_3$, $NR_aR_b$, ($C_1$ to $C_6$) alkyl, ($C_1$ to $C_6$)alkoxy, $(CH_2)_pOR_a$, $(CH_2)_pSR_a$, or $(CH_2)_pNR_aR_b$. Non-limiting examples of halogen include F, Cl, Br, and I. Non-limiting examples of alkyl include methyl, ethyl, propyl, isopropyl, n-butyl, t-butyl, pentyl, isobutyl pentyl, and hexyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. In some embodiments, $R_6$ is H, halogen, ($C_1$ to $C_6$) alkyl, or ($C_1$ to $C_6$)alkoxy. In some embodiments, $R_6$ is H, Cl, F, Br, $CH_3$, $OCH_3$, $OCF_3$, or $CH_2CH_3$. In some embodiments, $R_6$ is H. In some embodiments, $R_6$ is Cl. In some embodiments, $R_6$ is Br.

In some embodiments, $R_7$ is H, ($C_1$ to $C_6$) alkyl, ($C_3$ to $C_7$)cycloalkyl, $COR_a$, $CONR_aR_b$, or $SO_2R_a$. Non-limiting examples of alkyl include methyl, ethyl, propyl, isopropyl, n-butyl, t-butyl, pentyl, isobutyl pentyl, and hexyl. Non-limiting examples of cycloalkyl include cyclopropyl, cyclobutyl, cyclopentyl, cyclohexyl, and cycloheptyl. In some embodiments, $R_7$ is H, ($C_1$ to $C_6$) alkyl, $COR_a$, or $CONR_aR_b$. In some embodiments, $R_7$ is H, $CH_3$, $CH_2CH_3$, $C(=O)CH_3$, or $C(=O)NHCH_3$. In some embodiments, $R_7$ is H or ($C_1$ to $C_6$) alkyl. In some embodiments, $R_7$ is H. In some embodiments, $R_7$ is $CH_3$.

In some embodiments, $R_8$ is H, ($C_1$ to $C_6$) alkyl, ($C_3$ to $C_7$)cycloalkyl, $COR_a$, $CONR_aR_b$, or $SO_2R_a$. Non-limiting examples of alkyl include methyl, ethyl, propyl, isopropyl, n-butyl, t-butyl, pentyl, isobutyl pentyl, and hexyl. Non-limiting examples of cycloalkyl include cyclopropyl, cyclobutyl, cyclopentyl, cyclohexyl, and cycloheptyl. In some embodiments, $R_8$ is H, ($C_1$ to $C_6$) alkyl, $COR_a$, or $CONR_aR_b$. In some embodiments, $R_8$ is H, $CH_3$, $CH_2CH_3$, $C(=O)CH_3$, or $C(=O)NHCH_3$. In some embodiments, $R_8$ is H or ($C_1$ to $C_6$) alkyl. In some embodiments, $R_8$ is H. In some embodiments, $R_8$ is $CH_3$.

In some embodiments, at least one occurrence of p is 1. In some embodiments, at least one occurrence of p is 2. In some embodiments, at least one occurrence of p is 3. In some embodiments, at least one occurrence of p is 4.

In some embodiments, each occurrence of $R_3$ is independently OH, halogen, CN, $NH_2$, $NO_2$, $OCF_3$, ($C_1$ to $C_6$) alkyl, ($C_1$ to $C_6$)alkoxy, or CHO; $R_4$ is H, halogen, OH, CN, $OCF_3$, ($C_1$ to $C_6$) alkyl, or ($C_1$ to $C_6$)alkoxy; $R_5$ is H, halogen, OH, CN, $OCF_3$, ($C_1$ to $C_6$) alkyl, or ($C_1$ to $C_6$)alkoxy; $R_6$ is H, halogen, OH, CN, $OCF_3$, ($C_1$ to $C_6$) alkyl, or ($C_1$ to $C_6$)alkoxy; $R_7$ is H, ($C_1$ to $C_6$) alkyl, $COR_a$, or $CONR_aR_b$; and $R_8$ is H, ($C_1$ to $C_6$) alkyl, $COR_a$, or $CONR_aR_b$.

In some embodiments, wherein compound has the structure of Formula Ia or Ib

Ia

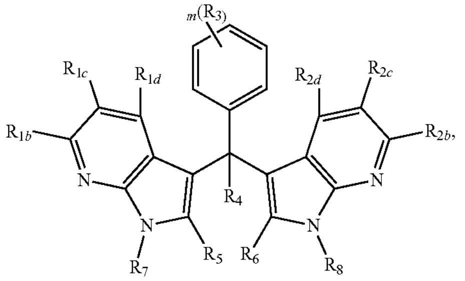

or

Ib

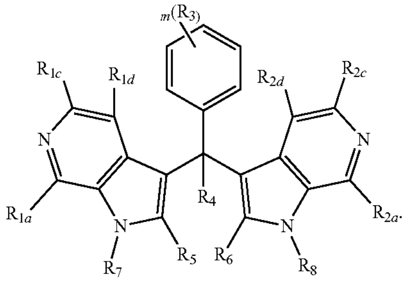

wherein $R_{1a}$ is H, halogen, OH, CN, $OCF_3$, ($C_1$ to $C_6$) alkyl, or ($C_1$ to $C_6$)alkoxy;

$R_{1b}$ is H, halogen, OH, CN, $OCF_3$, ($C_1$ to $C_6$) alkyl, or ($C_1$ to $C_6$)alkoxy;

$R_{1c}$ is H, halogen, OH, CN, $OCF_3$, ($C_1$ to $C_6$) alkyl, or ($C_1$ to $C_6$)alkoxy;

$R_{1d}$ is H, halogen, OH, CN, $OCF_3$, ($C_1$ to $C_6$) alkyl, or ($C_1$ to $C_6$)alkoxy;

$R_{2a}$ is H, halogen, OH, CN, $OCF_3$, ($C_1$ to $C_6$) alkyl, or ($C_1$ to $C_6$)alkoxy;

$R_{2b}$ is H, halogen, OH, CN, $OCF_3$, ($C_1$ to $C_6$) alkyl, or ($C_1$ to $C_6$)alkoxy;

$R_{2c}$ is H, halogen, OH, CN, $OCF_3$, ($C_1$ to $C_6$) alkyl, or ($C_1$ to $C_6$)alkoxy;

$R_{2d}$ is H, halogen, OH, CN, $OCF_3$, ($C_1$ to $C_6$) alkyl, or ($C_1$ to $C_6$)alkoxy;

each occurrence of $R_3$ is independently OH, halogen, CN, $NH_2$, $NO_2$, $OCF_3$, ($C_1$ to $C_6$) alkyl, ($C_1$ to $C_6$)alkoxy, or CHO;

$R_4$ is H, halogen, OH, CN, $OCF_3$, ($C_1$ to $C_6$) alkyl, or ($C_1$ to $C_6$)alkoxy;

$R_5$ is H, halogen, OH, CN, $OCF_3$, ($C_1$ to $C_6$) alkyl, or ($C_1$ to $C_6$)alkoxy;

$R_6$ is H, halogen, OH, CN, $OCF_3$, ($C_1$ to $C_6$) alkyl, or ($C_1$ to $C_6$)alkoxy;

$R_7$ is H, ($C_1$ to $C_6$) alkyl, $COR_a$, or $CONR_aR_b$; and $R_8$ is H, ($C_1$ to $C_6$) alkyl, $COR_a$, or $CONR_aR_b$.

In some embodiments, the present disclosure provides a compound selected from the group consisting of compounds 34-66 as shown in Table A.

TABLE A

| Compound No. | Compound Structure |
|---|---|
| 34 | 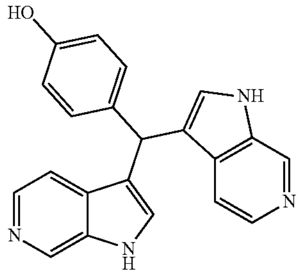 [SMILES: Oc1ccc(C(c2c[nH]c3cnccc23)c2c[nH]c3cnccc23)cc1] |
| 35 | 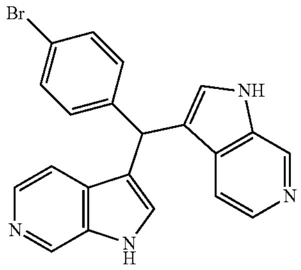 [SMILES: Brc1ccc(C(c2c[nH]c3cnccc23)c2c[nH]c3cnccc23)cc1] |
| 36 | 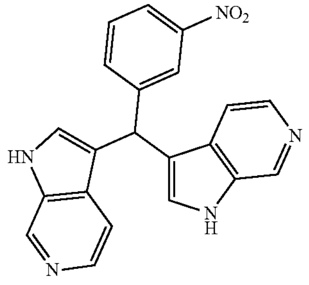 [SMILES: O=[N+]([O-])c1cccc(C(c2c[nH]c3cnccc23)c2c[nH]c3cnccc23)c1] |
| 37 | 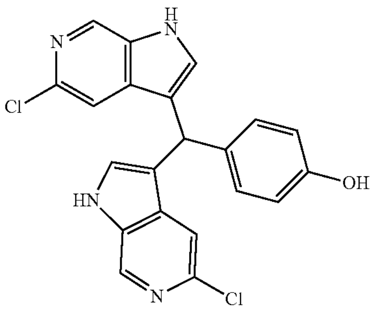 [SMILES: Oc1ccc(C(c2c[nH]c3cnc(Cl)cc23)c2c[nH]c3cnc(Cl)cc23)cc1] |
| 38 | 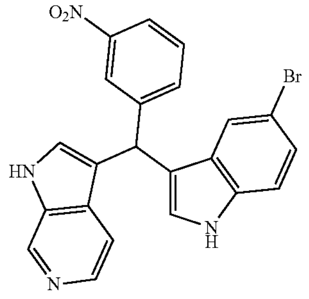 [SMILES: O=[N+]([O-])c1cccc(C(c2c[nH]c3cnccc23)c2c[nH]c3ccc(Br)cc23)c1] |

TABLE A-continued
| Compound No. | Compound Structure |
| --- | --- |
| 39 | 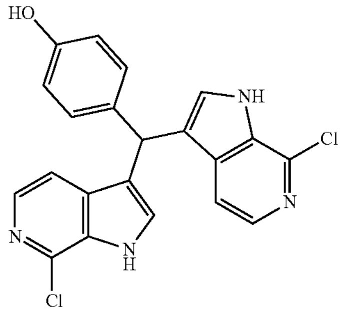 |
| 40 | 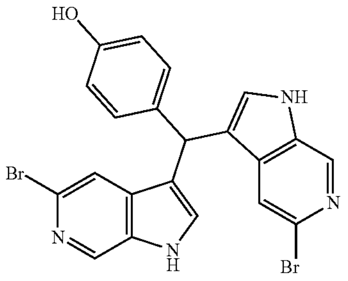 |
| 41 | 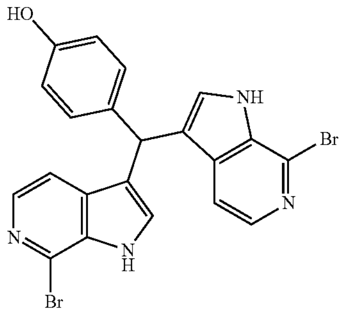 [SMILES: Oc1ccc(C(c2c[nH]c3c(Br)nccc23)c2c[nH]c3c(Br)nccc23)cc1] |
| 42 | 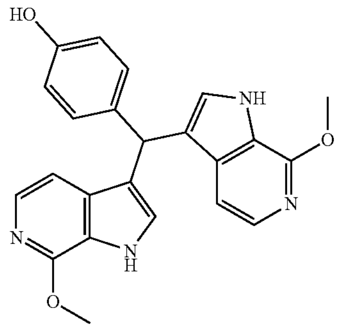 [SMILES: COc1nccc2c(C(c3ccc(O)cc3)c3c[nH]c4c(OC)nccc34)c[nH]c12] |
| 43 | 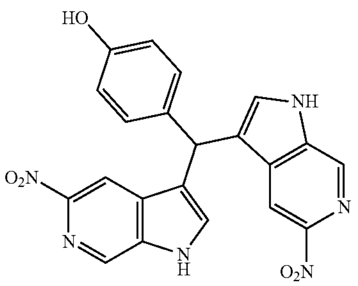 |
TABLE A-continued
| Compound No. | Compound Structure |
| --- | --- |
| 44 | 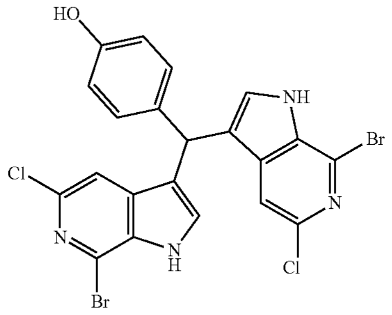 [SMILES: Oc1ccc(C(c2c[nH]c3c(Br)nc(Cl)cc23)c2c[nH]c3c(Br)nc(Cl)cc23)cc1] |
| 45 | 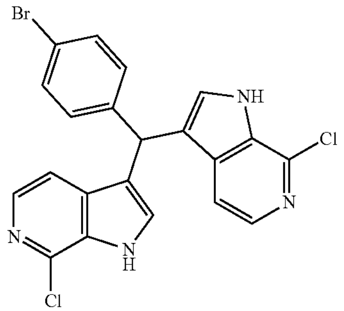 [SMILES: Clc1nccc2c(C(c3ccc(Br)cc3)c3c[nH]c4c(Cl)nccc34)c[nH]c12] |
| 46 | 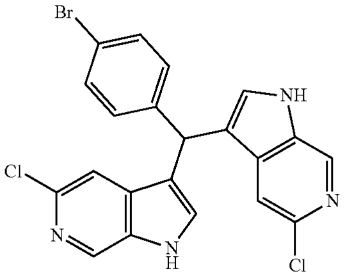 [SMILES: Clc1cc2c(C(c3ccc(Br)cc3)c3c[nH]c4cnc(Cl)cc34)c[nH]c2cn1] |
| 47 | 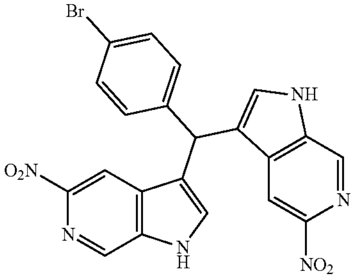 [SMILES: O=[N+]([O-])c1cc2c(C(c3ccc(Br)cc3)c3c[nH]c4cnc([N+](=O)[O-])cc34)c[nH]c2cn1] |
| 48 | 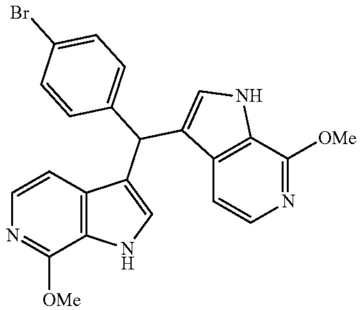 [SMILES: COc1nccc2c(C(c3ccc(Br)cc3)c3c[nH]c4c(OC)nccc34)c[nH]c12] |

TABLE A-continued
| Compound No. | Compound Structure |
|---|---|
| 49 | 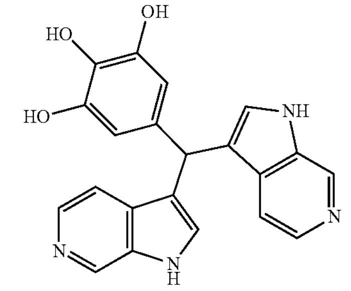 [SMILES: Oc1cc(C(c2c[nH]c3cnccc23)c2c[nH]c3cnccc23)cc(O)c1O] |
| 50 | 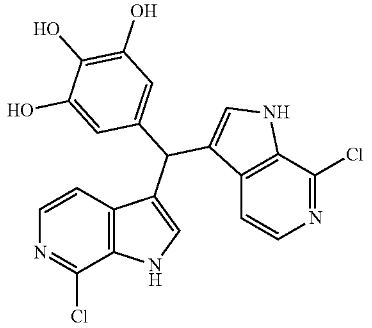 |
| 51 | 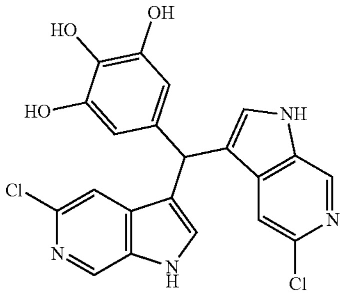 |
| 52 | 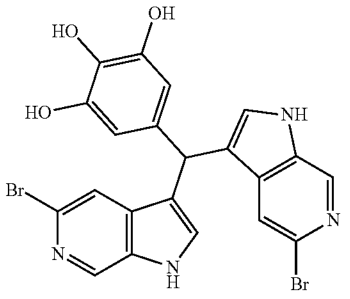 [SMILES: Oc1cc(C(c2c[nH]c3cnc(Cl)cc23)c2c[nH]c3cnc(Cl)cc23)cc(O)c1O] |
| 53 | 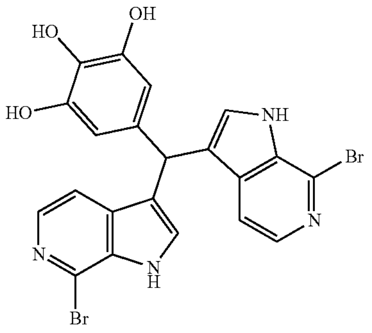 [SMILES: Oc1cc(C(c2c[nH]c3c(Br)nccc23)c2c[nH]c3c(Br)nccc23)cc(O)c1O] |
TABLE A-continued
| Compound No. | Compound Structure |
|---|---|
| 54 | 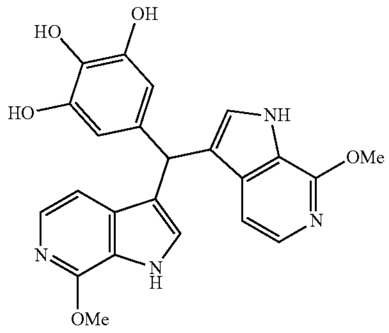 [SMILES: COc1nccc2c(C(c3cc(O)c(O)c(O)c3)c3c[nH]c4c(OC)nccc34)c[nH]c12] |
| 55 | 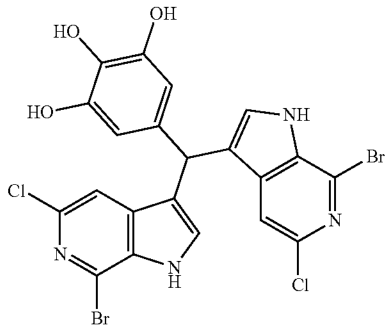 [SMILES: Oc1cc(C(c2c[nH]c3c(Br)nc(Cl)cc23)c2c[nH]c3c(Br)nc(Cl)cc23)cc(O)c1O] |
| 56 | 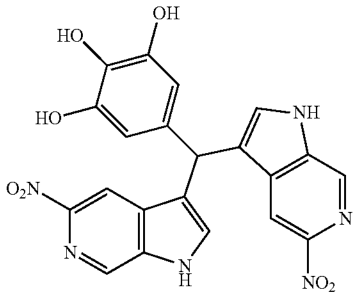 [SMILES: O=[N+]([O-])c1cc2c(C(c3cc(O)c(O)c(O)c3)c3c[nH]c4cnc([N+](=O)[O-])cc34)c[nH]c2cn1] |
| 57 | 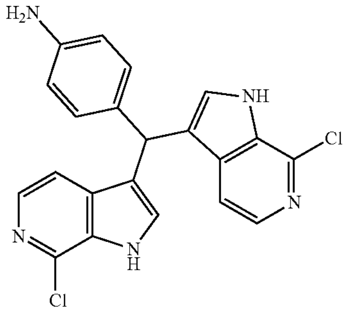 |
| 58 | 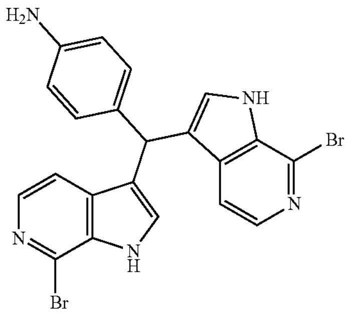 [SMILES: Nc1ccc(C(c2c[nH]c3c(Br)nccc23)c2c[nH]c3c(Br)nccc23)cc1] |

TABLE A-continued

| Compound No. | Compound Structure |
|---|---|
| 59 | 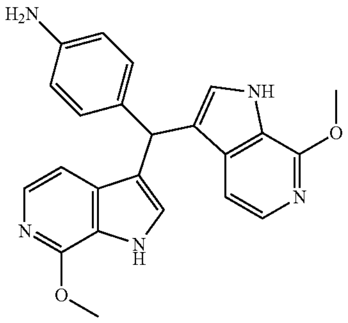 |
| 60 | 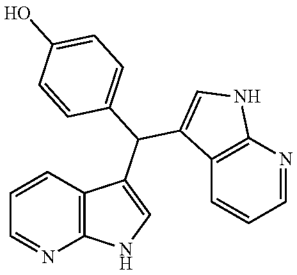 [SMILES: Oc1ccc(C(c2c[nH]c3ncccc23)c2c[nH]c3ncccc23)cc1] |
| 61 | 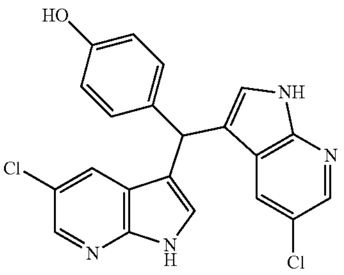 [SMILES: Oc1ccc(C(c2c[nH]c3ncc(Cl)cc23)c2c[nH]c3ncc(Cl)cc23)cc1] |
| 62 | 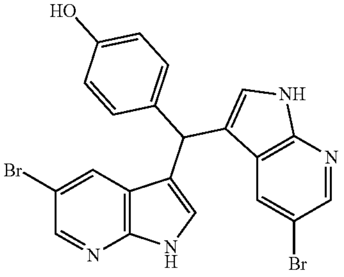 |
| 63 | 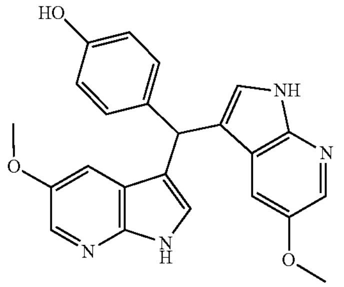 |
| 64 | 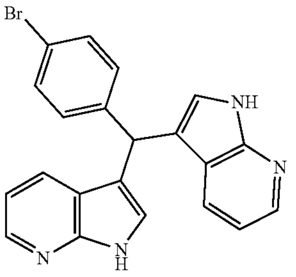 [SMILES: Brc1ccc(C(c2c[nH]c3ncccc23)c2c[nH]c3ncccc23)cc1] |
| 65 | 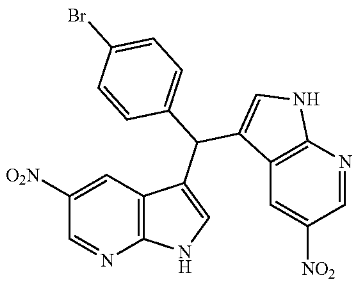 [SMILES: O=[N+]([O-])c1cnc2[nH]cc(C(c3ccc(Br)cc3)c3c[nH]c4ncc([N+](=O)[O-])cc34)c2c1] |
| 66 | 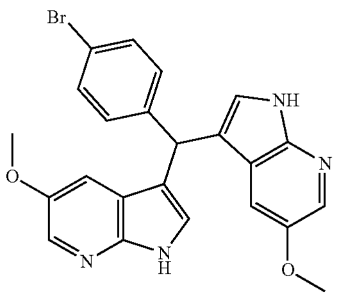 [SMILES: COc1cnc2[nH]cc(C(c3ccc(Br)cc3)c3c[nH]c4ncc(OC)cc34)c2c1] |

In another aspect, the present disclosure provides a compound of Formula II or a pharmaceutically acceptable salt thereof,

II

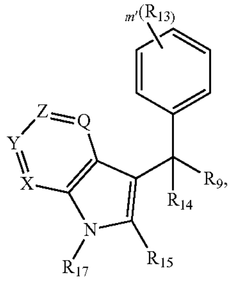

wherein

X is N or $CR_{11a}$;

Y is N or $CR_{11b}$;

Z is N or $CR_{11c}$;

Q is N or $CR_{11d}$;

$R_{11a}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{11b}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{11c}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{11d}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

each occurrence of $R_{13}$ is independently H, halogen, OH, CN, CHO, $NO_2$, $OCF_3$, ($C_1$ to $C_6$) alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, in which said heterocycle comprises at least one heteroatom selected from the group consisting of nitrogen, oxygen and sulfur and is optionally substituted by alkyl or $OR_a$;

or alternatively two $R_{13}$ taken together with the ring atoms they are connected to form a 3-7-membered aromatic or heteroaromatic ring that is optionally substituted by 1-3 substituents each independently selected from the group consisting of halogen, OH, CN, ($C_1$ to $C_4$)alkyl, ($C_1$ to $C_4$)haloalkyl, and ($C_1$ to $C_4$)alkoxy;

$R_{14}$ is H, halogen, OH, CN, $NO_2$, $OCF_3$, ($C_1$ to $C_6$) alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, $(CH_2)_p$($C_3$ to $C_7$)cycloalkyl, $(CH_2)_pOR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_{15}$ is H, halogen, OH, CN, $OCF_3$, ($C_1$ to $C_6$) alkyl, ($C_1$ to $C_6$)alkoxy, ($C_3$ to $C_7$)cycloalkyl, 3-7-membered heterocycle, $NR_aR_b$, $(CH_2)_p$($C_3$ to $C_7$)cycloalkyl, $(CH_2)_p$ $OR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_{17}$ is H, ($C_1$ to $C_6$) alkyl, ($C_3$ to $C_7$)cycloalkyl, 3-7-membered heterocycle, $COR_a$, $CONR_aR_b$, or $SO_2R_a$; in which said heterocycle comprises at least one heteroatom selected from the group consisting of nitrogen, oxygen and sulfur and is optionally substituted by alkyl or $OR_a$;

$R_9$ is halogen, OH, CN, $OCF_3$, ($C_1$ to $C_6$) alkyl, ($C_1$ to $C_6$)alkoxy, ($C_3$ to $C_7$)cycloalkyl, 3-7-membered heterocycle, $OR_a$, $NR_aR_b$, $(CH_2)_p$($C_3$ to $C_7$)cycloalkyl, $(CH_2)_p$ $OR_a$, or $(CH_2)_pSR_a$, in which said heterocycle comprises at least one heteroatom selected from the group consisting of nitrogen, oxygen and sulfur and is optionally substituted by alkyl or $OR_a$;

each occurrence of $R_a$ and $R_b$ are each independently H, ($C_1$ to $C_6$)alkyl, ($C_2$ to $C_6$)alkenyl, ($C_3$ to $C_7$)cycloalkyl, heterocycle, aryl, or heteroaryl;

the alkyl, alkenyl, alkynal, alkoxy, cycloalkyl, aryl, heterocycle, and alkylthio in $R_{11a}$, $R_{11b}$, $R_{11c}$, $R_{11d}$, $R_{13}$, $R_{14}$, $R_{15}$, $R_{17}$, or $R_9$ where applicable, are optionally substituted by 1-3 substituents each independently selected from the group consisting of halogen, OH, CN, ($C_1$ to $C_4$)alkyl, ($C_1$ to $C_4$)haloalkyl, and ($C_1$ to $C_4$)alkoxy;

m' is an integer from 0-5;

each occurrence of p is independently an integer from 1-4; and at least one of X, Y, Z, and Q is N; and provided the compound is not

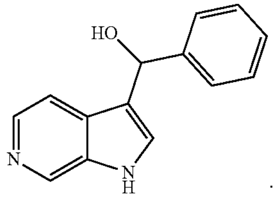 [SMILES: OC(c1ccccc1)c1c[nH]c2cnccc12]

.

In some embodiments, the compound has the structure of Formula IIa, IIb, IIc, or IId:

IIa

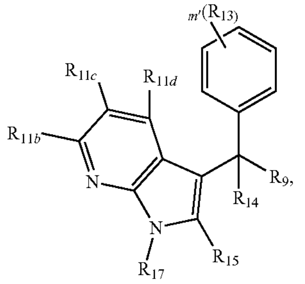

or

IIb

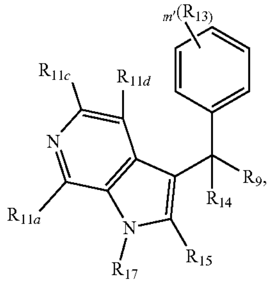

-continued

IIc

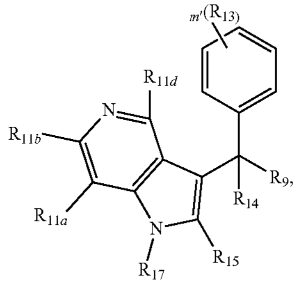

or

IId

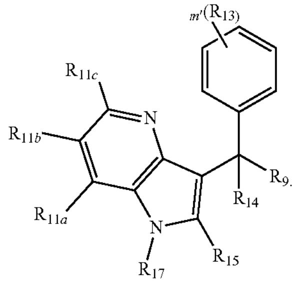

In some embodiments, the compound has the structure of Formula IIa:

IIa

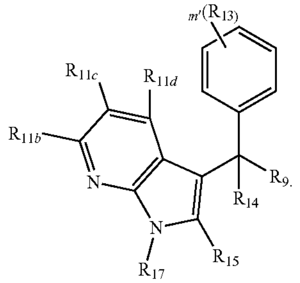

In some embodiments, the compound has the structure of Formula IIb:

IIb

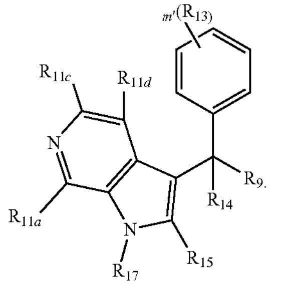

In some embodiments, $R_9$ is halogen, OH, CN, $OCF_3$, ($C_1$ to $C_6$) alkyl, ($C_1$ to $C_6$)alkoxy, $OR_a$, or $NR_aR_b$. In some embodiments, $R_9$ is $OR_a$ or $NR_aR_b$. In some embodiments, $R_9$ is $OR_a$ and $R_a$ is H, ($C_1$ to $C_6$)alkyl, or ($C_2$ to $C_6$)alkenyl. In some embodiments, $R_9$ is $NR_aR_b$ and at least of $R_a$ or $R_b$ is heterocycle, aryl, or heteroaryl. In some embodiments, $R_9$ is selected from the group consisting of OH,

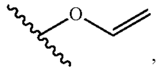

,

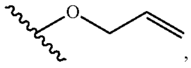

, and

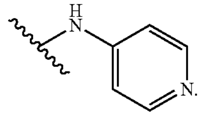

In some embodiments, $R_9$ is OH.

In some embodiments, the compound has the structure of Formula IIe:

IIe

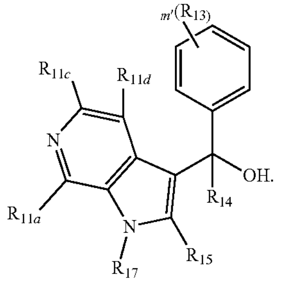

In some embodiments, at least one occurrence of $R_{1a}$ is H, halogen, OH, CN, $OCF_3$, $NR_aR_b$, $NO_2$, $COOR_a$, or CON-$R_aR_b$. Non-limiting examples of halogen include F, Cl, Br, and I. In some embodiments, at least one occurrence of $R_{11a}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{11a}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

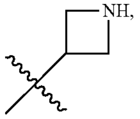

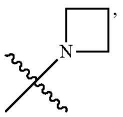

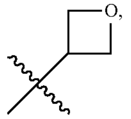

-continued

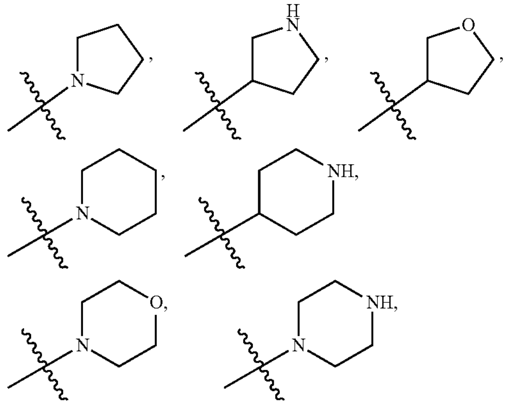

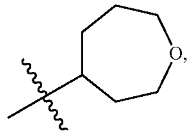

and

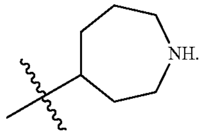

In some embodiments, each occurrence of $R_{11a}$ is independently H, halogen, OH, CN, $OCF_3$, ($C_1$ to $C_6$) alkyl, or ($C_1$ to $C_6$)alkoxy. In some embodiments, at least one occurrence of $R_{11a}$ is H, OH, $OCH_3$, F, Cl, or Br. In some embodiments, each occurrence of $R_{11a}$ is independently H, OH, $OCH_3$, F, Cl, or Br.

In some embodiments, at least one occurrence of $R_{11b}$ is H, halogen, OH, CN, $OCF_3$, $NR_aR_b$, $NO_2$, $COOR_a$, or $CONR_aR_b$. Non-limiting examples of halogen include F, Cl, Br, and I. In some embodiments, at least one occurrence of $R_{11b}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{11b}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

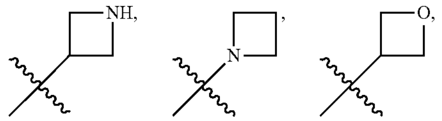

-continued

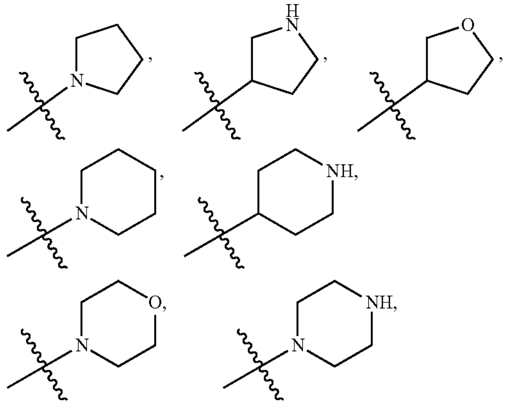

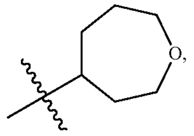

and

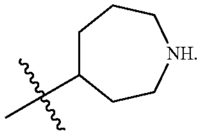

In some embodiments, each occurrence of $R_{11b}$ is independently H, halogen, OH, CN, $OCF_3$, ($C_1$ to $C_6$) alkyl, or ($C_1$ to $C_6$)alkoxy. In some embodiments, at least one occurrence of $R_{11b}$ is H, OH, $OCH_3$, F, Cl, or Br. In some embodiments, each occurrence of $R_{11b}$ is independently H, OH, $OCH_3$, F, Cl, or Br.

In some embodiments, at least one occurrence of $R_{1c}$ is H, halogen, OH, CN, $OCF_3$, $NR_aR_b$, $NO_2$, $COOR_a$, or $CONR_aR_b$. Non-limiting examples of halogen include F, Cl, Br, and I. In some embodiments, at least one occurrence of $R_{1c}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{1c}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

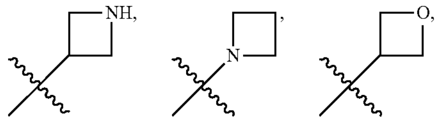

-continued

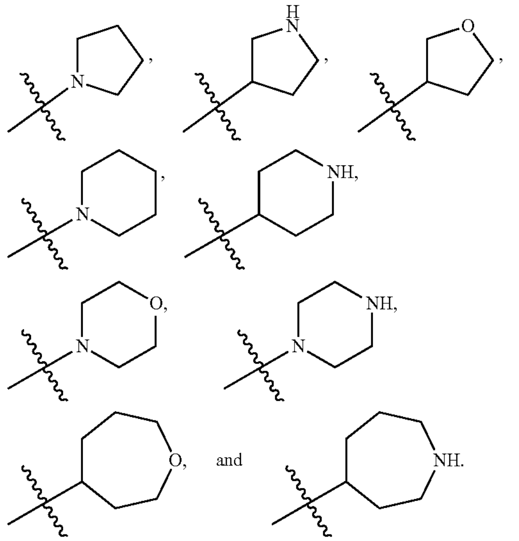

In some embodiments, each occurrence of $R_{11c}$ is independently H, halogen, OH, CN, $OCF_3$, ($C_1$ to $C_6$) alkyl, or ($C_1$ to $C_6$)alkoxy. In some embodiments, at least one occurrence of $R_{11c}$ is H, OH, $OCH_3$, F, Cl, or Br. In some embodiments, each occurrence of $R_{11c}$ is independently H, OH, $OCH_3$, F, Cl, or Br.

In some embodiments, at least one occurrence of $R_{11a}$ is H, halogen, OH, CN, $OCF_3$, $NR_aR_b$, $NO_2$, $COOR_a$, or $CONR_aR_b$. Non-limiting examples of halogen include F, Cl, Br, and I. In some embodiments, at least one occurrence of $R_{11d}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{11d}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

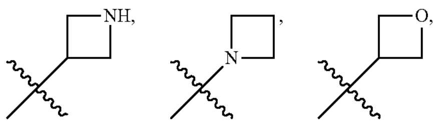

-continued

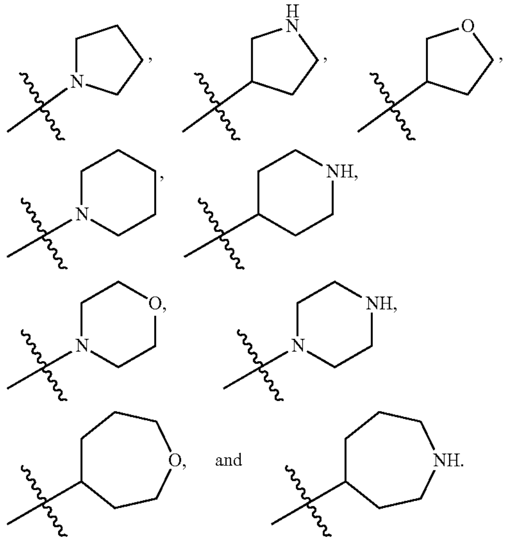

In some embodiments, each occurrence of $R_{11d}$ is independently H, halogen, OH, CN, $OCF_3$, ($C_1$ to $C_6$) alkyl, or ($C_1$ to $C_6$)alkoxy. In some embodiments, at least one occurrence of $R_{11d}$ is H, OH, $OCH_3$, F, Cl, or Br. In some embodiments, each occurrence of $R_{11d}$ is independently H, OH, $OCH_3$, F, Cl, or Br.

In some embodiments, each occurrence of $R_{11a}$ is independently H, halogen, OH, CN, $OCF_3$, ($C_1$ to $C_6$) alkyl, or ($C_1$ to $C_6$)alkoxy; each occurrence of $R_{11b}$ is independently H, halogen, OH, CN, $OCF_3$, ($C_1$ to $C_6$) alkyl, or ($C_1$ to $C_6$)alkoxy; each occurrence of $R_{11c}$ is independently H, halogen, OH, CN, $OCF_3$, ($C_1$ to $C_6$) alkyl, or ($C_1$ to $C_6$)alkoxy; and each occurrence of $R_{11d}$ is independently H, halogen, OH, CN, $OCF_3$, ($C_1$ to $C_6$) alkyl, or ($C_1$ to $C_6$)alkoxy.

In some embodiments, at least one occurrence of $R_{13}$ is H, halogen, OH, CN, $OCF_3$, CHO, $NO_2$, $NH_2$, $COOR_a$, or $CONR_aR_b$. Non-limiting examples of halogen include F, Cl, Br, and I. In some embodiments, at least one occurrence of $R_{13}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. Non-limiting examples of alkynyl include ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. Non-limiting examples of alkylthio include $SCH_3$, $SCH_2CH_3$, $SCH(CH_3)_2$, $SCH_2CH_2CH_3$, $SCH(CH_3)CH_2CH_3$, and $SCH_2CH_2CH(CH_3)_2$. In some embodiments, at least one occurrence of $R_{13}$ is ($C_3$ to $C_7$)cycloalkyl, 3-7-membered heterocycle, or $(CH_2)_p$($C_3$ to $C_7$)cycloalkyl. Non-limiting examples of cycloalkyl include cyclopropyl, cyclobutyl, cyclopentyl, cyclohexyl, and cycloheptyl. Non-limiting examples of heterocycle include

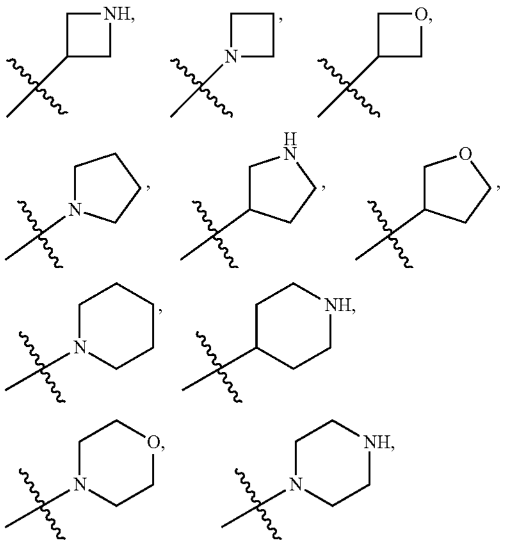

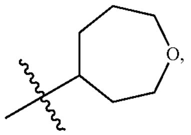

and

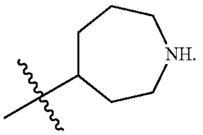

In some embodiments, each occurrence of $R_{13}$ is independently OH, halogen, CN, $NH_2$, $NO_2$, $OCF_3$, ($C_1$ to $C_6$) alkyl, ($C_1$ to $C_6$)alkoxy, or CHO. In some embodiments, at least one occurrence of $R_{13}$ is H, OH, $OCH_3$, F, Cl, or Br. In some embodiments, at least one occurrence of $R_{13}$ is OH. In some embodiments, at least one occurrence of $R_{13}$ is Br, F, or $C_1$. In some embodiments, at least one occurrence of $R_{13}$ is $NO_2$ or $NH_2$. In some embodiments, at least one occurrence of $R_{13}$ is $CH_3$, $CH_2CH_3$, $CH(CH_3)_2$, $CH_2CH_2CH_3$, $OCH_3$, $OCH_2CH_3$, $OCH(CH_3)_2$, $OCH_2CH_2CH_3$, or CHO. In some embodiments, each occurrence of $R_{13}$ is independently H, OH, $CH_3$, $OCH_3$, CHO, F, Cl, or Br.

In some embodiments, m is 0'. In some embodiments, m' is 1. In some embodiments, m' is 2. In some embodiments, m' is 3. In some embodiments, m' is 4.

In some embodiments, the structural moiety

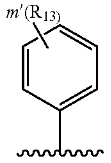

has the structure of

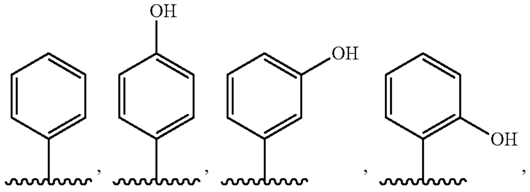

-continued

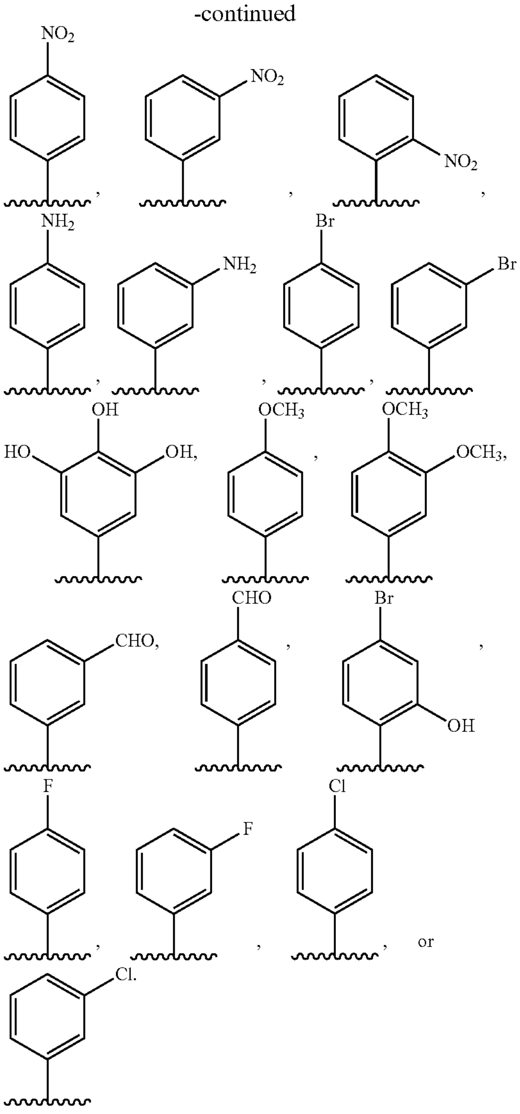

In some embodiments, $R_{14}$ is H, halogen, OH, CN, $OCF_3$, $NR_aR_b$, ($C_1$ to $C_6$) alkyl, ($C_1$ to $C_6$)alkoxy, $(CH_2)_pOR_a$, $(CH_2)_pSR_a$, or $(CH_2)_pNR_aR_b$. Non-limiting examples of halogen include F, Cl, Br, and I. Non-limiting examples of alkyl include methyl, ethyl, propyl, isopropyl, n-butyl, t-butyl, pentyl, isobutyl pentyl, and hexyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. In some embodiments, $R_{14}$ is H, OH, halogen, ($C_1$ to $C_6$) alkyl, or ($C_1$ to $C_6$)alkoxy. In some embodiments, $R_{14}$ is H, Cl, F, Br, OH, $CH_3$, $OCH_3$, $OCF_3$, or $CH_2CH_3$. In some embodiments, $R_{14}$ is H. In some embodiments, $R_{14}$ is Cl. In some embodiments, $R_{14}$ is Br. In some embodiments, $R_{14}$ is OH.

In some embodiments, $R_{15}$ is H, halogen, OH, CN, $OCF_3$, $NR_aR_b$, ($C_1$ to $C_6$) alkyl, ($C_1$ to $C_6$)alkoxy, $(CH_2)_pOR_a$, $(CH_2)_pSR_a$, or $(CH_2)_pNR_aR_b$. Non-limiting examples of halogen include F, Cl, Br, and I. Non-limiting examples of alkyl include methyl, ethyl, propyl, isopropyl, n-butyl, t-butyl, pentyl, isobutyl pentyl, and hexyl. Non-limiting examples of alkoxy include $OCH_3$, $OCH_2CH_3$, $OCH(CH_3)_2$, $OCH_2CH_2CH_3$, $OCH(CH_3)CH_2CH_3$, and $OCH_2CH_2CH(CH_3)_2$. In some embodiments, $R_{15}$ is H, halogen, ($C_1$ to $C_6$)

alkyl, or ($C_1$ to $C_6$)alkoxy. In some embodiments, $R_{15}$ is H, Cl, F, Br, $CH_3$, $OCH_3$, $OCF_3$, or $CH_2CH_3$. In some embodiments, $R_{15}$ is H. In some embodiments, $R_{15}$ is Cl. In some embodiments, $R_{15}$ is Br.

In some embodiments, $R_{17}$ is H, ($C_1$ to $C_6$) alkyl, ($C_3$ to $C_7$)cycloalkyl, $COR_a$, $CONR_aR_b$, or $SO_2R_a$. Non-limiting examples of alkyl include methyl, ethyl, propyl, isopropyl, n-butyl, t-butyl, pentyl, isobutyl pentyl, and hexyl. Non-limiting examples of cycloalkyl include cyclopropyl, cyclobutyl, cyclopentyl, cyclohexyl, and cycloheptyl. In some embodiments, $R_{17}$ is H, ($C_1$ to $C_6$) alkyl, $COR_a$, or $CONR_aR_b$. In some embodiments, $R_{17}$ is H, $CH_3$, $CH_2CH_3$, C(=O)$CH_3$, or C(=O)$NHCH_3$. In some embodiments, $R_{17}$ is H or ($C_1$ to $C_6$) alkyl. In some embodiments, $R_{17}$ is H. In some embodiments, $R_{17}$ is $CH_3$.

In some embodiments, each occurrence of $R_{13}$ is independently OH, halogen, CN, $NH_2$, $NO_2$, $OCF_3$, ($C_1$ to $C_6$) alkyl, ($C_1$ to $C_6$)alkoxy, or CHO; $R_{14}$ is H, halogen, OH, CN, $OCF_3$, ($C_1$ to $C_6$) alkyl, or ($C_1$ to $C_6$)alkoxy; $R_{15}$ is H, halogen, OH, CN, $OCF_3$, ($C_1$ to $C_6$) alkyl, or ($C_1$ to $C_6$)alkoxy; and $R_{17}$ is H, ($C_1$ to $C_6$) alkyl, $COR_a$, or $CONR_aR_b$.

In some embodiments, wherein compound has the structure of Formula IIa or IIb

IIa

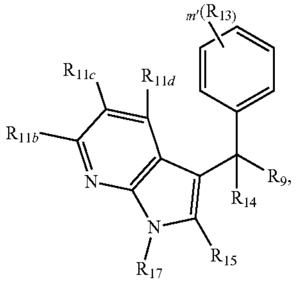

or

IIb

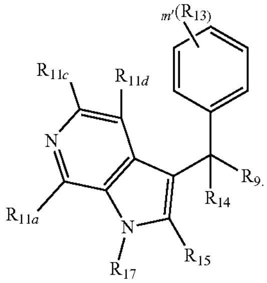

wherein $R_{11a}$ is H, halogen, OH, CN, $OCF_3$, ($C_1$ to $C_6$) alkyl, or ($C_1$ to $C_6$)alkoxy;

$R_{11b}$ is H, halogen, OH, CN, $OCF_3$, ($C_1$ to $C_6$) alkyl, or ($C_1$ to $C_6$)alkoxy;

$R_{11c}$ is H, halogen, OH, CN, $OCF_3$, ($C_1$ to $C_6$) alkyl, or ($C_1$ to $C_6$)alkoxy;

$R_{11d}$ is H, halogen, OH, CN, $OCF_3$, ($C_1$ to $C_6$) alkyl, or ($C_1$ to $C_6$)alkoxy;

$R_9$ is $OR_a$ or $NR_aR_b$;

each occurrence of $R_{13}$ is independently OH, halogen, CN, $NH_2$, $NO_2$, $OCF_3$, ($C_1$ to $C_6$) alkyl, ($C_1$ to $C_6$)alkoxy, or CHO;

$R_{14}$ is H, halogen, OH, CN, $OCF_3$, ($C_1$ to $C_6$) alkyl, or ($C_1$ to $C_6$)alkoxy;

$R_{15}$ is H, halogen, OH, CN, $OCF_3$, ($C_1$ to $C_6$) alkyl, or ($C_1$ to $C_6$)alkoxy; and $R_{17}$ is H, ($C_1$ to $C_6$) alkyl, $COR_a$, or $CONR_aR_b$.

In some embodiments, at least one occurrence of $R_a$ or $R_b$ is independently H, ($C_1$ to $C_6$)alkyl, ($C_2$ to $C_6$)alkenyl, or ($C_3$ to $C_7$)cycloalkyl. Non-limiting examples of alkyl include methyl, ethyl, propyl, isopropyl, n-butyl, t-butyl, pentyl, isobutyl pentyl, and hexyl. Non-limiting examples of alkenyl include ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. In some embodiments, at least one occurrence of $R_a$ or $R_b$ is independently heterocycle, aryl, or heteroaryl. In some embodiments, at least one occurrence of $R_a$ or $R_b$ is independently H, alkyl or alkenyl. In some embodiments, at least one occurrence of $R_a$ or $R_b$ is independently H, Me, Et, Pr, or Bu. In some embodiments, at least one occurrence of $R_a$ or $R_b$ is independently a heterocycle selected from the group consisting of

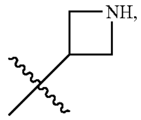 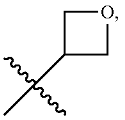 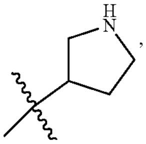 ,

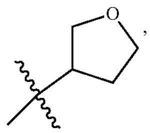 , 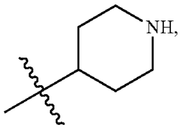 and

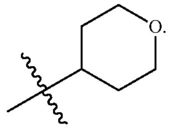

In some embodiments, at least one occurrence of $R_a$ or $R_b$ is independently H

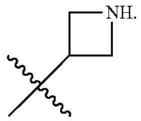 [SMILES: *C1CNC1]

In some embodiments, the compound is selected from the group consisting of compounds 1-33 as shown in Table B.

TABLE B

| Compound No. | Compound Structure |
|---|---|
| 1 | 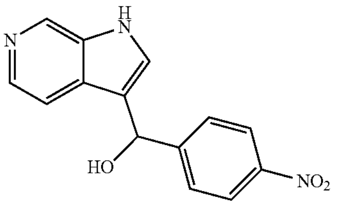 [SMILES: O=[N+]([O-])c1ccc(C(O)c2c[nH]c3cnccc23)cc1] |

TABLE B-continued
| Compound No. | Compound Structure |
|---|---|
| 2 | 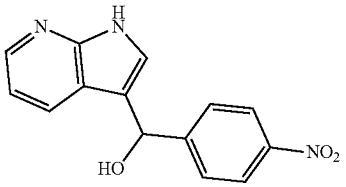 [SMILES: O=[N+]([O-])c1ccc(C(O)c2c[nH]c3ncccc23)cc1] |
| 3 | 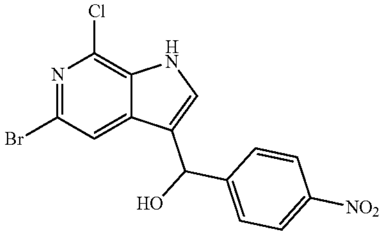 [SMILES: O=[N+]([O-])c1ccc(C(O)c2c[nH]c3c(Cl)nc(Br)cc23)cc1] |
| 4 | 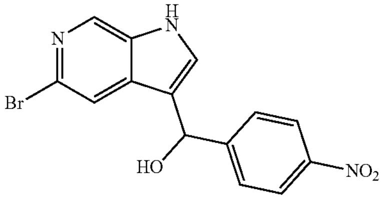 [SMILES: O=[N+]([O-])c1ccc(C(O)c2c[nH]c3cnc(Br)cc23)cc1] |
| 5 | 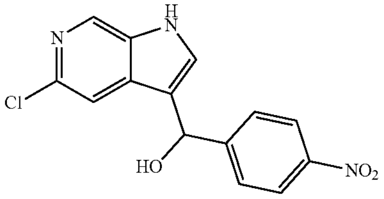 [SMILES: O=[N+]([O-])c1ccc(C(O)c2c[nH]c3cnc(Cl)cc23)cc1] |
| 6 | 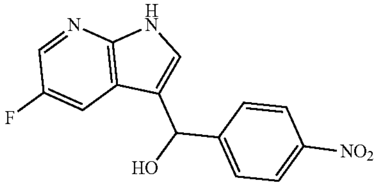 [SMILES: O=[N+]([O-])c1ccc(C(O)c2c[nH]c3ncc(F)cc23)cc1] |
| 7 | 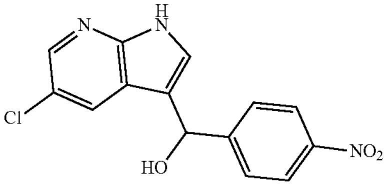 [SMILES: O=[N+]([O-])c1ccc(C(O)c2c[nH]c3ncc(Cl)cc23)cc1] |
| 8 | 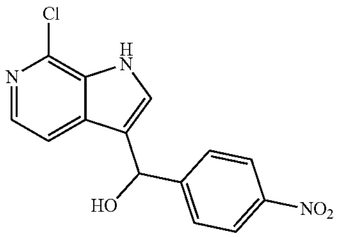 [SMILES: O=[N+]([O-])c1ccc(C(O)c2c[nH]c3c(Cl)nccc23)cc1] |
TABLE B-continued
| Compound No. | Compound Structure |
|---|---|
| 9 | 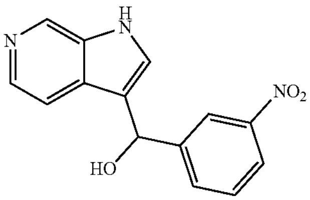 [SMILES: O=[N+]([O-])c1cccc(C(O)c2c[nH]c3cnccc23)c1] |
| 10 | 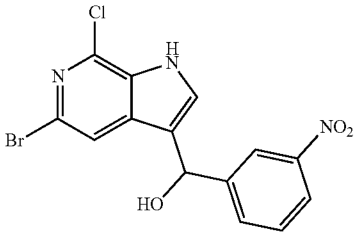 [SMILES: O=[N+]([O-])c1cccc(C(O)c2c[nH]c3c(Cl)nc(Br)cc23)c1] |
| 11 | 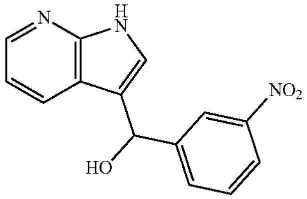 [SMILES: O=[N+]([O-])c1cccc(C(O)c2c[nH]c3ncccc23)c1] |
| 12 | 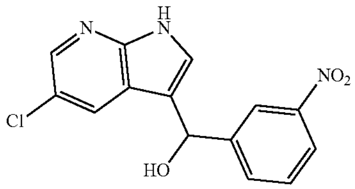 [SMILES: O=[N+]([O-])c1cccc(C(O)c2c[nH]c3ncc(Cl)cc23)c1] |
| 13 | 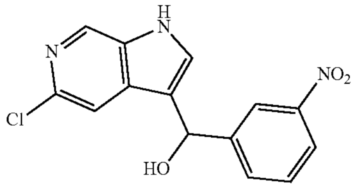 [SMILES: O=[N+]([O-])c1cccc(C(O)c2c[nH]c3cnc(Cl)cc23)c1] |
| 14 | 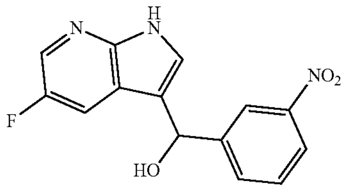 [SMILES: O=[N+]([O-])c1cccc(C(O)c2c[nH]c3ncc(F)cc23)c1] |
| 15 | 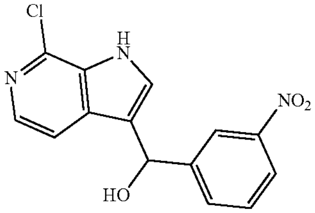 [SMILES: O=[N+]([O-])c1cccc(C(O)c2c[nH]c3c(Cl)nccc23)c1] |

TABLE B-continued
| Compound No. | Compound Structure |
|---|---|
| 16 | 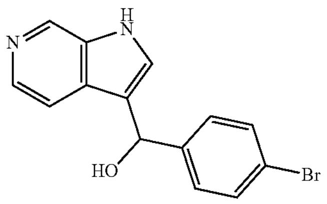 [SMILES: OC(c1ccc(Br)cc1)c1c[nH]c2cnccc12] |
| 17 | 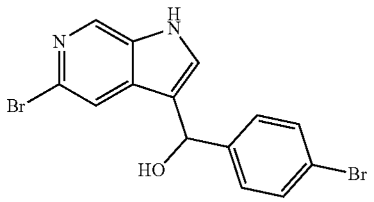 [SMILES: OC(c1ccc(Br)cc1)c1c[nH]c2cnc(Br)cc12] |
| 18 | 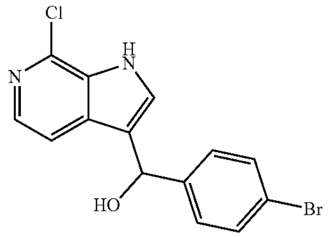 [SMILES: OC(c1ccc(Br)cc1)c1c[nH]c2c(Cl)nccc12] |
| 19 | 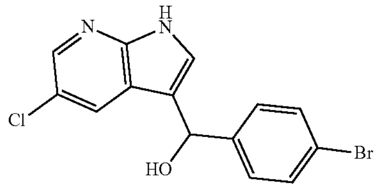 [SMILES: OC(c1ccc(Br)cc1)c1c[nH]c2ncc(Cl)cc12] |
| 20 | 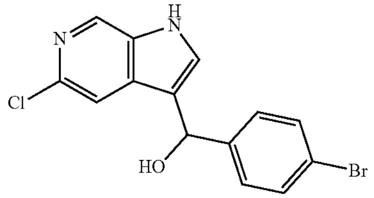 [SMILES: OC(c1ccc(Br)cc1)c1c[nH]c2cnc(Cl)cc12] |
| 21 | 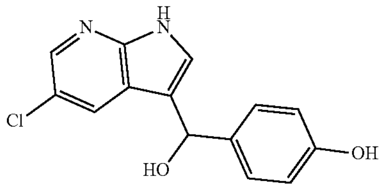 [SMILES: Oc1ccc(C(O)c2c[nH]c3ncc(Cl)cc23)cc1] |
| 22 | 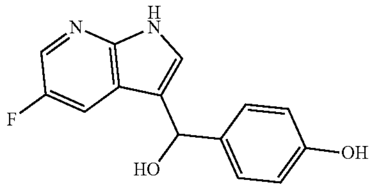 [SMILES: Oc1ccc(C(O)c2c[nH]c3ncc(F)cc23)cc1] |
TABLE B-continued
| Compound No. | Compound Structure |
|---|---|
| 23 | 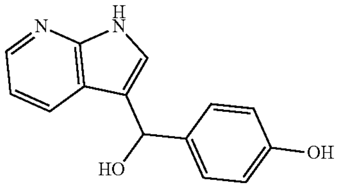 [SMILES: Oc1ccc(C(O)c2c[nH]c3ncccc23)cc1] |
| 24 | 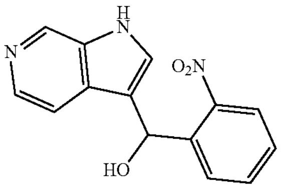 [SMILES: O=[N+]([O-])c1ccccc1C(O)c1c[nH]c2cnccc12] |
| 25 | 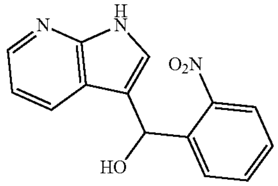 [SMILES: O=[N+]([O-])c1ccccc1C(O)c1c[nH]c2ncccc12] |
| 26 | 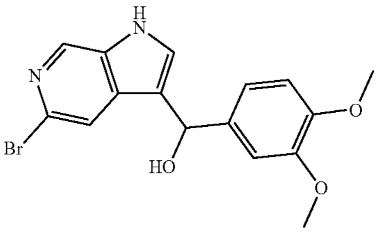 [SMILES: COc1ccc(C(O)c2c[nH]c3cnc(Br)cc23)cc1OC] |
| 27 | 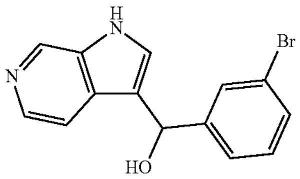 [SMILES: OC(c1cccc(Br)c1)c1c[nH]c2cnccc12] |
| 28 | 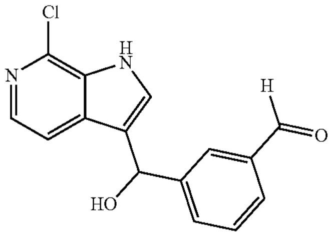 [SMILES: O=Cc1cccc(C(O)c2c[nH]c3c(Cl)nccc23)c1] |
| 29 | 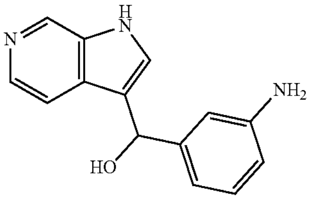 [SMILES: Nc1cccc(C(O)c2c[nH]c3cnccc23)c1] |

TABLE B-continued

| Compound No. | Compound Structure |
|---|---|
| 30 | 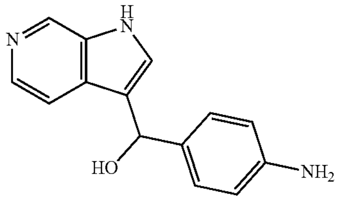 [SMILES: Nc1ccc(C(O)c2c[nH]c3cnccc23)cc1] |
| 31 | 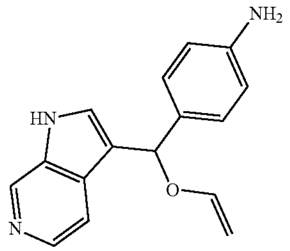 [SMILES: C=COC(c1ccc(N)cc1)c1c[nH]c2cnccc12] |
| 32 | 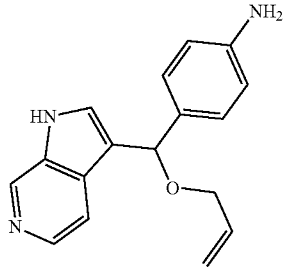 [SMILES: C=CCOC(c1ccc(N)cc1)c1c[nH]c2cnccc12] |
| 33 | 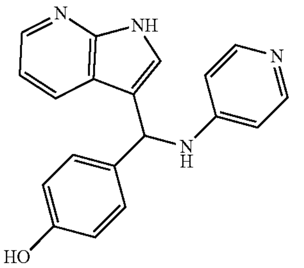 [SMILES: Oc1ccc(C(Nc2ccncc2)c2c[nH]c3ncccc23)cc1] |

In another aspect, the present disclosure provides a pharmaceutical composition including compounds as described herein and pharmaceutically acceptable excipients. In some embodiments, the pharmaceutical composition further includes an antimicrobial agent. In some embodiments, the antimicrobial agent is an antibacterial agent.

In some embodiments, the antimicrobial agent is an antifungal agent. In some embodiments, the antimicrobial agent is a macrolide, a folic acid synthesis inhibitor, a fluoroquinolone, an aminoglycoside, a monobactam, a cephalosporin, a glycopeptide, a β-lactam, a carbapenem, or a tetracycline.

In some embodiments, the present disclosure provides a pharmaceutical composition as described herein, where the antimicrobial agent is selected from the group of ampicillin, imipenem, cephalexin, erythromycin, aztreonam, trimethoprim, streptomycin, ciprofloxacin, vancomycin, doxycycline, and kanamycin.

In some embodiments, the present disclosure provides a pharmaceutical composition as described herein, including a compound selected from the group consisting of compounds 1-66 as shown in Tables A and B. and an antimicrobial agent selected from the group consisting of ampicillin, imipenem, cephalexin, erythromycin, streptomycin, vancomycin, doxycycline, and kanamycin. In some embodiments, the pharmaceutical composition further comprises one or more pharmaceutically acceptable excipients.

Utility and Methods of Use

In some embodiments, it has been surprisingly found that the compound of Formula I or II described herein can be used to treat a microbial infection and/or potentiate the anti-microbe action of an existing antibiotic.

In another aspect, the present disclosure provides a method of treating, preventing, or reducing the risk of a microbial infection in a subject, the method comprising administering a compound of Formula I or II described herein, or a pharmaceutical composition thereof.

In some embodiments, the method further comprises administering to the subject an antimicrobial agent. In some embodiments, the antimicrobial agent is potentiated by the compound described herein.

In some embodiments, the method comprises treating, preventing, or reducing the risk of biofilms, hemotoxicity, and/or virulence of a microbial infection.

In some embodiments, the microbial infection includes an infection caused by one or more bacteria, yeast, fungi, or combinations thereof. In some embodiments, the microbial infection includes an infection caused by one or more bacteria. In some embodiments, the microbial infection includes an infection caused by one or more yeast. In some embodiments, the microbial infection includes an infection caused by one or more fungi.

In some embodiments, the administration is performed once daily.

In some embodiments, the microbes are clinically antibiotic resistant.

In some embodiments, the microbes form biofilms.

In another aspect, the present disclosure provides a method of inhibiting or extinguishing the growth of one or more microbial cultures in vitro, the method including administering an antimicrobial agent and a compound as described herein.

In a further another aspect, the present disclosure provides a method of inhibiting or extinguishing the growth, virulence, or hemotoxicity of one or more microbial cultures in vitro, the method including administering an antimicrobial agent and a compound or the pharmaceutical composition as described herein.

In a further another aspect, the present disclosure provides a method of reducing the expression of bacterial genes promoting resistance of the bacterial cells to antibiotics, the method including administering a compound or the pharmaceutical composition as described herein.

In some embodiments, the present disclosure provides a method of reducing the expression of bacterial genes promoting virulence of the bacterial cells and their resistance to antibiotics as described herein, the method including administering a compound or the pharmaceutical composition as described herein, where an antimicrobial agent is also administered to the bacterial cells.

In some embodiments, the bacterial genes promoting virulence of the bacterial cells and their resistance to antibiotics include mecA, blaZ, and fnbA.

In a further another aspect, the present disclosure provides a method of reducing of global regulator genes in bacterial cells, the method including administering a compound or the pharmaceutical composition as described herein.

In some embodiments, an antimicrobial agent is also administered to the bacterial cells.

In some embodiments, the global regulator genes include sarA, agrA, and RNA III.

In some embodiments, the present disclosure provides a method as described herein, where the antimicrobial agent is a macrolide, a folic acid synthesis inhibitor, a fluoroquinolone, an aminoglycoside, a monobactam, a cephalosporin, a glycopeptide, a β-lactam, a carbapenem, or a tetracycline.

In some embodiments, the present disclosure provides a method as described herein, where the antimicrobial agent is selected from the group consisting of erythromycin, trimethoprim, ciprofloxacin, streptomycin, aztreonam, cefalexin, vancomycin, ampicillin, doxycycline, and kanamycin.

In some embodiments, the present disclosure provides a method as described herein, where the antimicrobial agent is selected from the group of vancomycin and ampicillin.

In some embodiments, the microbe is Gram-positive bacteria.

In some embodiments, the microbe is Gram-negative bacteria.

In some embodiments, the microbe is a mixture of both Gram-positive and Gram-negative bacteria.

In some embodiments, the microbe is selected from the group consisting of *Bacillus cereus, Streptococcus pyogenes, Streptococcus pneumoniae, Staphylococcus aureus, Enterococcus faecium, Corynebacterium diphtheriae, Escherichia coli, Salmonella typhimurium, Pseudomonas aeruginosa, Klebsiella pneumoniae, Candida albicans*, and mixtures thereof.

In some embodiments, the microbe is selected from the group consisting of *Staphylococcus aureus, Streptococcus pneumoniae, Klebsiella pneumoniae Escherichia coli*, and a combination thereof.

In some embodiments, the microbe is *Staphylococcus aureus, Enterococcus faecium, Klebsiella pneumoniae*, or a mixture thereof.

In some embodiments, the microbe is *Staphylococcus aureus*. In some embodiments, the microbe is methicillin-resistant *Staphylococcus aureus* (MRSA).

In some embodiments, the microbe is *Klebsiella pneumoniae*. In some embodiments, the microbe is meropenem- and/or ciprofloxacin-resistant *Klebsiella pneumoniae.*

In some embodiments, the subject is a domestic animal. In some embodiments, the subject is a mammal. In some embodiments, the subject is a human.

Pharmaceutical Compositions

This disclosure also provides a pharmaceutical composition including at least one of the compounds as described herein or a pharmaceutically acceptable salt thereof, optionally an antibiotic agent, and a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the subject. Some examples of materials which can serve as pharmaceutically acceptable carriers include, but are not limited to: sugars, such as lactose, glucose, and sucrose; starches, such as corn starch and potato starch; cellulose and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as butylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, some embodiments of the present pharmaceutical agents may be provided in the form of pharmaceutically acceptable salts. The term "pharmaceutically acceptable salt", in this respect, refers to the relatively non-toxic, inorganic and organic acid addition salts of compounds of the present disclosure. These salts can be prepared in situ during the final isolation and purification of the compounds of the disclosure, or by separately reacting a purified compound of the disclosure in its free base form with a suitable organic or inorganic acid, and isolating the salt thus formed. Representative salts include, but are not limited to, the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al., (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, butionic, succinic, glycolic, stearic, lactic, malic, tartaric, citric, ascorbic, palmitic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like.

In other cases, the compounds of the present disclosure may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present disclosure. These salts can likewise be prepared in situ during the final isolation and purification of the compounds, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like. (See, for example, Berge et al., supra)

Wetting agents, emulsifiers, and lubricants, such as sodium lauryl sulfate, magnesium stearate, and polyethylene oxide-polybutylene oxide copolymer, as well as coloring agents, release agents, coating agents, sweetening, flavoring, and perfuming agents, preservatives, and antioxidants, can also be present in the compositions.

Formulations of the present disclosure include those suitable for oral, nasal, topical (including buccal and sublingual), rectal, vaginal, and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient, which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia), and/or as mouth washes, and the like, each containing a predetermined amount of a compound of the present disclosure as an active ingredient. A compound disclosed herein may also be administered as a bolus, electuary, or paste.

In solid dosage forms of the disclosure for oral administration (capsules, tablets, pills, dragees, powders, granules, and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose, and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polybutylene oxide copolymer; absorbents, such as kaolin and bentonite clay; lubricants, such a talc, calcium stearate, magnesium stearate, solid polyethylene glycols, sodium lauryl sulfate, and mixtures thereof, and coloring agents. In the case of capsules, tablets, and pills, the pharmaceutical compositions may also include buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxybutylmethyl cellulose), lubricant, inert diluent, preservative, disintegrant (for example, sodium starch glycolate or cross-linked sodium carboxymethyl cellulose), surface-active, or dispersing agent. Molded tablets, may be, made by molding in a suitable machine a mixture of the powdered compound moistened with an inert liquid diluent.

The tablets, and other solid dosage forms of the pharmaceutical compositions of the present disclosure, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxybutylmethyl cellulose in varying butortions to provide the desired release profile, other polymer matrices, liposomes, and/or microspheres. They may be sterilized by, for example, filtration through a bacteria-retaining filter, or by incorporating sterilizing agents in the form of sterile solid compositions, which can be dissolved in sterile water, or some other sterile injectable medium, immediately before use. These compositions may also optionally contain opacifying agents and may be of a composition that they release the active ingredient(s) only, or preferentially, in a certain portion of the gastrointestinal tract, optionally, in a delayed manner. Examples are embedding compositions, which can be used include polymeric substances and waxes. The active ingredient can also be in micro-encapsulated form, if apbutriate, with one or more of the above-described excipients.

Liquid dosage forms for oral administration of the compounds disclosed herein include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof. Additionally, cyclodextrins, e.g., hydroxybutyl-β-cyclodextrin, may be used to solubilize compounds.

Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Formulations of the pharmaceutical compositions disclosed herein for rectal or vaginal administration may be presented as a suppository, which may be prepared by mixing one or more compounds disclosed herein with one or more suitable nonirritating excipients or carriers including, for example, cocoa butter, polyethylene glycol, a suppository wax, or a salicylate, and which is solid at room temperature, but liquid at body temperature and, therefore, will melt in the rectum or vaginal cavity and release the active pharmaceutical agents disclosed herein.

Formulations disclosed herein which are suitable for vaginal administration also include pessaries, tampons, creams, gels, pastes, foams, or spray formulations containing such carriers as are known in the art to be apbutriate.

Dosage forms for the topical or transdermal administration of a compound disclosed herein include powders, sprays, ointments, pastes, creams, lotions, gels, solutions, patches, and inhalants. The active compound may be mixed under sterile conditions with a pharmaceutically acceptable carrier, and with any preservatives, buffers, or butellants which may be required.

The ointments, pastes, creams, and gels may contain, in addition to an active compound as disclosed herein, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound as disclosed herein, excipients such as lactose, talc, silicic acid, aluminum hydroxide, calcium silicates, and polyamide powder, or mixtures of these substances. Sprays can additionally contain customary butellants, such as chlorofluorohydrocarbons and volatile unsubstituted hydrocarbons, such as butane.

Transdermal patches have the added advantage of providing controlled delivery of a compound as disclosed herein to the body. Such dosage forms can be made by dissolving, or dispersing the pharmaceutical agents in the buter medium. Absorption enhancers can also be used to increase the flux of the pharmaceutical agents disclosed herein across the skin. The rate of such flux can be controlled, by either providing a rate controlling membrane or dispersing the compound in a polymer matrix or gel.

Ophthalmic formulations, eye ointments, powders, solutions, and the like, are also contemplated as being within the scope of this disclosure.

Pharmaceutical compositions as disclosed herein suitable for parenteral administration include one or more compounds as disclosed herein in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient, or suspending or thickening agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. One strategy for depot injections includes the use of polyethylene oxide-polybutylene oxide copolymers where the vehicle is fluid at room temperature and solidifies at body temperature.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions, which are compatible with body tissue.

When the compounds disclosed herein are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds and pharmaceutical compositions disclosed herein can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound as disclosed herein may be administered concurrently with another anti-HCV agent), or they may achieve different effects (e.g., control of any adverse effects).

The compounds disclosed herein may be administered intravenously, intramuscularly, intraperitoneally, subcutaneously, topically, orally, or by other acceptable means. The compounds may be used to treat arthritic conditions in mammals (i.e., humans, livestock, and domestic animals), birds, lizards, and any other organism, which can tolerate the compounds.

The disclosure also provides a pharmaceutical pack or kit including one or more containers filled with one or more of the ingredients of the pharmaceutical compositions disclosed herein. Optionally associated with such container(s) can be a notice in the form prescribed by a governmental agency regulating the manufacture, use or sale of pharmaceuticals or biological products, which notice reflects approval by the agency of manufacture, use or sale for human administration.

Methods of Preparation

Following are general synthetic schemes for manufacturing compounds of the present invention. These schemes are illustrative and are not meant to limit the possible techniques one skilled in the art may use to manufacture the compounds disclosed herein. Different methods will be evident to those skilled in the art. Additionally, the various steps in the synthesis may be performed in an alternate sequence or order to give the desired compound(s). All documents cited herein are incorporated herein by reference in their entirety. For example, the following reactions are illustrations, but not limitations of the preparation of some of the starting materials and compounds disclosed herein.

Scheme 1 below describes synthetic routes which may be used for the synthesis of compounds of the present invention, e.g., compounds having a structure of Formula I or II or a precursor thereof. Various modifications to these methods may be envisioned by those skilled in the art to achieve similar results to that of the inventions given below. In the embodiments below, the synthetic route is described using compounds having the structure of Formula I or II or a precursor thereof as examples. The general synthetic routes described in Scheme 1 and examples described in the Example section below illustrate methods used for the preparation of the compounds described herein.

Compound I-1 as shown in Scheme 1 can be prepared by any method known in the art and/or is commercially available. Substituents are defined herein. As shown in Scheme 1, the first step is a condensation step of azaindole and substituted benzaldehyde using an inorganic base and protic solvent system. Potassium carbonate ($K_2CO_3$) was added to the MeOH/$H_2O$ mixture and stirred until dissolved. The respective azaindole I-1 was then added and allowed to stir for 10 mins at room temperature. The substituted benzaldehyde I-2 was then added in a stepwise manner and the reaction allowed to progress for 48 h at room temperature.

The reaction progression was periodically monitored by TLC analysis. Respective intermediates I-3 were achieved in yields between 55-88% based on recovery after chromatography.

Step One reaction reagents and conditions include:

Substituted benzaldehyde—2 mmol (1 equivalent);

Azaindole—4 mmol (2 equivalents);

$K_2CO_3$ —15 mmol (7.5 equivalents);

$MeOH/H_2O$ (1:1)—5 mL;

Room temperature, 48 h.

In the second step, Intermediate I-3 was added to the solution of $K_2CO_3$ in $MeOH/H_2O$ and subjected to microwave irradiation. This resulted in dehydration of intermediate I-3 into an alkylidene intermediate I-4. In the third step, an equivalent amount of second azaindole moiety was added in a stepwise manner to the reaction which resulted in the formation of the desired substituted phenyl bis azaindole compound I-5.

Step Two and Three reaction reagents and conditions include:

Intermediate I-3—2 mmol (1 equivalent);

Azaindole—2 mmol (1 equivalent);

$K_2CO_3$—15 mmol (7.5 equivalents);

$MeOH/H_2O$ (1:1)—5 mL;

Microwave irradiation; 30 mins.

Scheme 1

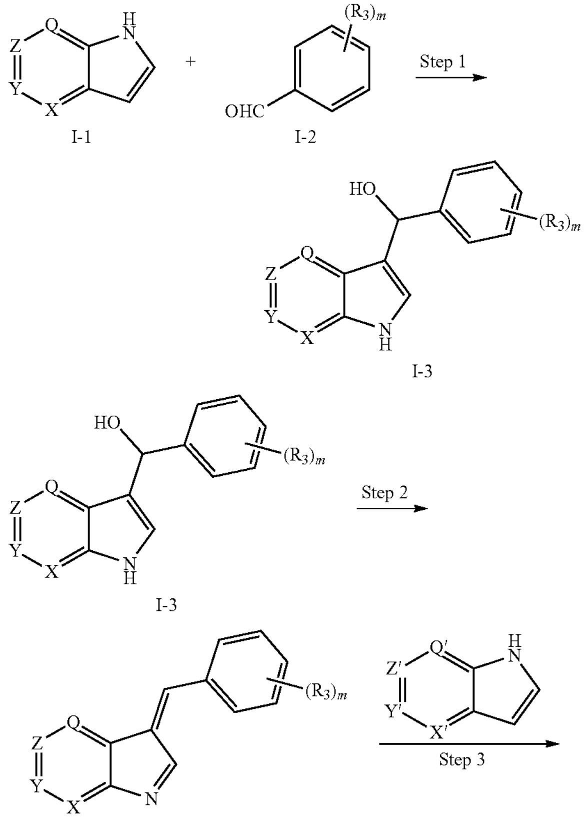

I-1 I-2 I-3 I-3 I-4

-continued

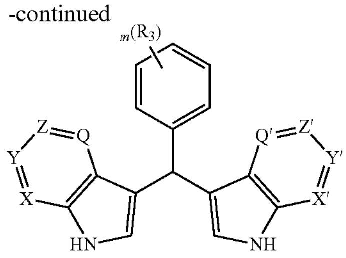

I-5

EQUIVALENTS

The representative examples which follow are intended to help illustrate the disclosure, and are not intended to, nor should they be construed to, limit its scope. Indeed, various modifications of the disclosure and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification, and guidance which can be adapted to the practice of this invention in its various embodiments and equivalents thereof.

EXAMPLES

General Experimental

All solvents and reagents were purchased as analytical grade and purified by established protocols. All fine chemicals were purchased from commercial suppliers and used without further purification. Reactions were monitored by thin layer chromatography (TLC) with pre-coated 250 μm thick silica gel 60 PF254+366 aluminum-backed plates (Sigma-Aldrich), and compounds visualised by UV light (254 nm) irradiation and/or exposure to iodine vapour. Preparative Thin Layer Chromatography (PTLC) was done using 20 cm×20 cm glass plates coated with 250 μm-thick silica gel 60 GF254 (Analtech). Gravity column chromatography (CC) was carried out using silica gel 60, 70-230 mesh (Sigma-Aldrich).

The melting points of the isolated compounds were acquired on a Reichert micro melting point apparatus. $^1H$, $^{13}C$, $^1H$-$^{13}C$ HSQC, $^1H$-$^{13}C$ HMBC, $^1H$-$^1H$ COSY and DEPT-135 NMR experiments were done on a Bruker 600 MHz Avance III Ultrashield Plus Spectrometer at 25° C. Samples submitted for NMR analysis were dissolved in deuterated dimethyl sulfoxide DMSO-$d_6$) (Sigma Aldrich). All chemical shifts were referenced to the internal standard tetramethylsilane (TMS). Mass spectroscopy was performed by Electrospray Ionosation (ESI) in a Bruker MicrOTOFq Spectrometer.

Example 1. Compound 1 ((4-nitrophenyl)(1H-pyrrolo[2,3-c]pyridin-3-yl)methanol

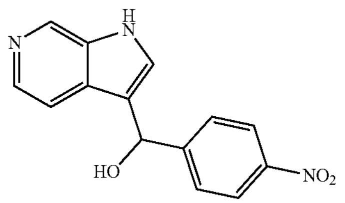 [SMILES: O=[N+]([O-])c1ccc(C(O)c2c[nH]c3cnccc23)cc1]

10 mmol (11.81 mg) of 6-azaindole was added to a solution of 15 mmol (20.73 mg) $K_2CO_3$, 10 mmol (28.84 mg) sodium dodecyl sulphate (SDS) in 10 mL of methanol and water in a 1:1 ratio (reaction solution A). The reaction was allowed to stir for 30 mins at 25° C. 15 mmol (22.65 mg) of 4-nitrobenzaldehyde was added in a stepwise manner and allowed to stir continually for 72 h. The reaction progression was monitored periodically by thin layer chromatography. A pale white precipitate was formed, and the solution was filtered. The residue was washed repeatedly with dd $H_2O$ and then methanol which provided 18.3 mg (68% recovered yield) of (4-nitrophenyl)(1H-pyrrolo[2,3-c]pyridin-3-yl)methanol; $R_f$=0.14 (9 DCM:1 MeOH); m.p.=199° C.; $^1$H NMR (600 MHz DMSO-d6)=δ6.08 (1H, s), δ6.15 (1H, s), δ7.14 (1H, d), δ7.46 (1H, s), δ7.73 (2H, d), δ8.00 (1H, d), δ8.19 (2H, d), δ8.69 (1H, s), δ11.50 (1H, s); $^{13}$C NMR (150 MHz DMSO-d6)=δ 67.69, 114.00, 118.38, 123.29, 127.00, 127.24, 126.69, 133.73, 134.58, 137.34, 146.21, 153.25.

Example 2. Compound 2 ((4-nitrophenyl)(1H-pyrrolo[2,3-b]pyridin-3-yl)methanol

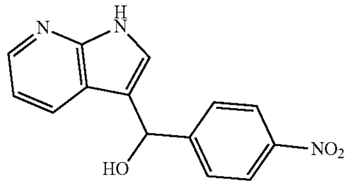 [SMILES: O=[N+]([O-])c1ccc(C(O)c2c[nH]c3ncccc23)cc1]

(4-nitrophenyl)(1H-pyrrolo[2,3-b]pyridin-3-yl)methanol was prepared in the similar manner to example 1, except that 4-nitrobenzaldehyde was added to 7 azaindole in reaction solution A. The crude mixture was filtered and washed with water and MeOH and the residue collected and dried. (4-nitrophenyl)(1H-pyrrolo[2,3-b]pyridin-3-yl)methanol was recovered as a yellow solid with a recovered yield of 25.9 mg (96.3%); $R_f$=0.04 (9 DCM:1 MeOH); m.p.=181° C.; $^1$H NMR (600 MHz DMSO-d6)=δ6.05 (1H, d), δ6.11 (1H, d), δ6.95 (1H, t), δ7.34 (1H, s), δ7.76 (2H, d), δ7.84 (1H, t), δ8.21 (1H, s), δ8.23 (2H, d), δ11.55 (1H, s); $^{13}$C NMR (150 MHz DMSO-d6)=δ 68.07, 115.17, 117.18, 117.56, 123.27, 123.43, 127.23, 127.58, 129.74, 142.70, 146.20, 148.82, 153.24.

Example 3. Compound 3 ((5-bromo-7-chloro-1H-pyrrolo[2,3-c]pyridin-3-yl)(4-nitrophenyl)methanol

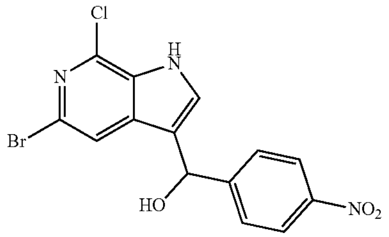 [SMILES: O=[N+]([O-])c1ccc(C(O)c2c[nH]c3c(Cl)nc(Br)cc23)cc1]

(5-bromo-7-chloro-1H-pyrrolo[2,3-c]pyridin-3-yl)(4-nitrophenyl)methanol was prepared in the similar manner to example 1, except that 4-nitrobenzaldehyde was added to 5-bromo-7chloro-6 azaindole in reaction solution A. ((5-bromo-7-chloro-1H-pyrrolo[2,3-c]pyridin-3-yl)(4-nitrophenyl)methanol was recovered as a cream colored solid with a recovered yield of 22.9 mg (60.12%); $R_f$=0.64 (9 DCM:1 MeOH); m.p.=238-239° C.; $^1$H NMR (600 MHz DMSO-d6)=δ6.15 (1H, d), δ6.23 (1H, d), δ7.62 (1H, s), δ7.75 (3H, m), δ8.20 (2H, d), δ12.25 (1H, s); $^{13}$C NMR (150 MHz DMSO-d6)=δ 67.14, 117.15, 119.88, 123.45, 125.46, 127.22, 129.64, 130.29, 132.20, 134.73, 146.40, 152.47.

Example 4. Compound 4 ((5-bromo-1H-pyrrolo[2,3-c]pyridin-3-yl)(4-nitrophenyl)methanol

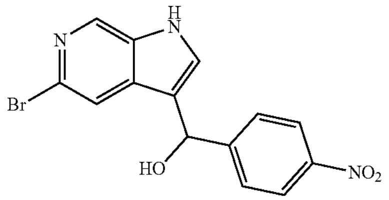

(5-bromo-1H-pyrrolo[2,3-c]pyridin-3-yl)(4-nitrophenyl)methanol was prepared in the similar manner to example 1, except that 4-nitrobenzaldehyde was added to 5-bromo-6 azaindole in reaction solution A. (5-bromo-1H-pyrrolo[2,3-c]pyridin-3-yl)(4-nitrophenyl)methanol was recovered as a cream coloured solid with a recovered yield of 12.6 mg (36.3%); $R_f$=0.30 (9 DCM:1 MeOH); $^1$H NMR (600 MHz DMSO-d6)=δ6.15 (1H, d), δ6.18 (1H, d), δ7.55 (1H, s), δ7.69 (1H, d), δ7.75 (2H, d), δ8.24 (2H, d), δ8.54 (1H, s), 11.76 (1H, s); $^{13}$C NMR (150 MHz DMSO-d6)=δ 67.27, 116.87, 118.09, 123.40, 127.21, 128.62, 129.46, 133.06, 133.37, 134.53, 146.33, 152.85.

Example 5. Compound 5 ((5-chloro-1H-pyrrolo[2,3-c]pyridin-3-yl)(4-nitrophenyl)methanol

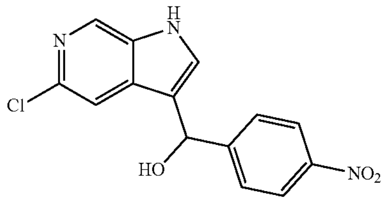 [SMILES: O=[N+]([O-])c1ccc(C(O)c2c[nH]c3cnc(Cl)cc23)cc1]

(5-chloro-1H-pyrrolo[2,3-c]pyridin-3-yl)(4-nitrophenyl) methanol was prepared in the similar manner to example 1, except that 4-nitrobenzaldehyde was added to 5-chloro-6 azaindole in reaction solution A. (5-chloro-1H-pyrrolo[2,3-c]pyridin-3-yl)(4-nitrophenyl)methanol was recovered as a white coloured solid with a recovered yield of 19.5 mg (64.4%); $R_f$=0.42 (9 DCM:1 MeOH); $^1$H NMR (600 MHz DMSO-d6)=δ6.15 (2H, m), δ7.49 (1H, s), δ7.52 (1H, d), δ7.75 (2H, d), δ8.21 (2H, d), δ8.53 (1H, s), 11.76 (1H, s); $^{13}$C NMR (150 MHz DMSO-d6)=δ 67.17, 113.05, 118.25, 123.47, 127.22, 129.65, 132.79, 133.11, 133.93, 138.66, 146.38, 152.96.

Example 6. Compound 6 ((5-fluoro-1H-pyrrolo[2,3-b]pyridin-3-yl)(4-nitrophenyl)methanol

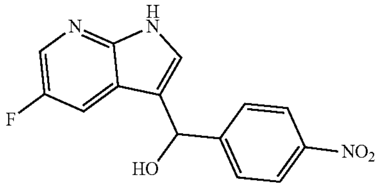 [SMILES: O=[N+]([O-])c1ccc(C(O)c2c[nH]c3ncc(F)cc23)cc1]

(5-fluoro-1H-pyrrolo[2,3-b]pyridin-3-yl)(4-nitrophenyl) methanol was prepared in the similar manner to example 1, except that 4-nitrobenzaldehyde was added to 5-fluoro-7-azaindole in reaction solution A. (5-fluoro-1H-pyrrolo[2,3-b]pyridin-3-yl)(4-nitrophenyl)methanol was recovered as an orange solid with a recovered yield of 16.1 mg (58.1%); $R_f$=0.63 (9 DCM:1 MeOH); m.p.=215-216° C.; $^1$H NMR (600 MHz DMSO-d6)=δ6.09 (2H, m), δ7.42 (1H, d), δ7.69 (1H, t), δ7.71 (2H, d), δ8.23 (3H, m), δ11.72 (1H, s); $^{13}$C NMR (150 MHz DMSO-d6)=δ 67.83, 112.93, 113.07, 117.48, 123.36, 125.95, 127.21, 130.81, 131.00, 145.63, 146.29, 152.95, 153.77, 155.35.

Example 7. Compound 7 ((5-chloro-1H-pyrrolo[2,3-b]pyridin-3-yl)(4-nitrophenyl)methanol

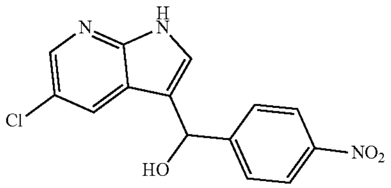 [SMILES: O=[N+]([O-])c1ccc(C(O)c2c[nH]c3ncc(Cl)cc23)cc1]

(5-chloro-1H-pyrrolo[2,3-b]pyridin-3-yl)(4-nitrophenyl) methanol was prepared in the similar manner to example 1, except that 4-nitrobenzaldehyde was added to 5-chloro-7-azaindole in reaction solution A. (5-chloro-1H-pyrrolo[2,3-b]pyridin-3-yl)(4-nitrophenyl)methanol was recovered as a pale white solid with a recovered yield of 28.9 mg (95.4%); $R_f$=0.51 (9 DCM:1 MeOH); m.p.=234° C.; $^1$H NMR (600 MHz DMSO-d6)=δ6.04 (1H, d), δ6.12 (1H, d), δ7.41 (1H, s), δ7.75 (2H, d), δ7.92 (1H, d), δ8.23 (3H, m), δ11.81 (1H, s); $^{13}$C NMR (150 MHz DMSO-d6)=δ 67.72, 117.21, 118.50, 122.03, 123.38, 125.56, 126.60, 127.21, 140.83, 146.32, 147.06, 152.86.

Example. Compound 8 ((7-chloro-1H-pyrrolo[2,3-c]pyridin-3-yl)(4-nitrophenyl)methanol

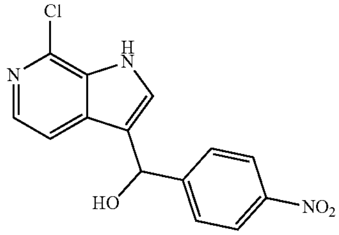 [SMILES: O=[N+]([O-])c1ccc(C(O)c2c[nH]c3c(Cl)nccc23)cc1]

(7-chloro-1H-pyrrolo[2,3-c]pyridin-3-yl)(4-nitrophenyl) methanol was prepared in the similar manner to example 1, except that 4-nitrobenzaldehyde was added to 7-chloro-6 azaindole in reaction solution A. (7-chloro-1H-pyrrolo[2,3-c]pyridin-3-yl)(4-nitrophenyl)methanol was recovered as a light brown solid with a recovered yield of 20.4 mg (67.32%); $R_f$=0.15 (9 DCM:1 MeOH); $^1$H NMR (400 MHz DMSO-d6)=δ6.20 (1H, s), δ7.50 (1H, d), δ7.59 (1H, d), δ7.79 (2H, d), δ8.24 (2H, d), δ12.02 (1H, s); $^{13}$C NMR (100 MHz DMSO-d6)=δ–67.74, 114.61, 120.13, 123.58, 127.47, 128.33, 130.07, 132.20, 132.20, 133.93, 137.12, 153.04.

Example 9. Compound 9 ((3-nitrophenyl)(1H-pyrrolo[2,3-c]pyridin-3-yl)methanol

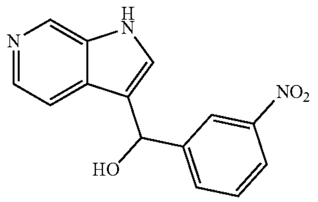 [SMILES: O=[N+]([O-])c1cccc(C(O)c2c[nH]c3cnccc23)c1]

(3-nitrophenyl)(1H-pyrrolo[2,3-c]pyridin-3-yl)methanol was prepared in the similar manner to example 1, except that 3-nitrobenzaldehyde was added to 6 azaindole in reaction solution A. (3-nitrophenyl)(1H-pyrrolo[2,3-c]pyridin-3-yl) methanol was recovered as a pale yellow solid with a recovered yield of 20.8 mg (77.29%); $R_f$=0.23 (9 DCM:1 MeOH); m.p.=142° C.; $^1$H NMR (600 MHz DMSO-d6) =δ6.10 (1H, s), δ6.12 (1H, s), δ7.42 (1H, d), δ7.51 (1H, d), δ7.62 (1H, t), δ7.89 (1H, d), δ8.04 (1H, d), δ8.11 (1H, t), δ8.33 (1H, d), δ8.75 (1H, d), δ11.54 (1H, s); $^{13}$C NMR (150 MHz DMSO-d6)=δ 67.42, 114.04, 118.34, 120.59, 121.68, 127.18, 129.55, 129.59, 132.97, 133.78, 134.58, 137.41, 147.72, 147.90.

Example 10. Compound 10 ((5-bromo-7-chloro-1H-pyrrolo[2,3-c]pyridin-3-yl)(3-nitrophenyl)methanol

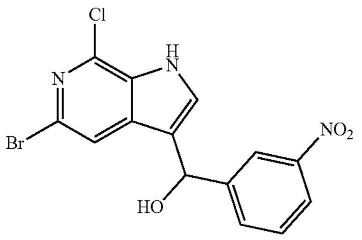 [SMILES: O=[N+]([O-])c1cccc(C(O)c2c[nH]c3c(Cl)nc(Br)cc23)c1]

(5-bromo-7-chloro-1H-pyrrolo[2,3-c]pyridin-3-yl)(3-nitrophenyl)methanol was prepared in the similar manner to example 1, except that 3-nitrobenzaldehyde was added to 5-bromo-7chloro-6 azaindole in reaction solution A. ((5-bromo-7-chloro-1H-pyrrolo[2,3-c]pyridin-3-yl)(3-nitrophenyl)methanol was recovered as a pale brown solid with a recovered yield of 18.4 mg (48.3%); $R_f$=0.42 (9 DCM:1 MeOH); m.p.=228° C.; $^1$H NMR (600 MHz DMSO-d6)= δ6.15 (1H, d), δ6.26 (1H, d), δ7.61 (2H, m), δ7.77 (1H, s), δ7.89 (1H, d), δ8.15 (1H, t), δ8.34 (1H, d), δ12.23 (1H, s); $^{13}$C NMR (150 MHz DMSO-d6)=δ 66.89, 117.15, 120.08, 120.62, 121.92, 125.45, 129.66, 129.75, 130.33, 133.78, 132.20, 132.83, 134.77, 147.15, 147.77.

Example 11. Compound 11 ((3-nitrophenyl)(1H-pyrrolo[2,3-b]pyridin-3-yl)methanol

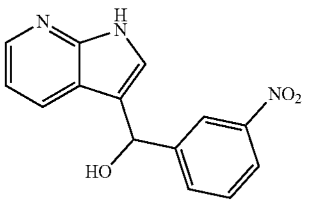 [SMILES: O=[N+]([O-])c1cccc(C(O)c2c[nH]c3ncccc23)c1]

(3-nitrophenyl)(1H-pyrrolo[2,3-b]pyridin-3-yl)methanol was prepared in the similar manner to example 1, except that 3-nitrobenzaldehyde was added to 7-azaindole in reaction solution A. (3-nitrophenyl)(1H-pyrrolo[2,3-b]pyridin-3-yl) methanol was recovered as a pale white solid with a recovered yield of 24.8 mg (92.2%); $R_f$=0.39 (9 DCM:1 MeOH); m.p.=202° C.

Example 12. Compound 12 ((5-chloro-1H-pyrrolo[2,3-b]pyridin-3-yl)(3-nitrophenyl)methanol

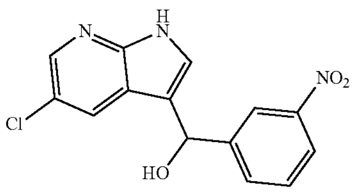 [SMILES: O=[N+]([O-])c1cccc(C(O)c2c[nH]c3ncc(Cl)cc23)c1]

(5-chloro-1H-pyrrolo[2,3-b]pyridin-3-yl)(3-nitrophenyl) methanol was prepared in the similar manner to example 1, except that 3-nitrobenzaldehyde was added to 5-chloro-7 azaindole in reaction solution A. The crude mixture was dried under reduced pressure and subjected to gravity column chromatography using a gradient elution of petroleum ether and ethyl acetate. (5-chloro-1H-pyrrolo[2,3-b]pyridin-3-yl)(3-nitrophenyl)methanol was recovered as a light brown solid with a recovered yield of 28.1 mg (92.7%); $R_f$=0.40 (9 DCM:1 MeOH (×2)); m.p.=155-156° C.; $^1$H NMR (600 MHz DMSO-d6)=δ6.12 (1H, d), δ6.19 (1H, d), δ7.42 (1H, d), δ7.63 (1H, t), δ7.89 (1H, d), δ7.92 (1H, d), δ8.13 (1H, t), δ8.13 (1H, s), δ8.33 (1H, s), δ11.82 (1H, s); $^{13}$C NMR (150 MHz DMSO-d6)=δ 67.50, 117.46, 118.61, 120.65, 121.87, 122.11, 125.68, 126.68, 129.74, 132.94, 140.90, 147.12, 147.51, 147.81.

Example 13. Compound 13 ((5-chloro-1H-pyrrolo[2,3-c]pyridin-3-yl)(3-nitrophenyl)methanol

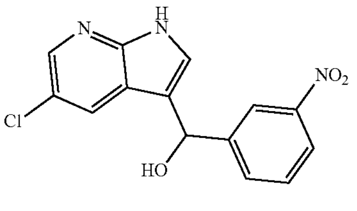 [SMILES: O=[N+]([O-])c1cccc(C(O)c2c[nH]c3ncc(Cl)cc23)c1]

(5-chloro-1H-pyrrolo[2,3-c]pyridin-3-yl)(3-nitrophenyl) methanol was prepared in the similar manner to example 1, except that 3-nitrobenzaldehyde was added to 5chloro-6-azaindole in reaction solution A. (5-chloro-1H-pyrrolo[2,3-c]pyridin-3-yl)(3-nitrophenyl)methanol was recovered as a white solid with a recovered yield of 15.3 mg (50.4%); $R_f$=0.43 (9 DCM:1 MeOH); m.p.=227-228° C.

Example 14. Compound 14 ((5-fluoro-1H-pyrrolo[2,3-b]pyridin-3-yl)(3-nitrophenyl)methanol

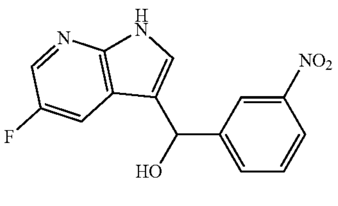 [SMILES: O=[N+]([O-])c1cccc(C(O)c2c[nH]c3ncc(F)cc23)c1]

(5-fluoro-1H-pyrrolo[2,3-b]pyridin-3-yl)(3-nitrophenyl) methanol was prepared in the similar manner to example 1, except that 3-nitrobenzaldehyde was added to 5-fluoro-7-azaindole in reaction solution A. (5-fluoro-1H-pyrrolo[2,3-b]pyridin-3-yl)(3-nitrophenyl)methanol was recovered as a white solid with a recovered yield of 11.2 mg (39.0%); $R_f$=0.46 (9 DCM:1 MeOH); m.p.=202° C.; $^1$H NMR (600 MHz DMSO-d6)=δ6.09 (2H, m), δ7.44 (1H, d), δ7.62 (1H, t), δ7.69 (1H, t), δ7.89 (1H, d), δ8.13 (1H, t), δ8.19 (1H, d), δ8.35 (1H, d), δ11.72 (1H, s); $^{13}$C NMR (150 MHz DMSO-d6)=δ 67.53, 112.91, 113.05, 117.61, 117.66, 117.68, 117.71, 120.57, 121.74, 125.99, 129.62, 130.81, 131.00, 132.87, 145.65, 147.55, 147.75, 153.77, 155.35.

Example 15. Compound 15 ((7-chloro-1H-pyrrolo [2,3-c]pyridin-3-yl)(3-nitrophenyl)methanol

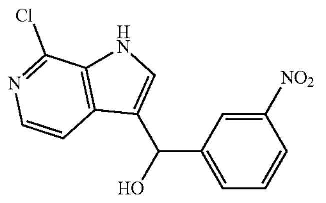 [SMILES: O=[N+]([O-])c1cccc(C(O)c2c[nH]c3c(Cl)nccc23)c1]

(7-chloro-1H-pyrrolo[2,3-c]pyridin-3-yl)(3-nitrophenyl) methanol was prepared in the similar manner to example 1, except that 3-nitrobenzaldehyde was added to 7-chloro-6-azaindole in reaction solution A. (7-chloro-1H-pyrrolo[2,3-c]pyridin-3-yl)(3-nitrophenyl)methanol was recovered as a brown solid with a recovered yield of 20.9 mg (69.0%); $R_f$=0.27 (9 DCM:1 MeOH); m.p.=133° C.

Example 16. Compound 16 ((4-bromophenyl)(1H-pyrrolo[2,3-c]pyridin-3-yl)methanol

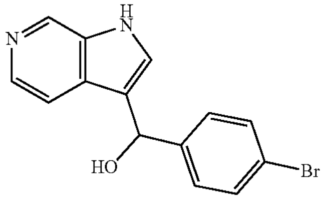 [SMILES: OC(c1ccc(Br)cc1)c1c[nH]c2cnccc12]

10 mmol (19.6 mg) of 6 azaindole was added to reaction solution A from example 1. The reaction was allowed to stir for 30 mins at 25° C. 15 mmol (27.6 mg) of 4-bromobenzaldehyde was added in a stepwise manner and allowed to stir continually for 48 h. The reaction progression was monitored periodically by thin layer chromatography and the reaction was stopped upon consumption of all the 6 azaindole. The reaction was quenched with 50 mL of a saturated sodium bicarbonate solution and then washed with an equivalent volume of EtOAc (×3). The organic phase was pooled and dried under over $Na_2SO_4$. The crude extract was then concentrated under reduced pressure and then subjected to gravity column chromatography, eluting with a isocratic solvent mixture of 80% DCM and 20% MeOH. 4-bromophenyl)(1H-pyrrolo[2,3-c]pyridin-3-yl)methanol was isolated as a brown solid with a recovered yield of 21.8 mg (64.9%); $R_f$=0.29 (9 DCM:1 MeOH); $^1$H NMR (600 MHz DMSO-d6)=δ5.80 (1H, d), δ5.94 (1H, d), 6.95 (1H, t), δ7.25 (1H, d), δ7.41 (2H, d), δ7.49 (2H, d), δ7.79 (1H, t), δ8.16 (1H, d), δ11.49 (1H, s); $^{13}$C NMR (150 MHz DMSO-d6)=δ 68.14, 115.03, 117.67, 117.92, 119.51, 123.02, 127.62, 128.47, 130.79, 142.56, 144.89, 148.83.

Example 17. Compound 17 ((5-bromo-1H-pyrrolo [2,3-c]pyridin-3-yl)(4-bromophenyl)methanol

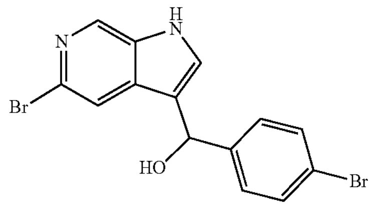 [SMILES: OC(c1ccc(Br)cc1)c1c[nH]c2cnc(Br)cc12]

(5-bromo-1H-pyrrolo[2,3-c]pyridin-3-yl)(4-bromophenyl)methanol (was synthesised in a similar manner to example 16, except that 4-bromobenzaldehyde was added to 5-bromo-6 azaindole. (5-bromo-1H-pyrrolo[2,3-c]pyridin-3-yl)(4-bromophenyl)methanol was isolated as a brown solid with a recovered yield of 34.1 mg (89.8%); $R_f$=0.32 (9 DCM:1 MeOH); $^1$H NMR (600 MHz DMSO-d6)=δ5.92 (1H, d), δ5.96 (1H, d), δ7.41 (2H, d), δ7.52 (1H, s), δ7.57 (2H, d), δ7.61 (1H, s), 11.66 (1H, s); $^{13}$C NMR (150 MHz DMSO-d6)=δ 67.40, 116.96, 118.81, 119.73, 128.43, 128.48, 129.16, 130.93, 133.14, 133.41, 134.43, 144.57.

Example 18. Compound 18 ((4-bromophenyl)(7-chloro-1H-pyrrolo[2,3-c]pyridin-3-yl)methanol

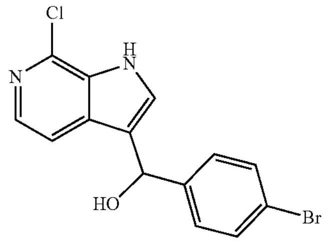 [SMILES: OC(c1ccc(Br)cc1)c1c[nH]c2c(Cl)nccc12]

(4-bromophenyl)(7-chloro-1H-pyrrolo[2,3-c]pyridin-3-yl)methanol was prepared in the similar manner to example 16, except that 4-bromobenzaldehyde was added to 7-chloro-6 azaindole in reaction solution A. (4-bromophenyl)(7-chloro-1H-pyrrolo[2,3-c]pyridin-3-yl)methanol was recovered as a brown viscous liquid with a recovered yield of 23.8 mg (70.2%); $R_f$=0.22 (7 Pet Ether:3 EtOAc); m.p.=liquid at room temperature; $^1$H NMR (400 MHz DMSO-d6)=δ5.03 (2H, s), δ7.47 (3H, m), δ7.52 (3H, m), δ7.85 (1H, d), δ11.89 (1H, s); $^{13}$C NMR (100 MHz DMSO-d6)=δ 67.72, 114.45, 119.80, 120.71, 127.80, 128.52, 129.92, 130.96, 132.11, 133.70, 136.81, 144.58.

Example 19. Compound 19 ((4-bromophenyl)(5-chloro-1H-pyrrolo[2,3-b]pyridin-3-yl)methanol

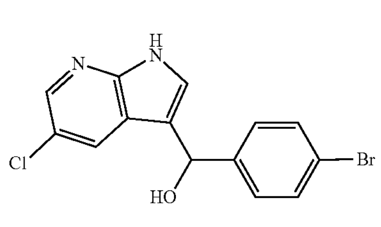 [SMILES: OC(c1ccc(Br)cc1)c1c[nH]c2ncc(Cl)cc12]

(4-bromophenyl)(5-chloro-1H-pyrrolo[2,3-b]pyridin-3-yl)methanol was prepared in the similar manner to example 7, except that 4-bromobenzaldehyde was added to 5-chloro-7-azaindole in reaction solution A. (4-bromophenyl)(5-chloro-1H-pyrrolo[2,3-b]pyridin-3-yl)methanol was recovered as a pale brown solid with a recovered yield of 17.9 mg (51.6%); $R_f$=0.41 (9 DCM:1 MeOH); $^{13}$C NMR (150 MHz DMSO-d6)=δ 67.80, 117.91, 118.59, 119.68, 121.86, 125.20, 126.63, 128.42, 130.90, 140.66, 144.57, 147.08.

Example 20. Compound 20 ((4-bromophenyl)(5-chloro-1H-pyrrolo[2,3-c]pyridin-3-yl)methanol

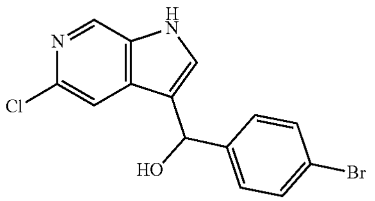 [SMILES: OC(c1ccc(Br)cc1)c1c[nH]c2cnc(Cl)cc12]

(4-bromophenyl)(5-chloro-1H-pyrrolo[2,3-c]pyridin-3-yl)methanol was synthesised in a similar manner to example 7, except that 4-bromobenzaldehyde was added to 5-chloro-6-azaindole. 4-bromophenyl)(5-chloro-1H-pyrrolo[2,3-c]pyridin-3-yl)methanol was isolated as a brown solid with a recovered yield of 21.8 mg (64.9%); $R_f$=0.3 (9 DCM:1 MeOH; $^{1}$H NMR (600 MHz DMSO-d6)=δ6.49 (2H, s), δ7.51 (1H, d), δ7.60 (2H, d), δ7.70 (2H, d), δ8.56 (1H, s), δ11.80 (1H, s); $^{13}$C NMR (150 MHz DMSO-d6)=δ 67.44, 113.16, 118.93, 119.73, 129.39, 130.92, 132.56, 132.91, 133.11, 133.76, 138.38, 144.59.

Example 21. Compound 21 (4-((5-chloro-1H-pyrrolo[2,3-c]pyridin-3-yl)(hydroxy)methyl)phenol

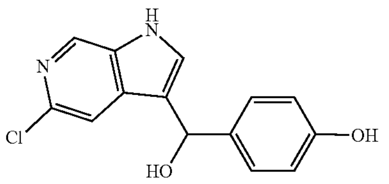 [SMILES: Oc1ccc(C(O)c2c[nH]c3cnc(Cl)cc23)cc1]

4-((5-chloro-1H-pyrrolo[2,3-c]pyridin-3-yl)(hydroxy)methyl)phenol was prepared in the similar manner to example 1, except that 4-hydroxybenzaldehyde was added to 5-chloro-6-azaindole in reaction solution A. The reaction was heated at 150° C. continually for 24 hrs on a hotplate with periodic re-application of solution A. The reaction was monitored via TLC analysis. The crude mixture was dried under reduced pressure and then subjected to gravity column chromatography using a gradient elution of DCM and MeOH. 4-((5-chloro-1H-pyrrolo[2,3-c]pyridin-3-yl)(hydroxy)methyl)phenol was recovered as a red solid with a recovered yield of 20.9 mg (76.3%); $R_f$=0.52 (9 DCM:1 MeOH); $^{1}$H NMR (600 MHz DMSO-d6)=δ6.67 (2H, d), δ7.01 (2H, d), δ7.21 (2H, d), δ7.21 (1H, s), δ7.76 (1H, s), δ10.76 (1H, s), δ11.58 (1H, s); $^{13}$C NMR (150 MHz DMSO-d6)=δ 67.82, 113.31, 116.10, 117.59, 128.51, 130.24, 132.76, 133.93, 135.01, 139.75, 157.41.

Example 22. Compound 22 (4-((5-fluoro-1H-pyrrolo[2,3-b]pyridin-3-yl)(hydroxy)methyl)phenol

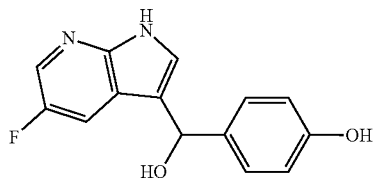 [SMILES: Oc1ccc(C(O)c2c[nH]c3ncc(F)cc23)cc1]

4-((5-fluoro-1H-pyrrolo[2,3-b]pyridin-3-yl)(hydroxy)methyl)phenol was prepared in the similar manner to example 21, except that 4-hydroxybenzaldehyde was added to 5-fluoro-7-azaindole in reaction solution A. The reaction was heated at 150° C. continually for 24 hrs on a hotplate with periodic re-application of solution A. The reaction was monitored via TLC analysis. The crude mixture was dried under reduced pressure and then subjected to gravity column chromatography using a gradient elution of DCM and MeOH. 4-((5-fluoro-1H-pyrrolo[2,3-b]pyridin-3-yl)(hydroxy)methyl)phenol was recovered as a pale red with a recovered yield of 12.5 mg (48.3%); $R_f$=0.40 (9 DCM:1 MeOH); $^{13}$C NMR (150 MHz DMSO-d6)=δ 67.79, 110.54, 116.32, 116.76, 117.73, 128.5, 130.31, 132.24, 132.56, 133.97, 139.75, 157.41, 164.14.

Example 23. Compound 23 (4-(hydroxy(1H-pyrrolo[2,3-b]pyridin-3-yl)methyl)phenol

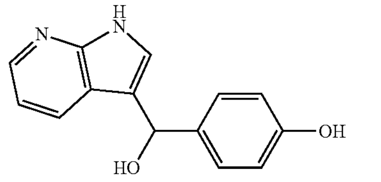 [SMILES: Oc1ccc(C(O)c2c[nH]c3ncccc23)cc1]

4-(hydroxy(1H-pyrrolo[2,3-b]pyridin-3-yl)methyl)phenol was prepared in the similar manner to example 21, except that 4-hydroxybenzaldehyde was added to 7-azaindole in reaction solution A. The reaction was heated at 150° C. continually for 24 hrs on a hotplate with periodic re-application of solution A. The reaction was monitored via TLC analysis. The crude mixture was dried under reduced pressure and then subjected to gravity column chromatography using a gradient elution of DCM and MeOH. 4-(hydroxy(1H-pyrrolo[2,3-b]pyridin-3-yl)methyl)phenol was recovered as a pink solid with a recovered yield of 20.5 mg (85.1%); $R_f$=0.39 (9 DCM:1 MeOH (×2)); $^{1}$H NMR (600 MHz DMSO-d6)=δ5.75 (1H, s), δ5.84 (1H, s), δ6.69 (2H, d), δ6.87 (1H, d), δ6.98 (2H, d), δ7.01 (1H, d), δ7.65 (1H, d), δ8.16 (1H, d), δ9.29 (1H, s), δ9.67 (1H, s), δ10.74 (1H, s).

Example 24. Compound 24 ((2-nitrophenyl)(1H-pyrrolo[2,3-c]pyridin-3-yl)methanol

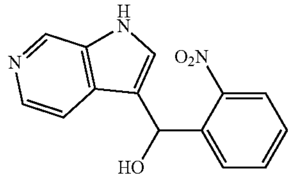 [SMILES: O=[N+]([O-])c1ccccc1C(O)c1c[nH]c2cnccc12]

(2-nitrophenyl)(1H-pyrrolo[2,3-c]pyridin-3-yl)methanol was prepared in the similar manner to example 1, except that 2-nitrobenzaldehyde was added to 6-azaindole in reaction solution A. (2-nitrophenyl)(1H-pyrrolo[2,3-c]pyridin-3-yl) methanol was recovered as a dark yellow solid with a recovered yield of 26.4 mg (97.8%); $R_f$=0.15 (9 DCM:1 MeOH); m.p.=137° C.; $^1$H NMR (600 MHz DMSO-d6)=δ6.09 (1H, s), 66.51 (1H, s), δ7.23 (1H, d), δ7.39 (1H, t), δ7.52 (1H, t), δ7.76 (1H, t), δ7.87 (1H, d), δ8.02 (2H, m), δ8.71 (1H, s), δ11.51 (1H, s); $^{13}$C NMR (150 MHz DMSO-d6)=δ 63.44, 113.86, 116.95, 124.00, 127.51, 128.23, 128.43, 129.96, 133.06, 133.57, 134.59, 137.48, 139.08, 147.96.

Example 25. Compound 25 ((2-nitrophenyl)(1H-pyrrolo[2,3-b]pyridin-3-yl)methanol

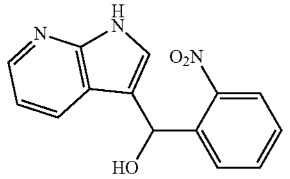 [SMILES: O=[N+]([O-])c1ccccc1C(O)c1c[nH]c2ncccc12]

(2-Nitrophenyl)(1H-pyrrolo[2,3-b]pyridin-3-yl)methanol was prepared in the similar manner to Example 1, except that 2-nitrobenzaldehyde was added to 7-azaindole in reaction solution A. (2-nitrophenyl)(1H-pyrrolo[2,3-c]pyridin-3-yl)methanol was recovered as a pale yellow solid with a recovered yield of 21.4 mg (79.6%); $R_f$=0.38 (9 DCM:1 MeOH); m.p.=179-180° C.; $^1$H NMR (600 MHz DMSO-d6)=δ6.05 (1H, s), δ6.49 (1H, s), δ6.99 (1H, t), δ7.01 (1H, s), δ7.52 (1H, t), δ7.75 (1H, t), δ7.81 (1H, t), δ7.95 (1H, d), δ11.51 (1H, s); $^{13}$C NMR (150 MHz DMSO-d6)=δ 63.76, 115.32, 116.02, 118.00, 123.71, 123.96, 127.39, 128.20, 128.40, 133.00, 138.94, 142.76, 148.01, 148.62.

Example 26. Compound 26 ((5-bromo-1H-pyrrolo[2,3-c]pyridin-3-yl)(3,4-dimethoxyphenyl)methanol

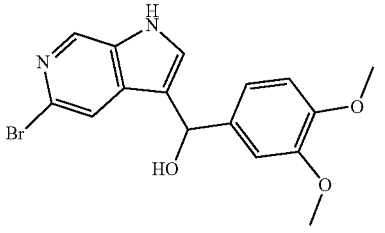 [SMILES: COc1ccc(C(O)c2c[nH]c3cnc(Br)cc23)cc1OC]

(5-Bromo-1H-pyrrolo[2,3-c]pyridin-3-yl)(3,4-dimethoxyphenyl)methanol was prepared in the similar manner to example 21, except that 3,4-Dimethoxybenzaldehyde was added to 5Br-6-azaindole in reaction solution A. The reaction was heated at 150° C. continually for 24 hrs on a hotplate with periodic re-application of solution A. The reaction was monitored via TLC analysis. The crude mixture was dried under reduced pressure and then subjected to gravity column chromatography using a gradient elution of DCM and MeOH. (5-bromo-1H-pyrrolo[2,3-c]pyridin-3-yl)(3,4-dimethoxyphenyl)methanol was recovered as a orange solid with a recovered yield of 10.2 mg (28.2%); $R_f$=0.51 (9 DCM:1 MeOH); $^1$H NMR (600 MHz DMSO-d6)=δ3.65 (3H, s), δ3.72 (3H, s), δ5.74 (1H, d), δ5.85 (1H, d), δ6.74 (1H, d), δ6.92 (1H, s), δ7.05 (1H, d), δ7.05 (1H, d), δ7.24 (1H, d), δ7.56 (1H, s), δ8.51 (1H, s), δ11.61 (1H, s); $^{13}$C NMR (150 MHz DMSO-d6)=δ 55.43, 67.96, 110.21, 111.39, 116.55, 117.15, 117.41, 128.35, 128.97, 133.33, 133.44, 134.12, 134.34, 134.50, 147.65, 148.44.

Example 27. Compound 27 ((3-bromophenyl)(1H-pyrrolo[2,3-c]pyridin-3-yl)methanol

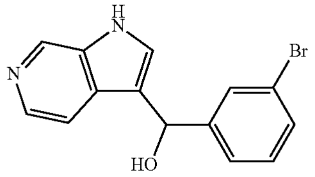 [SMILES: OC(c1cccc(Br)c1)c1c[nH]c2cnccc12]

(3-bromophenyl)(1H-pyrrolo[2,3-c]pyridin-3-yl)methanol was prepared in the similar manner to example 21, except that 4-bromobenzaldehyde was added to 6-azaindole in reaction solution A. The reaction was heated at 150° C. continually for 24 hrs on a hotplate with periodic re-application of solution A. The reaction was monitored via TLC analysis. The crude mixture was dried under reduced pressure and then subjected to gravity column chromatography using a gradient elution of DCM and MeOH. 3-bromophenyl)(1H-pyrrolo[2,3-c]pyridin-3-yl)methanol was recovered as a yellow liquid with a recovered yield of 23.5 mg (77.8%); $R_f$=0.11 (9 DCM:1 MeOH (×2)); Sample is a mixture of (3-bromophenyl)(1H-pyrrolo[2,3-c]pyridin-3-yl) methanol and 3,3'-((3-bromophenyl)methylene)bis(1H-pyrrolo[2,3-c]pyridine; $R_f$=0.12 (9 DCM:1 MeOH); $^1$H NMR (600 MHz DMSO-d6)=δ5.61 (1H, d), δ5.64 (1H, d), 6.52 (1H, s), δ7.25 (1H, d), δ7.32 (1H, t), δ7.38 (1H, t), δ7.44 (1H, d), δ8.43 (1H, d), δ8.92 (1H, d), δ11.51 (1H, s); $^{13}$C NMR (150 MHz DMSO-d6)=δ 77.47, 112.01, 113.92, 115.05, 121.58, 122.06, 125.98, 129.62, 129.81, 130.45, 133.49, 134.11, 137.48, 145.09.

Example 28. Compound 28 (3-((7-chloro-1H-pyrrolo[2,3-c]pyridin-3-yl)(hydroxy)methyl)benzaldehyde

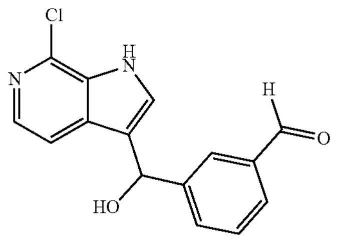 [SMILES: O=Cc1cccc(C(O)c2c[nH]c3c(Cl)nccc23)c1]

3-((7-chloro-1H-pyrrolo[2,3-c]pyridin-3-yl)(hydroxy)methyl)benzaldehyde was prepared in the similar manner to example 16, except that isophthalaldehyde was added to 7-chloro-6 azaindole in reaction solution A. (3-((7-chloro-1H-pyrrolo[2,3-c]pyridin-3-yl)(hydroxy)methyl)benzaldehyde was recovered as a orange liquid with a recovered yield of 25.9 mg (90.5%); $R_f$=0.15 (9 DCM:1 MeOH); the product is a liquid at room temperature; $^1$H NMR (400 MHz DMSO-d6)=δ6.10 (2H, m), δ7.48 (1H, d), δ7.55 (2H, m), δ7.84 (3H, m), δ8.05 (1H, s), δ10.04 (1H, s), δ11.91 (1H, s); $^{13}$C NMR (100 MHz DMSO-d6)=δ−67.68, 114.41, 120.59, 126.74, 127.87, 128.31, 128.95, 129.83, 132.03, 132.37, 133.63, 136.12, 136.79, 146.31, 193.31.

Example 29. Compound 29 ((3-aminophenyl)(1H-pyrrolo[2,3-c]pyridin-3-yl)methanol

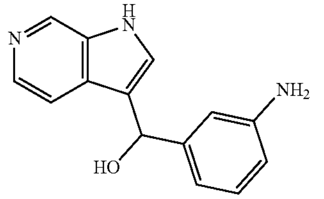 [SMILES: Nc1cccc(C(O)c2c[nH]c3cnccc23)c1]

(3-Aminophenyl)(1H-pyrrolo[2,3-c]pyridin-3-yl)methanol was prepared via the catalytic reduction of (3-nitrophenyl)(1H-pyrrolo[2,3-c]pyridin-3-yl)methanol. 50 mg of (3-nitrophenyl)(1H-pyrrolo[2,3-c]pyridin-3-yl)methanol was added to 10 mL MeOH in the reaction vessel. The vessel was evacuated, and a catalytic amount of Palladium was added. $H_2$ gas was added to the vessel and the reaction allowed to proceed for 2 hours at room temperature and pressure. The reaction was then filtered through celite and the product was dried under reduced pressure to afford compound 29; $R_f$=0.21 (9 DCM:1 MeOH (×2)); $^1$H NMR (600 MHz DMSO-d6)=δ6.15 (2H, s), δ7.44 (1H, d), δ7.49 (1H, d), δ7.59 (1H, t), δ7.89 (1H, d), δ8.01 (1H, d), δ8.14 (1H, t), δ8.33 (1H, s), δ8.74 (1H, s), δ11.59 (1H, s); $^{13}$C NMR (150 MHz DMSO-d6)=δ 67.47, 114.14, 118.43, 120.64, 121.72, 127.37, 129.62, 129.68, 133.00, 133.80, 134.53, 137.33, 147.77, 147.91.

Example 30. Compound 30 ((4-aminophenyl)(1H-pyrrolo[2,3-c]pyridin-3-yl)methanol

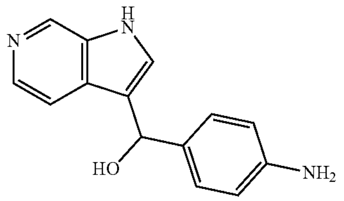 [SMILES: Nc1ccc(C(O)c2c[nH]c3cnccc23)cc1]

(4-aminophenyl)(1H-pyrrolo[2,3-c]pyridin-3-yl)methanol was in a similar manner to example 30 except that 50 mg of (4-nitrophenyl)(1H-pyrrolo[2,3-c]pyridin-3-yl)methanol was reduced via Pd/C hydrogenation to afford compound 30; $R_f$=0.15 (9 DCM:1 MeOH (×2)); $^1$H NMR (600 MHz DMSO-d6)=δ3.61 (2H, s), δ4.98 (1H, d), 5.03 (1H, d), δ5.25 (2H, d), δ5.56 (1H, d), δ5.69 (2H, d), δ6.23, δ9.09 (1H, s); $^{13}$C NMR (150 MHz DMSO-d6)=δ 67.71, 114.13, 118.22, 123.34, 127.29, 129.63, 133.76, 134.52, 137.30, 146.28, 153.27.

Example 31. Compound 31 (4-((1H-pyrrolo[2,3-c]pyridin-3-yl)(vinyloxy)methyl)aniline

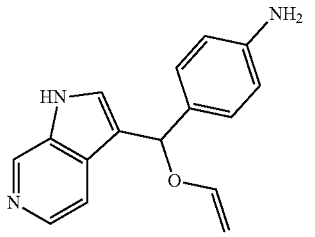 [SMILES: C=COC(c1ccc(N)cc1)c1c[nH]c2cnccc12]

4-((1H-pyrrolo[2,3-c]pyridin-3-yl)(vinyloxy)methyl)aniline was created by reacting 10 mmol of 4-aminophenyl)(1H-pyrrolo[2,3-c]pyridin-3-yl)methanol (example 30) with 15 mmol of bromoethane in 10 mL DMF with 20 mmol NaH under an inert atmosphere. The reaction was stirred for 18 h and then quenched in 2 volumes of EtOAc and washed with 1 volume of saturated $NaHCO_3$ and then washed with water. The organic phase was collected and dried under reduced pressure; $R_f$=0.56 (9 DCM:1 MeOH (×2)); $^1$H NMR (600 MHz DMSO-d6)=δ4.01 (1H, d), δ4.18 (1H, d), 6.03 (1H, s), δ6.49 (1H, d), δ5.59 (1H, s), δ7.35 (1H, t), δ7.59 (2H, d), δ8.23 (2H, d), δ8.41 (1H, d), δ8.59 (1H, d), δ11.57 (1H, s); $^{13}$C NMR (150 MHz DMSO-d6)=δ 79.01, 87.12, 114.21, 117.78, 118.29, 124.54, 128.32, 130.20, 132.79, 144.25, 144.47, 146.82, 152.44, 153.03.

Example 32. Compound 32 (4-((allyloxy)(1H-pyrrolo[2,3-c]pyridin-3-yl)methyl)aniline

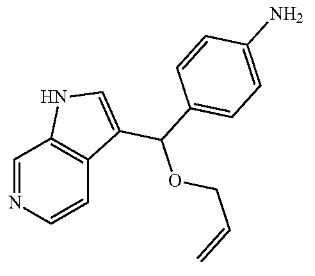 [SMILES: C=CCOC(c1ccc(N)cc1)c1c[nH]c2cnccc12]

4-((allyloxy)(1H-pyrrolo[2,3-c]pyridin-3-yl)methyl)aniline was created by in a similar manner to example 31 with the exception that 4-aminophenyl)(1H-pyrrolo[2,3-c]pyridin-3-yl)methanol was reacted with 3-bromoprop-1-ene. The reaction was stirred for 18 h and then quenched in 2 volumes of EtOAc and washed with 1 volume of saturated $NaHCO_3$ and then washed with water. The organic phase was collected and dried under reduced pressure; $R_f$=0.59 (9 DCM:1 MeOH); $^1$H NMR (600 MHz DMSO-d6)=δ4.07 (1H, d), δ5.18 (1H, d), 5.38 (1H, d), δ5.96 (1H, s), δ6.07 (1H, m), δ6.62 (1H, s), δ7.38 (1H, d), δ7.52 (2H, d), δ8.21 (2H, d), δ8.45 (1H, d), δ8.73 (1H, d), δ11.54 (1H, s).

Example 33. Compound 33 (4-((pyridin-4-ylamino)(1H-pyrrolo[2,3-b]pyridin-3-yl)methyl)phenol

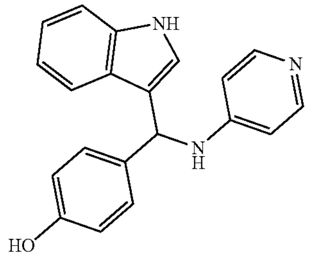 [SMILES: Oc1ccc(C(Nc2ccncc2)c2c[nH]c3ccccc23)cc1]

10 mmol each of 7-azaindole, 4hydroxybenzaldehyde and 4-aminopyridine was added to 10 mL DCE (dichloroethane). 5 mmol of p-Toluenesulfonic acid was added to the reaction mixture and then the reaction was stirred at 60° C. for 24 h. The reaction was dried under reduced pressure and the mixture subjected to column chromatography using DCM/MeOH; $R_f$=0.44 (7 Pet ether:3 EtOAC); $^1$H NMR (600 MHz DMSO-d6)=δ5.11 (1H, s), δ5.55 (1H, s), 6.52 (1H, s), δ6.69 (2H, d), δ6.98-7.05 (4H, m), δ7.38 (1H, d), δ8.39 (1H, t), δ8.49 (2H, d), δ8.56 (1H, d), δ9.12 (1H, s), δ11.51 (1H, s).

Example 34. Compound 34 (4-(bis(1H-pyrrolo[2,3-c]pyridin-3-yl)methyl)phenol) (SP-6azaBIM 136

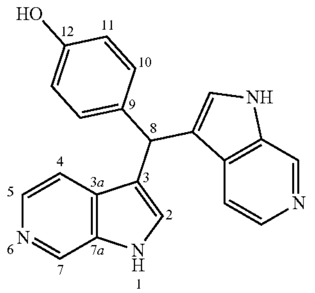 [SMILES: Oc1ccc(C(c2c[nH]c3cnccc23)c2c[nH]c3cnccc23)cc1]

4 mmol (2.36 mg) 6-azaindole was added to a solution of 15 mmol (10.36 mg) $K_2CO_3$ in 5 mL $MeOH/H_2O$ and stirred for 30 mins. 0.20 mmol (1.22 mg) of 4-hydroxybenzaldehyde was then added in a stepwise manner (~0.3 mg every 6 hours for the first 24 h) and the reaction allowed to proceed for 48 h. The resultant reaction was evaporated under reduced pressure and the residue was redissolved in methanol and filtered to remove residual $K_2CO_3$. To retrieve intermediate 3 (4-(hydroxy(1H-pyrrolo[2,3-c]pyridin-3-yl)methyl)phenol), the filtrate was evaporated under reduced pressure and subjected to gravity column chromatography eluting with a isocratic solvent system of 10% MeOH and 90% DCM. Resulting fractions were subsequently analysed by thin layer chromatography (TLC) on silica gel plates in an 7:3 ratio of PE/EtOAc (×4) mobile phase and fractions containing the product were combined.

2.4 mg of 4-(hydroxy(1H-pyrrolo[2,3-c]pyridin-3-yl)methyl)phenol was then added to 5 mL of the $K_2CO_3/MeOH/H_2O$ solution as described earlier and microwaved for 30 mins. 1.18 mg of 6-azaindole was added in stepwise manner during the first 15 mins of microwave irradiation. Upon completion of the reaction the sample was dried, dissolved in MeOH and filtered again. To obtain purified active compound, the filtrate was subjected to gravity column chromatography, eluting with a gradient solvent system of dichloromethane (DCM) and methanol (MeOH) varying from 0% to 100% MeOH. Upon drying pale yellow crystals were observed. These were then washed repeatedly with ice cold acetone; $R_f$=0.05 (9 DCM:1 MeOH (×2)); $^1$H NMR (400 MHz DMSO-d6)=δ5.98 (1H, s), δ7.42 (6H, m), δ7.51 (2H, d), δ8.11 (2H, d), δ8.80 (2H, s), δ10.04 (1H, s), δ11.77 (2H, s); $^{13}$C NMR (100 MHz DMSO-d6)=δ 30.72, 133.86, 115.04, 118.03, 127.40, 129.12, 130.61, 133.86, 134.31, 134.53, 137.09, 155.64.

To prepare SP-6azaBIM 136 for in vitro and in vivo testing, the HCl salt of the compound was created by dissolving the crystals in excess acetone and HCl gas slowly bubbled through the solution until the compound precipitated out. The salt was then allowed to dry and then stored at 4° C. until needed for testing. The HSQC data of compound 34 is shown in Table 1 (see below):

TABLE 1

| | HSQC | |
|---|---|---|
| Position | $^{\delta}$H | $^{\delta}$C |
| 1 | 11.12 (brs, 2H) | — |
| 2 | 7.48 (dd, 2H) | 124.88 |

TABLE 1-continued

| | HSQC | |
|---|---|---|
| Position | $^{\delta}H$ | $^{\delta}C$ |
| 3 | — | 116.58 |
| 3a | — | 133.28 |
| 4 | 7.79 (d, 2H) | 113.42 |
| 5 | 8.63 (d, 2H) | 140.06 |
| 6 | — | — |
| 7 | 8.76 (s, 2H) | 135.53 |
| 7a | — | 133.03 |
| 8 | 6.64 (s, 1H) | 41.71 |
| 9 | — | 135.17 |
| 10 | 7.03 (d, 2H) | 131.09 |
| 11 | 6.77 (d, 2H) | 115.78 |
| 12 | — | 156.14 |
| C12—OH | 8.36 (brs, 1H) | — |

Example 35. Compound 35 (3,3'-((4-bromophenyl) methylene)bis(1H-pyrrolo[2,3-c]pyridine) (SP-6azaBIM 125

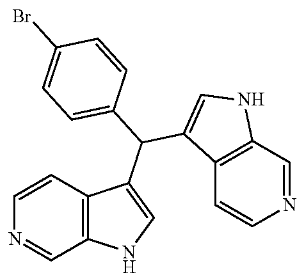 [SMILES: Brc1ccc(C(c2c[nH]c3cnccc23)c2c[nH]c3cnccc23)cc1]

Synthesis of SP-6azaBIM 125 followed the same protocol as with SP-6azaBIM 136. Isolation was also performed in a similar manner with the exception that the elution of the fractions during gravity column chromatography was done using a gradient of petroleum ether and ethyl acetate varying from 0% ethyl acetate to 100% ethyl acetate. (3,3'-((4-bromophenyl)methylene)bis(1H-pyrrolo[2,3-c]pyridine) was recovered as a white solid with a recovered yield of 15.5 mg (38.5%); $R_f$=0.23 (9 DCM:1 MeOH (×2)); $^{1}$H NMR (400 MHz DMSO-d6)=δ5.98 (1H, s), δ7.42 (6H, m), δ7.51 (2H, d), δ8.11 (2H, d), δ8.80 (2H, s), δ10.04 (1H, s), δ11.77 (2H, s). Both crystallization and salt formation also was the same.

Example 36. Compound 36 (3,3'-((3-nitrophenyl) methylene)bis(1H-pyrrolo[2,3-c]pyridine

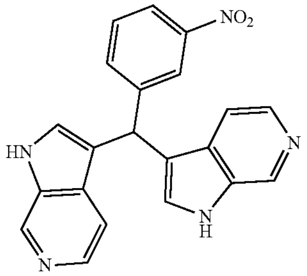 [SMILES: O=[N+]([O-])c1cccc(C(c2c[nH]c3cnccc23)c2c[nH]c3cnccc23)c1]

10 mmol (26.9 mg) of (3-nitrophenyl)(1H-pyrrolo[2,3-c] pyridin-3-yl)methanol (Example 9) was added to 10 mL of reaction solution A and allowed to stir for 10 mins to dissolve the compound. 10 mmol of 6 azaindole was then added to the reaction vessel and the mixture subjected to microwave irradiation at 1500 watts for 30 mins under reflux conditions. The reaction mixture was then allowed dry under convection heat to remove all the liquid from the reaction. The crude sample mixture was then subjected to gravity column chromatography using a gradient elution of DCM and methanol. 3,3'-((3-nitrophenyl)methylene)bis(1H-pyrrolo[2,3-c]pyridine) was isolated as a pale white solid with a recovered yield of 28.1 mg (76.10%); $R_f$=0.20 (9 DCM:1 MeOH (×2)); $^{1}$H NMR (600 MHz DMSO-d6)=δ6.12 (1H, s), δ7.21 (4H, m), δ7.60 (1H, t), δ7.82 (1H, t), δ7.99 (2H, d), δ8.10 (1H, d), δ8.18 (1H, d), δ8.74 (2H, d), δ11.5 (2H, s).

Example 37. Compound 37 (4-(bis(5-chloro-1H-pyrrolo[2,3-c]pyridin-3-yl)methyl)phenol) (SP-6azaBIM 136-5Cl

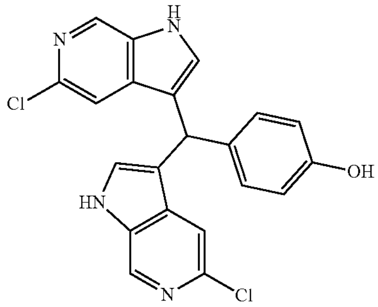 [SMILES: Oc1ccc(C(c2c[nH]c3cnc(Cl)cc23)c2c[nH]c3cnc(Cl)cc23)cc1]

4-(bis(5-chloro-1H-pyrrolo[2,3-b]pyridin-3-yl)methyl) phenol was synthesised in a similar manner to example 36, except that 4-hydroxybenzaldehyde was added to 5-chloro-7-azaindole. 4-(bis(5-chloro-1H-pyrrolo[2,3-b]pyridin-3-yl) methyl)phenol was isolated as a orange solid with a recovered yield of 21.8 mg (64.9%); $R_f$=0.29 (9 DCM:1 MeOH); $^{1}$H NMR (600 MHz DMSO-d6)=δ5.32 (1H, s), δ6.52 (2H, s), δ6.69 (2H, d), δ6.92 (2H, d), δ7.72 (2H, s), δ8.72 (2H, d), δ8.18 (1H, d), δ8.74 (2H, d), δ11.5 (2H, s); $^{13}$C NMR (150 MHz DMSO-d6)=δ 54.18, 113.38, 115.61, 116.29, 116.99, 130.24, 130.73, 132.72, 135.03, 134.53, 137.09, 155.64.

Example 38. Compound 38 (3-((5-bromo-1H-indol-3-yl)(3-nitrophenyl)methyl)-1H-pyrrolo[2,3-c]pyridine

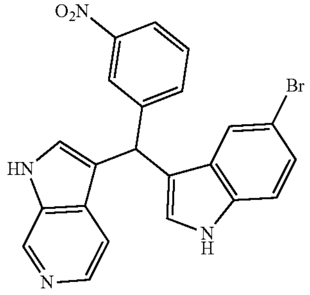 [SMILES: O=[N+]([O-])c1cccc(C(c2c[nH]c3cnccc23)c2c[nH]c3ccc(Br)cc23)c1]

3-((5-bromo-1H-indol-3-yl)(3-nitrophenyl)methyl)-1H-pyrrolo[2,3-c]pyridine was synthesised in a similar manner to example 36, except that 5-bromoindole was added to (3-nitrophenyl)(1H-pyrrolo[2,3-c]pyridin-3-yl)methanol; $R_f$=0.59 (9 DCM:1 MeOH); $^1$H NMR (600 MHz DMSO-d6)=δ5.57 (1H, s), δ6.55 (1H, s), δ6.61 (1H, s), δ7.36-7.39 (3H, m), δ7.54 (1H, d), δ7.59 (1H, t), δ7.85 (1H, s), δ8.09-8.13 (2H, m), δ8.43 (1H, d), δ8.85 (1H, s), δ10.72 (1H, s), 11.23 (1H, s).

The compounds in Table 2 below were prepared by using Scheme 1 or in an analogous fashion to that described for Compounds 34-38.

TABLE 2

| Compound No. | Compound name | Chemical name | Structure |
|---|---|---|---|
| | | SP-6azaBIM 136 series | |
| 39 | SP-6azaBIM 136-7C1 | 4-(bis(7-chloro-1H-pyrrolo[2,3-c]pyridin-3-yl)methyl)phenol | 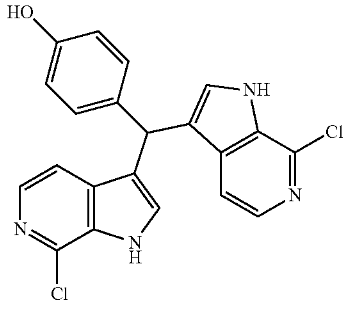 [SMILES: Oc1ccc(C(c2c[nH]c3c(Cl)nccc23)c2c[nH]c3c(Cl)nccc23)cc1] |
| 40 | SP-6azaBIM 136-5Br | 4-(bis(5-bromo-1H-pyrrolo[2,3-c]pyridin-3-yl)methyl)phenol | 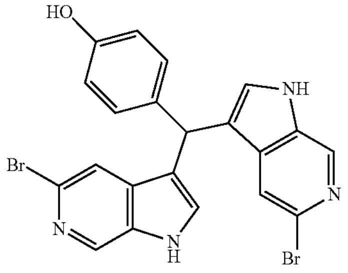 [SMILES: Oc1ccc(C(c2c[nH]c3cnc(Br)cc23)c2c[nH]c3cnc(Br)cc23)cc1] |
| 41 | SP-6azaBIM 136-7Br | 4-(bis(7-bromo-1H-pyrrolo[2,3-c]pyridin-3-yl)methyl)phenol | 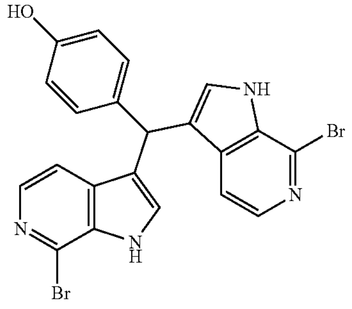 [SMILES: Oc1ccc(C(c2c[nH]c3c(Br)nccc23)c2c[nH]c3c(Br)nccc23)cc1] |
| 42 | SP-6azaBIM 136-7OMe | 4-(bis(7-methoxy-1H-pyrrolo[2,3-c]pyridin-3-yl)methyl)phenol | 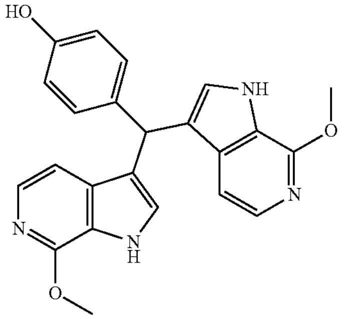 [SMILES: COc1nccc2c(C(c3ccc(O)cc3)c3c[nH]c4c(OC)nccc34)c[nH]c12] |

TABLE 2-continued

| Compound No. | Compound name | Chemical name | Structure |
|---|---|---|---|
| 43 | SP-6azaBIM 136-5NO | 4-(bis(5-nitro-1H-pyrrolo[2,3-c]pyridin-3-yl)methyl)phenol | 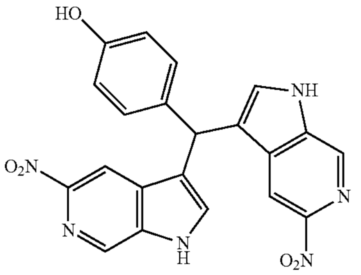 [SMILES: O=[N+]([O-])c1cc2c(C(c3ccc(O)cc3)c3c[nH]c4cnc([N+](=O)[O-])cc34)c[nH]c2cn1] |
| 44 | SP-6azaBIM 136-5C1-7Br | 4-(bis(7-bromo-5-chloro-1H-pyrrolo[2,3-c]pyridin-3-yl)methyl)phenol | 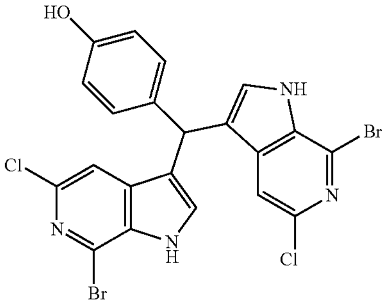 [SMILES: Oc1ccc(C(c2c[nH]c3c(Br)nc(Cl)cc23)c2c[nH]c3c(Br)nc(Cl)cc23)cc1] |
| SP-6azaBIM 125 series | | | |
| 45 | SP-6azaBIM 125-7Cl | 3,3'-((4-bromophenyl)methylene) bis(7-chloro-1H-pyrrolo[2,3-c]pyridine) | 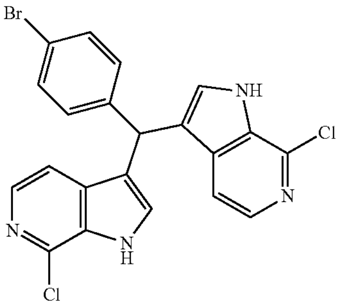 [SMILES: Clc1nccc2c(C(c3ccc(Br)cc3)c3c[nH]c4c(Cl)nccc34)c[nH]c12] |
| 46 | SP-6azaBIM 125-5Cl | 3,3'-((4-bromophenyl)methylene) bis(5-chloro-1H-pyrrolo[2,3-c]pyridine) | 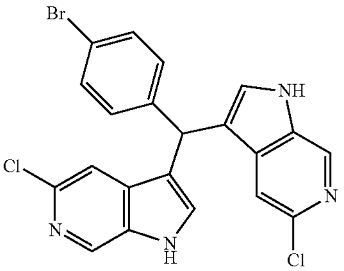 [SMILES: Clc1cc2c(C(c3ccc(Br)cc3)c3c[nH]c4cnc(Cl)cc34)c[nH]c2cn1] |
| 47 | SP-6azaBIM 125-5NO | 3,3'-((4-bromophenyl)methylene) bis(5-nitro-1H-pyrrolo[2,3-c]pyridine) | 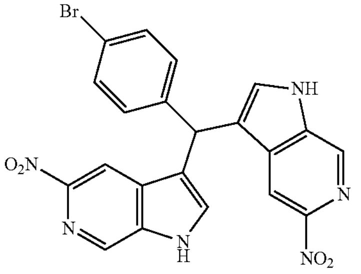 [SMILES: O=[N+]([O-])c1cc2c(C(c3ccc(Br)cc3)c3c[nH]c4cnc([N+](=O)[O-])cc34)c[nH]c2cn1] |

TABLE 2-continued

| Compound No. | Compound name | Chemical name | Structure |
| --- | --- | --- | --- |
| 48 | SP-6azaBIM 125-7OMe | 3,3'-((4-bromophenyl)methylene) bis(7-methoxy-1H-pyrrolo[2,3-c]pyridine) | 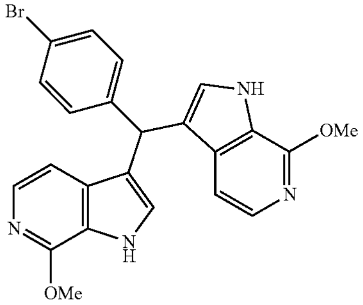 [SMILES: COc1nccc2c(C(c3ccc(Br)cc3)c3c[nH]c4c(OC)nccc34)c[nH]c12] |
| | | SP-6azaBIM 129 series | |
| 49 | SP-6azaBIM 129 | 5-(bis(1H-pyrrolo[2,3-c]pyridin-3-yl)methyl)benzene-1,2,3-triol | 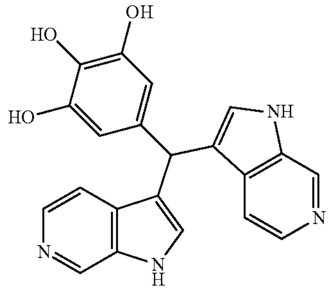 [SMILES: Oc1cc(C(c2c[nH]c3cnccc23)c2c[nH]c3cnccc23)cc(O)c1O] |
| 50 | SP-6azaBIM 129-7C1 | 5-(bis(7-chloro-1H-pyrrolo[2,3-c]pyridin-3-yl)methyl)benzene-1,2,3-triol | 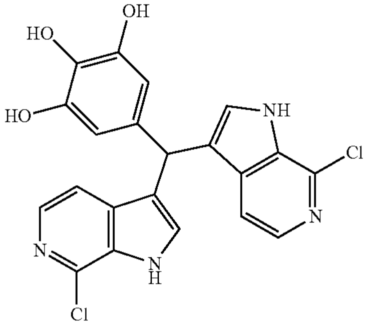 [SMILES: Oc1cc(C(c2c[nH]c3c(Cl)nccc23)c2c[nH]c3c(Cl)nccc23)cc(O)c1O] |
| 51 | SP-6azaBIM 129-5C1 | 5-(bis(5-chloro-1H-pyrrolo[2,3-c]pyridin-3-y1)methyl)benzene-1,2,3-triol | 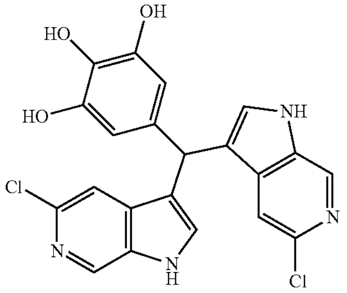 [SMILES: Oc1cc(C(c2c[nH]c3cnc(Cl)cc23)c2c[nH]c3cnc(Cl)cc23)cc(O)c1O] |
| 52 | SP-6azaBIM 129-5Br | 5-(bis(5-bromo-1H-pyrrolo[2,3-c]pyridin-3-y1)methyl)benzene-1,2,3-triol | 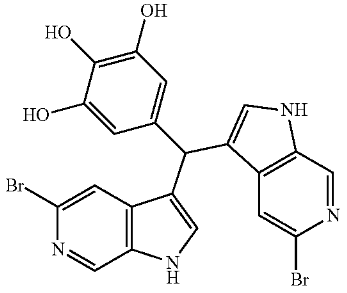 |

TABLE 2-continued
| Compound No. | Compound name | Chemical name | Structure |
|---|---|---|---|
| 53 | SP-6azaBIM 129-7Br | 5-(bis(7-bromo-1H-pyrrolo[2,3-c]pyridin-3-yl)methyl)benzene-1,2,3-triol | 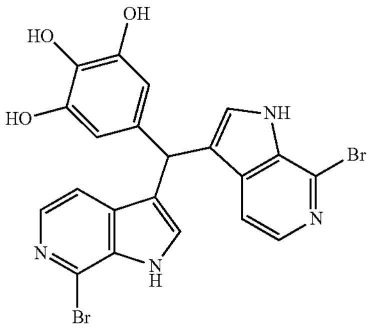 [SMILES: Oc1cc(C(c2c[nH]c3c(Br)nccc23)c2c[nH]c3c(Br)nccc23)cc(O)c1O] |
| 54 | SP-6azaBIM 129-7OMe | 5-(bis(7-methoxy-1H-pyrrolo[2,3-c]pyridin-3-yl)methyl)benzene-1,2,3-triol | 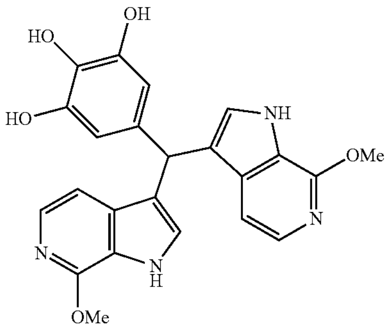 [SMILES: COc1nccc2c(C(c3cc(O)c(O)c(O)c3)c3c[nH]c4c(OC)nccc34)c[nH]c12] |
| 55 | SP-6azaBIM 129-5C1-7Br | 5-(bis(7-bromo-5-chloro-1H-pyrrolo[2,3-c]pyridin-3-yl)methyl)benzene-1,2,3-triol | 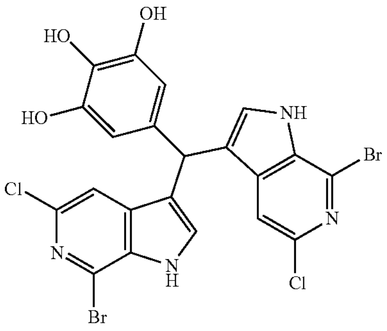 [SMILES: Oc1cc(C(c2c[nH]c3c(Br)nc(Cl)cc23)c2c[nH]c3c(Br)nc(Cl)cc23)cc(O)c1O] |
| 56 | SP-6azaBIM 129-5NO2 | 5-(bis(5-nitro-1H-pyrrolo[2,3-c]pyridin-3-yl)methyl)benzene-1,2,3-triol | 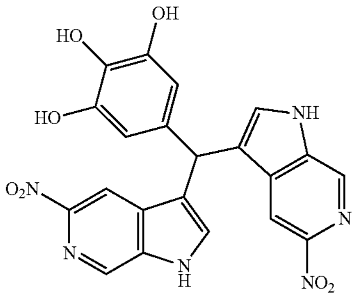 [SMILES: O=[N+]([O-])c1cc2c(C(c3cc(O)c(O)c(O)c3)c3c[nH]c4cnc([N+](=O)[O-])cc34)c[nH]c2cn1] |

TABLE 2-continued

| Compound No. | Compound name | Chemical name | Structure |
|---|---|---|---|
| | | SP-6azaBIM 5 series | |
| 57 | SP-6azaBIM 5-7C1 | 4-(bis(7-chloro-1H-pyrrolo[2,3-c]pyridin-3-yl)methyl)aniline | 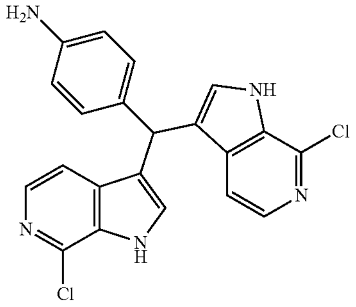 [SMILES: Nc1ccc(C(c2c[nH]c3c(Cl)nccc23)c2c[nH]c3c(Cl)nccc23)cc1] |
| 58 | SP-6azaBIM 5-7Br | 4-(bis(7-bromo-1H-pyrrolo[2,3-c]pyridin-3-yl)methyl)aniline | 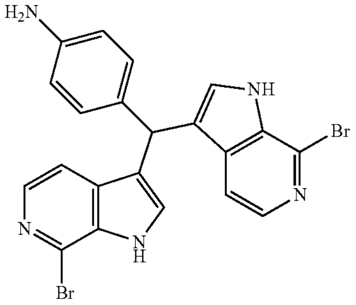 [SMILES: Nc1ccc(C(c2c[nH]c3c(Br)nccc23)c2c[nH]c3c(Br)nccc23)cc1] |
| 59 | SP-6azaBIM 5-7OMe | 4-(bis(7-methoxy-1H-pyrrolo[2,3-c]pyridin-3-yl)methyl)aniline | 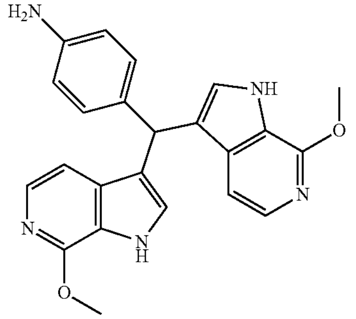 [SMILES: COc1nccc2c(C(c3ccc(N)cc3)c3c[nH]c4c(OC)nccc34)c[nH]c12] |
| | | SP-7azaBIM 135 series | |
| 60 | SP-7azaBIM 135 | 4-(bis(1H-pyrrolo[2,3-b]pyridin-3-yl)methyl)phenol $^1$H NMR (600 MHz DMSO-d6) = δ 5.73 (1H, s), δ 6.69 (2H, d), δ 6.89 (4H, d), δ 7.13 (2H, d), δ 7.59 (2H, d), δ 8.15 (2H, t), δ 9.21 (1H, s), δ 11.39 (2H, s). $^{13}$C NMR (150 MHz DMSO-d6) = δ 30.67, 114.79, 114.91, 117.01, 118.79, 123.61, 127.20, 129.09, 134.22, 142.34, 148.80, 155.47. | 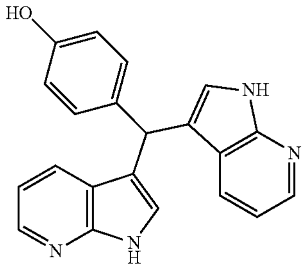 [SMILES: Oc1ccc(C(c2c[nH]c3ncccc23)c2c[nH]c3ncccc23)cc1] |

TABLE 2-continued

| Compound No. | Compound name | Chemical name | Structure |
|---|---|---|---|
| 61 | SP-7azaBIM 135-5Cl | 4-(bis(5-chloro-1H-pyrrolo[2,3-b]pyridin-3-y1)methyl)phenol | 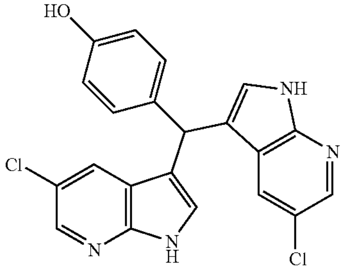 [SMILES: Oc1ccc(C(c2c[nH]c3ncc(Cl)cc23)c2c[nH]c3ncc(Cl)cc23)cc1] |
| 62 | SP-7azaBIM 135-5Br | 4-(bis(5-bromo-1H-pyrrolo[2,3-b]pyridin-3-yl)methyl)phenol | 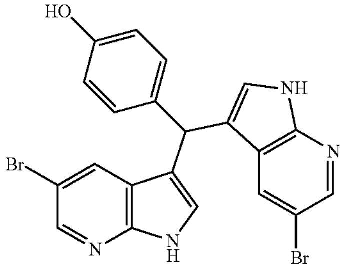 [SMILES: Oc1ccc(C(c2c[nH]c3ncc(Br)cc23)c2c[nH]c3ncc(Br)cc23)cc1] |
| 63 | SP-7azaBIM 135-5OMe | 4-(bis(5-methoxy-1H-pyrrolo[2,3-b]pyridin-3-yl)methyl)phenol | 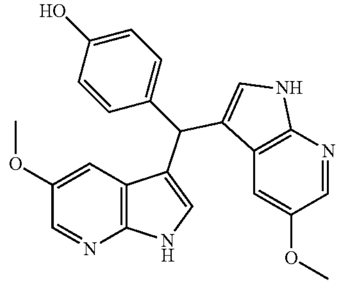 [SMILES: COc1cnc2[nH]cc(C(c3ccc(O)cc3)c3c[nH]c4ncc(OC)cc34)c2c1] |
| | | SP-7azaBIM 126 series | |
| 64 | SP-7azaBIM 126 | 3,3'-((4-bromophenyl)methylene) bis(1H-pyrrolo[2,3-b]pyridine) $^1$H NMR (600 MHz DMSO-d6) = δ 5.81 (1H, s), δ 5.95 (1H, d), δ 6.99 (1H, q), δ 7.29 (1H, d), δ 7.40 (2H, d), δ 7.49 (2H, d), δ 7.79 (1H, t), δ 8.15 (1H, t), δ 11.49 (1H, s) $^{13}$C NMR (150 MHz DMSO-d6) = δ 68.14, 115.02, 115.64, 117.67, 117.90, 119.51, 123.02, 127.62, 128.45, 130.77, 142.54, 144.84, 148.81 | 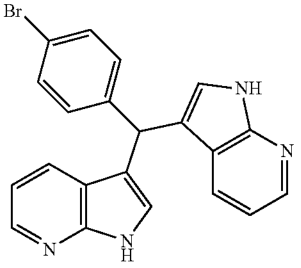 [SMILES: Brc1ccc(C(c2c[nH]c3ncccc23)c2c[nH]c3ncccc23)cc1] |
| 65 | SP-7azaBIM 126-5NO | 3,3'-((4-bromophenyl)methylene) bis(5-nitro-1H-pyrrolo[2,3-b]pyridine) | 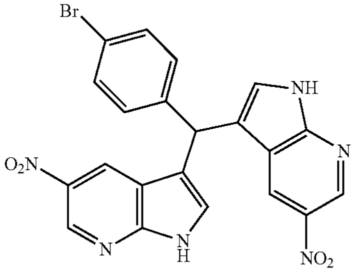 [SMILES: O=[N+]([O-])c1cnc2[nH]cc(C(c3ccc(Br)cc3)c3c[nH]c4ncc([N+](=O)[O-])cc34)c2c1] |

TABLE 2-continued

| Compound No. | Compound name | Chemical name | Structure |
|---|---|---|---|
| 66 | SP-7azaBIM 126-5OMe | 3,3'-((4-bromophenyl)methylene) bis(5-methoxy-1H-pyrrolo[2,3-b]pyridine) | 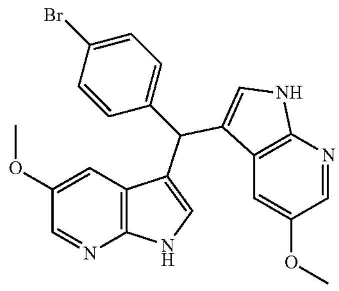 [SMILES: COc1cnc2[nH]cc(C(c3ccc(Br)cc3)c3c[nH]c4ncc(OC)cc34)c2c1] |

Example 39. Antibiotic Adjuvant Assessment

Microorganisms, Media, Antibiotics and Test Compound Preparations

Reference microorganisms as well as clinical strains used to evaluate the antimicrobial adjuvant properties of SP-6azaBIM 125 and SP-6azaBIM 136 are listed in Table 3. Clinical strains of bacteria were kindly provided by the Faculty of Medical Sciences, UWI, St. Augustine, Trinidad. All bacterial cultures were cryopreserved in 30% glycerol/Brain Heart Infusion (BHI) at −80° C. Cultures were revived on BHI agar (Oxoid Ltd, England) and maintained at 4° C. until needed.

Prior to each experiment, cultures were streaked onto clean BHI agar plates and incubated at 35° C. for 24 hours. Colonies of the respective cultures were selected and inoculated in phosphate buffer saline (pH 7.5) to a 0.5 McFarland turbidity standard (equivalent to $10^8$ CFU $mL^{-1}$). For inhibitory studies the bacterial suspensions were diluted 1:100 in cation-adjusted Mueller Hinton Broth (ca-MHB) (Oxoid Ltd, England). Fastidious bacteria including *Streptococcus pneumoniae, Haemophilus infuenzae* and *Clostridium difficile* were maintained on BHI agar with 5% defibrinated sheep blood and diluted in ca-MHB with 5% defibrinated sheep blood.

Antibiotic powders used in this study were purchased from Sigma Aldrich Ltd. (WI, USA). Antibiotic stock solutions were made at 50 mg $mL^{-1}$ according to Andrews (2001) and working solutions were prepared 24 h before use and stored at 4° C.

HCl salts of the of the SP-azaBIM test compounds were prepared prior to testing and stored at 4° C. Working preparations of each compound were made to 1 mg/mL in sterile deionised water.

TABLE 3

| Bacteria used in this study | | |
|---|---|---|
| | Bacteria strain | Reference |
| Gram positive bacteria | *Bacillus cereus* ATCC 11778 | ATCC |
| | *Clostridioides difficile* ATCC BAA-1870 | ATCC |
| | *Enterococcus faecalis* ATCC 51299 | ATCC |
| | *Streptococcus pneumoniae* ATCC 49619 | ATCC |
| | *Staphylococcus aureus* ATCC BAA-2312 | ATCC |
| Gram negative bacteria | *Enterobacter cloacae* ATCC BAA-1143 | ATCC |
| | *Escherichia coli* serotype O157:H7 ATCC 35150 | ATCC |
| | *Escherichia coli* clinical isolate 4427 | This study |
| | *Haemophilus influenzae* ATCC 33533 | ATCC |
| | *Klebsiella pneumoniae* ATCC BAA-2814 | ATCC |

TABLE 3-continued

| Bacteria used in this study | |
|---|---|
| Bacteria strain | Reference |
| *Klebsiella pneumoniae* ATCC 49472 | ATCC |
| *Pseudomonas aeruginosa* ATCC 9027 | ATCC |
| *Pseudomonas aeruginosa* MDR 5805 | This study |
| *Salmonella enterica* serovar Typhimurium ATCC 14028 | ATCC |
| *Acinetobacter baumannii* clinical isolate 9978 | This study |
| *Yersenia enterolitica* ATCC 9600 | ATCC |
| *Shigella sonnei* ATCC 29930 | ATCC |
| *Proteus vulgaris* ATCC 49312 | ATCC |
| *Stenotrophomonas maltophilia* MDR 7785 | This study |

Assessment of In Vitro Antibiotic Adjuvant Activity

The antibiotic adjuvant activity of the SPazaBIMs were evaluated in combination with representative antibiotics (representing 13 antibiotic classes) against the 19 pathogens strains listed in Table 3. To assess the adjuvant properties of the SP-azaBIM molecules, a modified checkerboard minimum inhibitory concentration assay was used. A fixed concentration of the respective antibiotic (susceptible breakpoint concentration) was mixed with a twofold dilution series of the test SP-azaBIM (FIG. 1). This was to determine the concentration of SP-azaBIM needed potentiate the antibiotic at a clinically susceptible breakpoint concentration. Antibiotic susceptible breakpoint concentrations for the respective bacteria were determined using Clinical Laboratory Standards Institute (CLSI) criteria M100 ED31.

In this study, only those antibiotics to which the bacterial was classed as resistant were included in the adjuvant assays. In this assay we recorded the rescue concentration of the SP-BIM for a respective antibiotic. The rescue concentration was defined as the concentration of the adjuvant that reduces the minimum inhibitory concentration (MIC) of an antibiotic to the susceptibility breakpoint.

Immediately prior to testing, the respective antibiotic and SP-azaBIM was dissolved in sterile deionised water at 20× the required test concentration. Each microtiter well was then inoculated with 180 μl of bacterial inoculum of $10^6$ CFU/ml in ca-MHB, and 10 μl each if the antibiotic and SP-azaBIM was added to the plates. These plates were then incubated at 35° C. for 24 h under aerobic conditions. A similar method was followed for the fastidious pathogens except that they were cultured in ca-MHB with 5% sheep blood and 5% $CO_2$.

Bacterial growth was visually inspected after the incubation period and the rescue concentration of the test SP-azaBIM was determined as the lowest concentration of the compound needed to reduce bacterial growth by 99.99% at the susceptible breakpoint concentration of the antibiotic. For example, CLSI states that *Pseudomonas aeruginosa* is susceptible to the Imipenem if the MIC is ≤2 μg $mL^{-1}$. If the bacteria can tolerate this concentration in vitro, then the bacteria has an intermediate or absolute resistance toward that antibiotic. The goal was to determine the concentration of SP-azaBIM needed to cause *P. aeruginosa* death at 2 μg $mL^{-1}$ of Imipenem therefore restoring susceptibility of the bacteria to toward the antibiotic.

The antibiotics tested include:

Beta Lactams: Ampicillin, Penicillin, Amoxicillin

Cephalosporins: Cefaclor, Cefotaxime, Cephalexin

Aminoglycosides: Kanamycin, Streptomycin, Gentamycin, Neomycin

Macrolides: Erythromycin, Azithromycin

Carbapenems: Imipenem, Meropenem

Monobactams: Aztreonam

Glycopeptides: Vancomycin

Tetracyclines: Tetracycline, Chlortetracycline, Doxycycline

Antifolates: Trimethoprim

Polymyxins: Polymyxin B, Colistin

Fluroquinolones: Norfloxacin, Ciprofloxacin

Phenicol: Chloramphenicol

Rifamycin: Rifampicin

Results

Based on the stage of synthesis, and purification of the SP-azaBIMs, test four compounds for antibiotic adjuvant activity were tested, including:

1. SP-6azaBIM 136—4-(bis(1H-pyrrolo[2,3-c]pyridin-3-yl)methyl)phenol
2. SP-6azaBIM 125—3,3'-((4-bromophenyl)methylene)bis(1H-pyrrolo[2,3-c]pyridine)
3. SP-7azaBIM 135—4-(bis(1H-pyrrolo[2,3-b]pyridin-3-yl)methyl)phenol
4. SP-7azaBIM 126—3,3'-((4-bromophenyl)methylene)bis(1H-pyrrolo[2,3-b]pyridine)

None of the compounds tested displayed any direct antibacterial activity at <1028 μg mL-1

TABLE 4

Rescue concentrations of SP-azaBIMs for ineffective antibiotics against *S. aureus*

| Compound | *Staphylococcus aureus* ATCC BAA-2312 Antibiotics (susceptible breakpoint concentrations μg $mL^{-1}$) | | | | |
|---|---|---|---|---|---|
| | Pen (0.12) | Van (2) | Gen (4) | Azi (2) | Tri (8) |
| SP-6azaBIM 136 | >128 | 128 | >128 | >128 | >128 |
| SP-6azaBIM 125 | >128 | >128 | 64 | >128 | >128 |
| SP-7azaBIM 135 | >128 | >128 | >128 | >128 | >128 |
| SP-7azaBIM 126 | >128 | >128 | >128 | >128 | >128 |

>128 represents no adjuvant effect within the range tested.

TABLE 5

Rescue concentrations of SP-azaBIMs for ineffective antibiotics against *E. faecium*

| Compound | *Enterococcus faecalis* ATCC 51299 Antibiotics (susceptible breakpoint concentrations μg $mL^{-1}$) | | | | | |
|---|---|---|---|---|---|---|
| | Amp (8) | Van (4) | Ery (0.5) | Tri (8) | Dox (4) | Chl (8) |
| SP-6azaBIM 136 | >128 | >128 | >128 | >128 | >128 | >128 |
| SP-6azaBIM 125 | >128 | >128 | >128 | >128 | >128 | >128 |
| SP-7azaBIM 135 | >128 | >128 | >128 | >128 | >128 | >128 |
| SP-7azaBIM 126 | 32 | 64 | >128 | >128 | >128 | >128 |

TABLE 6

Rescue concentrations of SP-azaBIMs for ineffective antibiotics against *S. pneumoniae*

| Compound | *Streptococcus pneumoniae* ATCC 49619 Antibiotics (susceptible breakpoint concentrations μg $mL^{-1}$) | | |
|---|---|---|---|
| | Amox (2) | Imi (0.12) | Ery (0.25) |
| SP-6azaBIM 136 | >128 | >128 | >128 |
| SP-6azaBIM 125 | >128 | >128 | >128 |
| SP-7azaBIM 135 | >128 | >128 | >128 |
| SP-7azaBIM 126 | >128 | >128 | >128 |

Note:

Based on these results the SP-azaBIMS display limited activity toward G + ve bacteria. This may change once we test other compounds.

TABLE 7

Rescue concentrations of SP-azaBIMs for ineffective antibiotics against *E. cloacae*

| Compound | *Enterobacter cloacae* ATCC BAA-1143 Antibiotics (susceptible breakpoint concentrations μg $mL^{-1}$) | | | | | | | | |
|---|---|---|---|---|---|---|---|---|---|
| | Amp (8) | Gen (4) | Azi (16) | Tet (4) | Dox (4) | Chl (8) | Imi (1) | Ceph (8) | Col (8) |
| SP-6azaBIM 136 | 16 | 8 | 16 | 4 | 4 | 32 | 4 | 16 | 16 |
| SP-6azaBIM 125 | 32 | >128 | >128 | >128 | >128 | >128 | >128 | >128 | >128 |
| SP-7azaBIM 135 | 64 | >128 | >128 | >128 | >128 | >128 | 32 | >128 | 64 |
| SP-7azaBIM 126 | 128 | >128 | >128 | >128 | >128 | >128 | >128 | >128 | >128 |

TABLE 8

Rescue concentrations of SP-azaBIMs for ineffective antibiotics against *E. coli* 35150

| Compound | Amp (8) | Gen (4) | Cip (0.25) | Dox (4) | Imi (1) | Col (8) |
|---|---|---|---|---|---|---|
| | *Escherichia coli* ATCC 35150 Antibiotics (susceptible breakpoint concentrations μg $mL^{-1}$) | | | | | |
| SP-6azaBIM 136 | 8 | 16 | 16 | 4 | 4 | 16 |
| SP-6azaBIM 125 | 16 | 16 | 8 | 32 | 4 | 2 |
| SP-7azaBIM 135 | >128 | >128 | >128 | >128 | 64 | 64 |
| SP-7azaBIM 126 | >128 | >128 | >128 | >128 | >128 | >128 |

TABLE 12

Rescue concentrations of SP-azaBIMs for ineffective antibiotics against *A. baumannii* 9978

| Compound | Amox (8) | Imi (2) | Mero (2) | Pol B (2) | Col (2) | Gen (4) | Cef (8) |
|---|---|---|---|---|---|---|---|
| | *Acinetobacter baumannii* clinical isolate 9978 Antibiotics (susceptible breakpoint concentrations μg $mL^{-1}$) | | | | | | |
| SP-6azaBIM 136 | 16 | 2 | 32 | 64 | 64 | 16 | 32 |
| SP-6azaBIM 125 | 16 | 4 | 8 | 16 | 4 | 2 | 2 |

TABLE 9

Rescue concentrations of SP-azaBIMs for ineffective antibiotics against *K. pneumoniae* 2814

| Compound | Amp (8) | Amox (8) | Gen (4) | Azi (16) | Tet (4) | Dox (4) | Chl (8) | Imi (1) | Ceph (8) | Col (8) | Aze (4) | Cef (16) |
|---|---|---|---|---|---|---|---|---|---|---|---|---|
| | *Klebsiella pneumoniae* ATCC BAA-2814 Antibiotics (susceptible breakpoint concentrations μg $mL^{-1}$) | | | | | | | | | | | |
| SP-6azaBIM 136 | 32 | 16 | 4 | 16 | 4 | 4 | 32 | 4 | 16 | 16 | 4 | 8 |
| SP-6azaBIM 125 | 16 | 4 | 16 | 32 | 32 | 8 | 32 | 2 | 32 | 4 | 4 | 16 |
| SP-7azaBIM 135 | >128 | >128 | >128 | >128 | >128 | >128 | >128 | >128 | >128 | >128 | >128 | >128 |
| SP-7azaBIM 126 | >128 | >128 | >128 | >128 | >128 | >128 | >128 | >128 | >128 | >128 | >128 | >128 |

TABLE 10

Rescue concentrations of SP-azaBIMs for ineffective antibiotics against *K. pneumoniae* 49472

| Compound | Amp (8) | Amox (8) | Imi (1) | Mero (1) | Pol B (8) | Col (8) |
|---|---|---|---|---|---|---|
| | *Klebsiella pneumoniae* ATCC 49472 Antibiotics (susceptible breakpoint concentrations μg $mL^{-1}$) | | | | | |
| SP-6azaBIM 136 | 64 | 32 | 16 | 32 | 16 | 32 |
| SP-6azaBIM 125 | 16 | 4 | 2 | 4 | 4 | 4 |
| SP-7azaBIM 135 | >128 | >128 | >128 | >128 | >128 | >128 |
| SP-7azaBIM 126 | >128 | >128 | >128 | >128 | >128 | >128 |

TABLE 12-continued

Rescue concentrations of SP-azaBIMs for ineffective antibiotics against *A. baumannii* 9978

| Compound | Amox (8) | Imi (2) | Mero (2) | Pol B (2) | Col (2) | Gen (4) | Cef (8) |
|---|---|---|---|---|---|---|---|
| | *Acinetobacter baumannii* clinical isolate 9978 Antibiotics (susceptible breakpoint concentrations μg $mL^{-1}$) | | | | | | |
| SP-7azaBIM 135 | >127 | >128 | >128 | >128 | >128 | >128 | >128 |
| SP-7azaBIM 126 | >128 | >128 | >128 | >128 | >128 | >128 | >128 |

TABLE 11

Rescue concentrations of SP-azaBIMs for ineffective antibiotics against *P. aeruginosa* MDR 5805

| Compound | Amox (8) | Imi (2) | Mero (2) | Pol B (2) | Col (2) | Gen (4) |
|---|---|---|---|---|---|---|
| | *Pseudomonas aeruginosa* MDR 5805 Antibiotics (susceptible breakpoint concentrations μg $mL^{-1}$) | | | | | |
| SP-6azaBIM 136 | 2 | 2 | 2 | 4 | 4 | 4 |
| SP-6azaBIM 125 | 128 | >128 | >128 | >128 | >128 | 16 |
| SP-7azaBIM 135 | 64 | >128 | >128 | >128 | >128 | >128 |
| SP-7azaBIM 126 | >128 | >128 | >128 | >128 | >128 | >128 |

TABLE 13

Rescue concentrations of SP-azaBIMs for ineffective antibiotics against *S. maltophilia*

| Compound | Ceph (8) | Imi (2) | Mero (2) | Gen (4) | Cef (8) | Cip (2) | Chl (8) | Tri (2) |
|---|---|---|---|---|---|---|---|---|
| | *Stenotrophomonas maltophilia* MDR 7785 Antibiotics (susceptible breakpoint concentrations μg $mL^{-1}$) | | | | | | | |
| SP-6azaBIM 136 | 64 | 32 | 32 | 64 | 32 | 16 | 16 | >128 |
| SP-6azaBIM 125 | 8 | 16 | 4 | 8 | 8 | 2 | 4 | 64 |
| SP-7azaBIM 135 | >128 | >128 | >128 | >128 | >128 | >128 | >128 | >128 |
| SP-7azaBIM 126 | >128 | 16 | 32 | >128 | >128 | >128 | >128 | >128 |

Example 40. In Vivo Adjuvant Activity of SP-azaBIM 136

Materials and Methods

For both lethal and non-lethal infection models involving Carbapenem resistant *Klebsiella pneumoniae* suitable strains, number of mice per treatment and bacterial infection dose were predetermined in preliminary experiments.

For the non-lethal mouse peritonitis infection models, overnight cultures of clinical isolate CR-*K. pneumoniae* 7225 were washed twice and re-suspended in phosphate buffer saline (PBS). Each mouse (n=6 per group) received an intraperitoneal (i.p.) injection of 200 μl of bacterial suspension ($1 \times 10^4$ CFU $ml^{-1}$). One hour post infection, the mice were divided into seven groups and treated subcutaneously with the respective treatments: TO-Vehicle alone (PBS); T1—Ciprofloxacin (Cip) only (10 mg $kg^{-1}$); T2—Meropenem (Mero) only (10 mg $kg^{-1}$); T3—Cip (10 mg $kg^{-1}$)+SP-azaBIM 136 (10 mg $kg^{-1}$); T4—Mero (10 mg $kg^{-1}$)+SP-azaBIM 136 (10 mg $kg^{-1}$); T5—Colistin only (10 mg $kg^{-1}$); and T6—SP-azaBIM 136 only (10 mg $kg^{-1}$).

Mice were then treated once daily for two subsequent days (i.e. 24 h and 48 h). Twenty-four-hours after the last dose, the mice were euthanized via cervical dislocation and their spleen and liver excised, homogenized in PBS and plated onto Hichrome™ *Klebsiella* selective media (HiMedia Laboratories, PA, USA). The plates were incubated at 35° C. for 24 h and bacterial counts were determined (CFU $g^{-1}$ organ).

For the lethal peritonitis infections, mice were treated as in the non-lethal infection studies except the inoculation dose was $2 \times 10^7$ CFU $mL^{-1}$ *K. pneumoniae* 7225. The mice were then divided into the previously listed treatment regimens and treatment was provided every 24 h for two days after infection. Mice were monitored for mortality for 7 days and the moribund mice were euthanized humanely using cervical dislocation. Results were displayed as the percent mice survival (n=10) each day over a 7-day period.

Results

Based on the significance of the SP-azaBIMs to restore the in vitro efficacy of antibiotics against high priority pathogenic bacteria, we examined if these compounds could provide proof of concept that they could be used to treat in vivo infections. To test this, we performed both non-lethal and lethal intraperitoneal infection models in Swiss Albino mice. Infections studies were conducted using the *K. pneumoniae* clinical isolate 7225 as it was both ESBL+, carbapenem and fluoroquinolone resistant and hence was used in this study as well.

For the *K. pneumoniae* infections trials, we tested combination therapies of SP-azaBIM 136 with Meropenem (carbapenem) (10 mg $kg^{-1}$) and Ciprofloxacin (fluoroquinolone) (10 mg $kg^{-1}$) respectively. Preliminary dosing experiments showed that Meropenem and Ciprofloxacin monotherapy at 10 mg $kg^{-1}$ were each ineffective against this *K. pneumoniae* strain, hence this dose was used in our experiments.

Figure 2B:
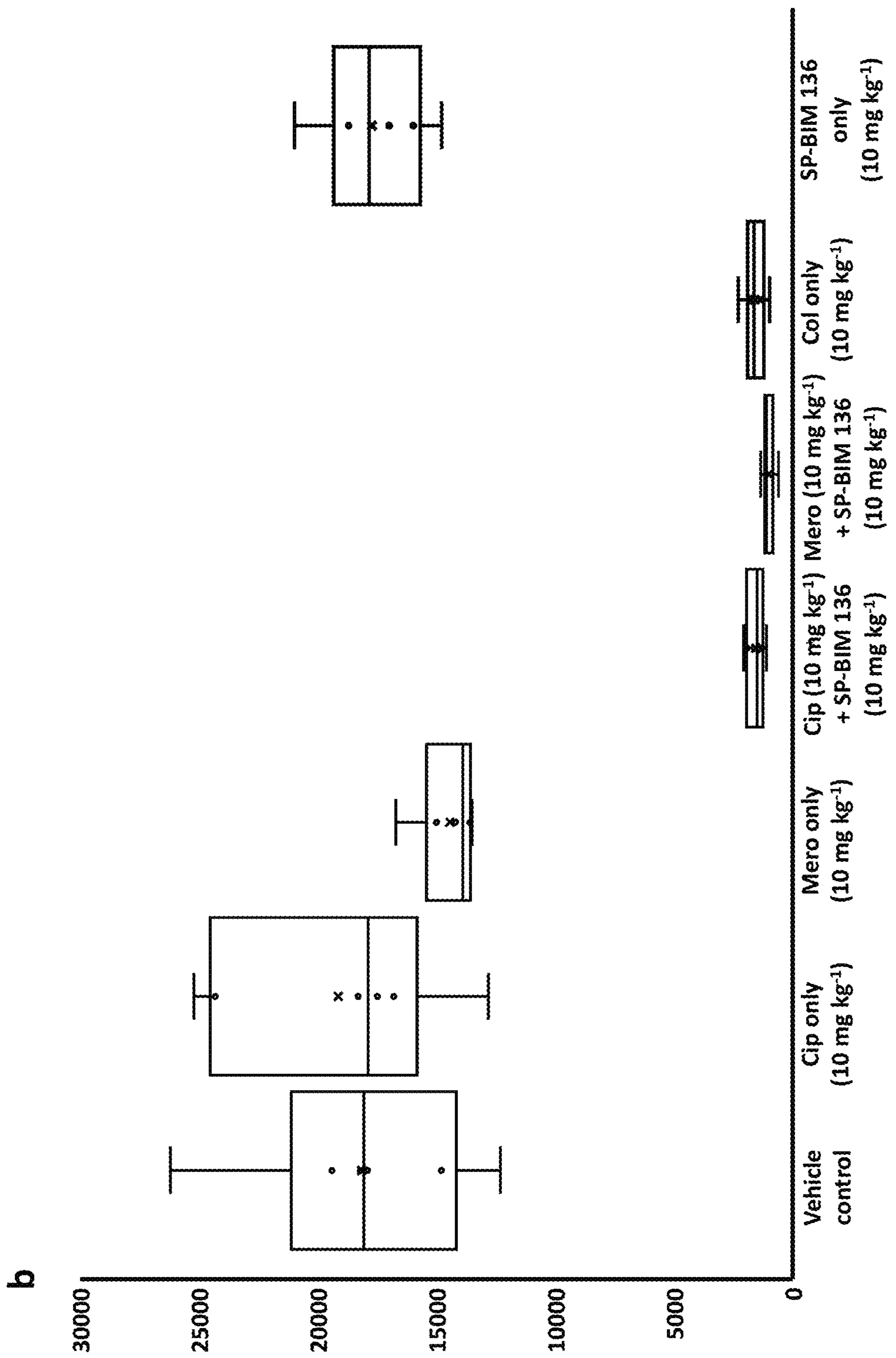

There was a significant reduction in the *K. pneumoniae* load in both the liver (FIG. 2*a*) and spleen (FIG. 2*b*) for the combination therapies compared to the respective antibiotic monotherapies. Mice were infected with *K. pneumoniae* 7225 ($1 \times 10^4$ CFU $ml^{-1}$) via i.p. injection. Mice were given three subcutaneous treatments (1 h, 24 h and 48 h post infection) of PBS, Ciprofloxacin (Cip) only (10 mg $kg^{-1}$), Meropenem (Mero) only (10 mg $kg^{-1}$), Ciprofloxacin (10 mg $kg^{-1}$)+SP-BIM 136 (10 mg $kg^{-1}$), Meropenem (10 mg $kg^{-1}$)+SP-BIM 136 (10 mg $kg^{-1}$). Colistin (Col) (10 mg $kg^{-1}$) was used as the positive control in this case. *K. pneumoniae* load in the liver (FIG. 2*a*) and spleen (FIG. 2*b*) was determined by selective plating on Hichrome™ *Klebsiella* selective media. Data bars represent the average (n=6 mice per treatment group)±standard error. Groups were analysed using a non-parametric Mann-Whitney U-test, and statistically significant (P values≤0.05) groups were denoted with different letters.

Regarding Meropenem, a 41-fold reduction of bacterial cells in the liver and a 14-fold reduction in the spleen was observed, when co-administered with SP-azaBIM 136. Likewise, the combination of Ciprofloxacin and SP-azaBIM 136 resulted in an approximate 53 and 12-fold reduction in the liver and spleen respectively, compared to Ciprofloxacin only treatment.

For survival experiments, Swiss albino mice were given lethal doses of *K. pneumoniae* 7225 (C) ($2 \times 10^7$ CFU $ml^{-1}$) via i.p. injection. Mice were treated the same as in the non-lethal peritonitis experiments and mortality was monitored for 7 days. Data lines represent the percent of mice (n=10 mice per treatment group) that survived daily. Individual antibiotic and SP-azaBIM 136 monotherapies resulted in 100% mortality in mice during the lethal *K. pneumoniae* infection trials, but co-treatments resulted in 100% survival for Ciprofloxacin+SP-BIM 136 and 90% survival for Meropenem+SP-BIM 136 (FIG. 3).

These results show that the potent in vitro antibiotic adjuvant properties displayed by SP-azaBIM 136 were translated to in vivo conditions and thus provide further evidence of their potential to protect mice from systemic infections of CR-*K. pneumoniae* in combination with antibiotics. On its own however, SP-azaBIM 136 were not able to reduce *K. pneumoniae* load in the organs, nor provide any protection to lethal infections.

Example 41. Gene Expression Analysis of *Klebsiella pneumoniae* Cells Treated with SP-azaBIM 136

Material and Methods

Cell treatment and RNA extraction: Overnight cultures of *Klebsiella pneumoniae* ATCC BAA-2814 grown on Brain Heart Infusion (BHI) agar was harvested and washed in phosphate buffer saline (pH=7.4) twice. Fresh Brain Heart infusion broth was inoculated with *K. pneumoniae* cells to a final concentration of $10^6$ CFU $mL^{-1}$. Cells were subjected to the following treatments: T0—Vehicle only ($ddH_2O$); T1—Meropenem only (0.25 MIC; 8 μg $mL^{-1}$); T2—Meropenem 0.25 MIC+SP-azaBIM 136 (2 ug $mL^{-1}$). Treated cells were incubated at 35° C. at 200 rpm and total RNA was extracted at 1 h and 6 h post exposure using TRIzol reagent (Life Technologies) following the manufacturer's protocol before eluting in DEPC treated water. Three biological replicates were included for each treatment.

Quantitative reverse transcription PCR analysis: Reverse transcription was done using the GoScript Reverse Transcriptase Kit (Promega, USA) employing a mixture (1:1) of random and oligo dT primers with 2 μg RNA as starting material in a 20-μL reaction following the manufacturers protocols. cDNA samples were then quantified by real-time PCR using specific primers in an Applied Biosystems 7500 Fast Real-Time PCR system (Life Technologies Corp., USA) and the data analysed using the $2^{(-\Delta\Delta ct)}$ method. The details of gene primers are listed in Table 14. Thermal cycling was performed using a two-step PCR amplification standard procedure at 95° C. for 30 s and 35 cycles of 95°

C. for 5 s and 60° C. for 30 s. The expression levels of all the genes were normalized using the *K. pneumoniae* RNA polymerase sigma factor (rpoD) gene as an internal standard.

Results

The phenotypic responses displayed by the bacteria upon treatment with SP-azaBIM 136 led to the hypothesis that the possible mechanism of action may be at a central regulatory level in the bacterial cells. The loss of antibiotic resistance *Klebsiella pneumoniae* cells treated with SP-azaBIM 136 resembled that of the effects of inhibition of bacterial two component systems (TCS). TCS signal transduction is a fundamental part of the complex cellular processes involving bacterial control of pathogenicity and resistance and, as such, is an important target for anti-infective development. This also follows on the mechanism of action displayed by the SP-BIMs in MRSA cells.

To examine this hypothesis, we investigated the expression of genes in *K. pneumoniae* ATCC BAA-2318 that were affected by SP-azaBIM 136 treatment. Expression of key transcription factors and their associated downstream resistance and pathogenicity genes was examined in *Klebsiella pneumoniae* cells treated with meropenem and a combination of meropenem and SP-azaBIM 136. Cells in the exponential phase were either treated with 0.25 MIC (8 μg $mL^{-1}$) of Meropenem only or a combination of 0.25 MIC meropenem and 10 μg $mL^{-1}$ of SP-azaBIM 136. Untreated cells served as the control for baseline gene expression. Cells were exposed to each agent for 1 h and 6 h, after which the total RNA was extracted, and cDNA synthesis performed. Exposing the cells to a sub-inhibitory concentration of Meropenem helped to induce stress responses in *K. pneumoniae*, as several studies have shown that both virulence factors and defense genes were upregulated in response to antibiotics. The addition of SP-azaBIM 136 was theorized to revert the expression of the relevant genes closer to baseline expression levels.

Figure 4A:
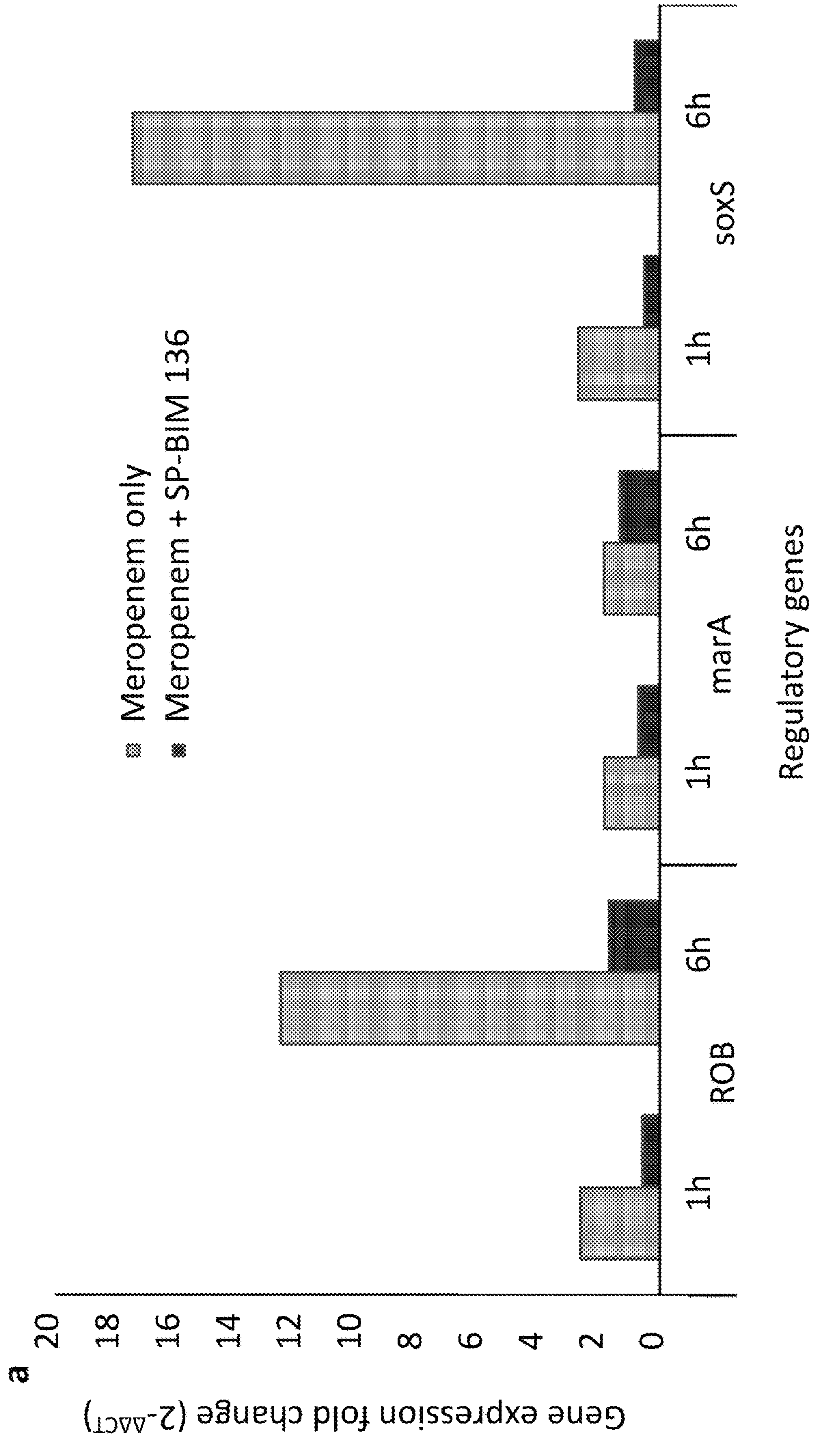
FIGS. 4A-4C depict the impact of SP-azaBIM 136 on gene expression in *K. pneumoniae*, according to one or more embodiments described herein.

The transcription factors ROB and soxS were all observed to be significantly upregulated in cells treated with meropenem only (FIG. 4*a*). This effect was seen at both the initially, after 1 h and then sustained through 6 h after exposure to the antibiotic. In both cases the expression of these genes was induced to a greater extent after 6 h. Expression of the ROB gene increased approximately 3-folds at 1 h and a further 12-folds at 6 h compared to untreated cells. The effect of the soxS gene was more profound, in that antibiotic treatment elicited an initial 3-folds and then an 18-folds increase in expression. This is possibly due to the cell's recognition of the antibiotic as a threat, and hence the immediate initiation of mechanisms to circumvent cell death.

The combination treatment of both meropenem and SP-azaBIM 136 suppressed expression of these genes to at or below the baseline levels. The ROB gene was reduced to 0.35 times that of baseline levels after 1 h and 1.4-fold after 6 h. Though this did represent an increase in gene expression, when compared to the expression observed under antibiotic treatment only, a significant suppressive effect was observed. An even greater suppressive effect was observed on the soxS gene where expression was observed at 0.28 and 0.76-fold compared to untreated cells. This represented a downregulation in these genes. While there was a similar trend with regard to the marA regulatory gene, the responses were not as profound as the other two genes.

Figure 4B:
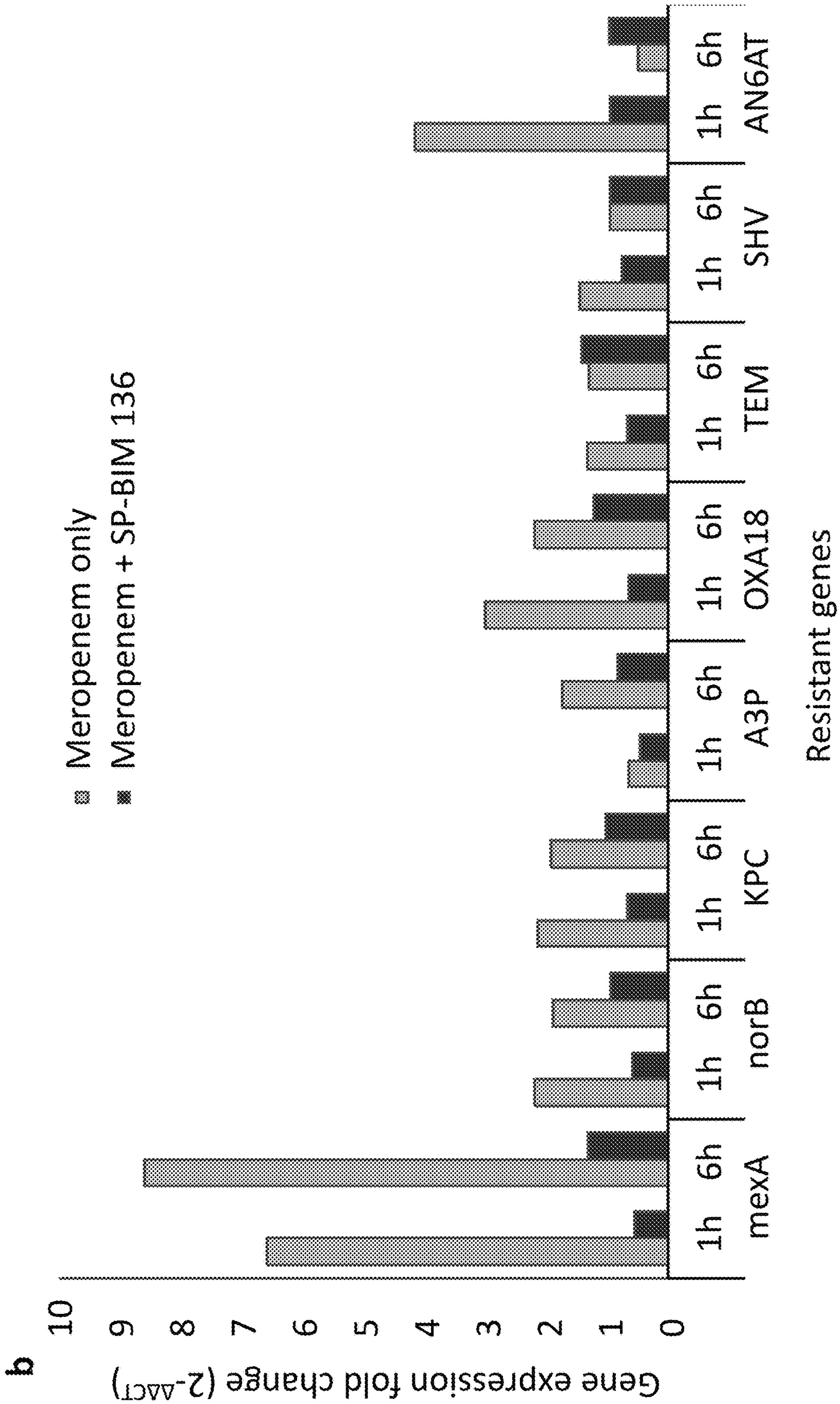
Figure 4C:
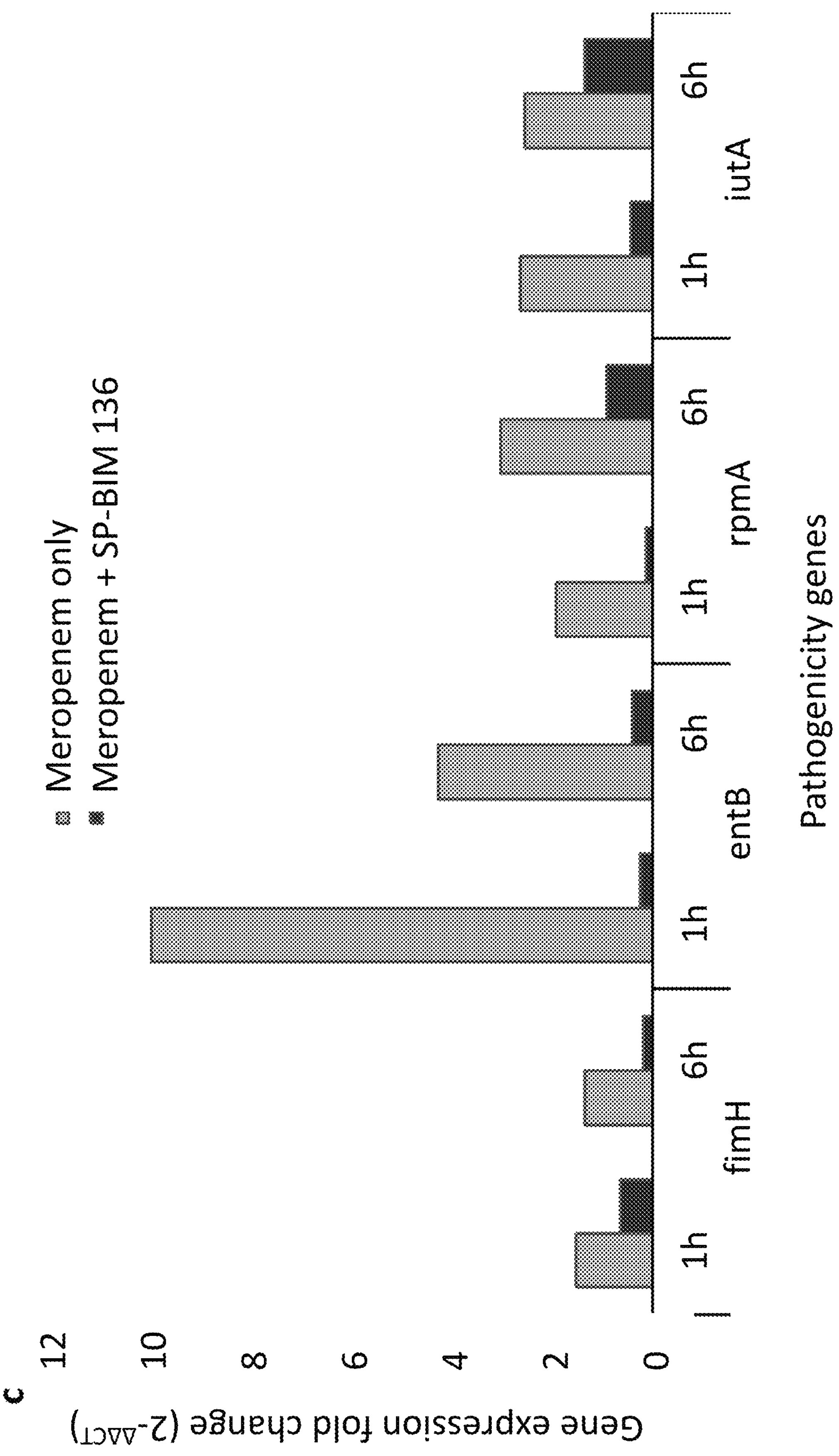

The suppressive effect displayed by SP-azaBIM 136 on the expression of these genes are significant since it can be translated to the reduced resistance and pathogenicity displayed by this pathogen. These transcriptional regulators bind to and control gene expression to increase bacterial fitness in a challenging environment. Transcriptional regulator associated with multidrug resistance, organic solvent tolerance, oxidative stress, and virulence in clinically relevant enterobacteria. It has been shown that there is a rapid increase in transcription of marA, soxS and ROB following exposure to antibiotics (and other inducer substrates), but that repression is rapidly reinstated following removal of the stimuli. The upregulation of the regulatory genes was then mirrored in the expression of resistance genes in FIG. 4*b* and virulence genes in FIG. 4*c*.

In terms of antibacterial resistance, it was observed that the cells elicited a strong defensive response when exposed to meropenem. The general trend was an upregulation of gene expression in the various resistance genes, when the bacterium treated with meropenem mixed with SP-azaBIM 136 expression was significantly reduced to below baseline levels in most cases. The most significant effects were observed with the efflux pump genes mexA and norB where expression peaked at 8.7 and 2.2-folds above untreated cells respectively. In each case the addition of SP-azaBIM 136 resulted in a 17 and 4.5-fold reduction in gene expression for both genes. Most of extended spectrum beta-lactamases as well as the carbapenemase gene KPC were also significantly suppressed when exposed to SP-azaBIM 136. The only exception was that of the TEM-1 gene where there was no significant variation in expression.

SP-azaBIM 136 also significantly reduced bacterial virulence gene expression. In each case where cells were exposed to meropenem, there was an increase in the expression of genes involved adhesion (fimH), siderophore production (entB, iutA) and capsular polysaccharide synthesis (rpmA) at both 1 h and 6 h after exposure. In each case, expression decreased significantly when SP-azaBIM 136 was added to the bacteria. This meant that the compound was effective in blocking *K. pneumoniae* 's genotypic responses to antibiotic therapy and reducing virulence by downregulating the expression of genes responsible for these effects.

TABLE 14

Details of genes and primers used in gene expression analysis of *K. pneumoniae* treated with SP-azaBIM 136

| | Gene name | Function | Primer name | Primer sequence | Amplicon size (bp) |
|---|---|---|---|---|---|
| Regulatory genes/ Transcription factors | Right origin-binding protein ROB | These transcriptional regulators bind to and control gene expression to increase bacterial fitness in a challenging environment. | 1-ROB-F<br>1-ROB-R | CAAAGAACATACCGGGCAGC<br>CGTTCAGGATCGGCTCGTTA | 101 |
| | Regulatory | Transcriptional regulator associated with | 1-soxS-F | CAGACCTTTACCCGCGTCTT | 72 |

TABLE 14-continued

Details of genes and primers used in gene expression analysis of *K. pneumoniae* treated with SP-azaBIM 136

| | Gene name | Function | Primer name | Primer sequence | Amplicon size (bp) |
|---|---|---|---|---|---|
| | protein SoxS | multidrug resistance, organic solvent tolerance, oxidative stress, and virulence in clinically relevant enterobacteria. | 1-soxS-R | ACTGTGGTTCTCTTTGCGGT | |
| | Multiple antibiotic resistance protein MarA | It has been shown that there is a rapid increase in transcription of marA, soxS and ROB following exposure to antibiotics (and other inducer substrates), but that repression is rapidly reinstated following removal of the stimuli. | 1-marA-F<br>1-marA-R | AGAAAGAGACCGGCCATTCC<br>TGCTGCGACTCGAAACCATA | 130 |
| Resistance genes | Amino-glycoside 3'-phospho-transferase | Primarily catalyzes the addition of phosphate from ATP to the 3'-hydroxyl group of a 4,6-disubstituted aminoglycoside, such as kanamycin. | 1-A3P-F<br>1-A3P-R | TCAACGGGAAACGTCTTGCT<br>TCGCGAGCCCATTTATACCC | 81 |
| | Amino-glycoside N(6')-acetyl-transferase type 1 | Catalyzes the transfer of an acetyl group from acetyl-CoA to the 6'-amino group of aminoglycoside molecules conferring resistance to a amikacin, gentamicin, kanamycin B, tobramycin, netilmicin, and isepamicin. | 1-AN6AT-F<br>1-AN6AT-R | AGCAACGATTCCGTCACACT<br>CCCCACCACTCGACGATATG | 95 |
| | Beta-lactamase OXA-18 | Hydrolyzes amoxicillin, ticarcillin, cephalothin, ceftazidime, cefotaxime, and aztreonam, but not imipenem or cephamycins. | 1-OXA18-F<br>1-OXA18-R | CGCCACTCTCCCAATCAGTT<br>AAAAGACGAGCACGGAGACA | 139 |
| | Beta-lactamase TEM-1 | TEM-type are the most prevalent beta-lactamases in enterobacteria; they hydrolyze the beta-lactam bond in susceptible beta-lactam antibiotics, thus conferring resistance to penicillins and cephalosporins. | 1-TEM-F<br>1-TEM-R | AGATCAGTTGGGTGCACGAG<br>GGGGCGAAAACTCTCAAGGA | 76 |
| | Beta-lactamase SHV-1 | SHV-1 can hydrolyse penicillin and cephalosporins but not expanded-spectrum antibiotics such as oxyimino cephalosporins and monobactams. | 2-SHV-F<br>2-SHV-R | GCAGCCGCTTGAGCAAATTA<br>TGCTCATCATGGGAAAGCGT | 131 |
| | Carbapenem-hydrolyzing beta-lactamase KPC | Hydrolyzes carbapenems, penicillins, cephalosporins and aztreonam with varying efficiency. | 1-KPC-F<br>1-KPC-R | ATCGCCGTCTAGTTCTGCTG<br>TATCCATCGCGTACACACCG | 141 |
| | Multidrug resistance protein MexA | The periplasmic linker component of the MexAB-OprM efflux system that confers multidrug resistance. Over-expression of the pump increases antibiotic and solvent efflux capacities. | 1-mexA-F<br>1-mexA-R | GCGATAAATGGCTGGTGCTG<br>TCCGTTATTGTTGACGGCGA | 116 |
| | Quinolone resistance protein NorB | Multidrug efflux pump that confers resistance against quinolones. Extrudes norfloxacin, ciprofloxacin, cetrimide, sparfloxacin, moxifloxacin. Contributes also to the efflux of tetracycline. | 2-norB-F<br>2-norB-R | CGGAGAACAAAATCGGCGTC<br>AAACCACAGGGCATACTGGG | 146 |
| Virulence/ pathogenicity | Entero-bactin synthase component BentB | Involved in the biosynthesis of the siderophore enterobactin (enterochelin) | 1-entB-F<br>1-entB-R | GATATCCCGGCGAACAAGGT<br>TCCTGCATGTCGTGGATCAG | 74 |
| | Type 1 fimbrin D-mannose specific adhesin FimH | Involved in regulation of length and mediation of adhesion of type 1 fimbriae. Adhesin responsible for the binding to D-mannose. | 1-fimH-F<br>1-fimH-R | CGACCTCTCCACGCAGATTT<br>CGGTGCCTGAAAAACTCGAC | 116 |

TABLE 14-continued

Details of genes and primers used in gene expression analysis of *K. pneumoniae* treated with SP-azaBIM 136

| Gene name | Function | Primer name | Primer sequence | Amplicon size (bp) |
|---|---|---|---|---|
| Regulator of the mucoid phenotype rpmA | Encodes a capsular polysaccharide found in hypermucoviscosity phenotype (HV) of klebsiella | 1-rpmA-F<br>1-rpmA-R | CCGAAAGAGCAGAGCGATGA<br>CCAGCACGGTATCGTCTTCA | 127 |
| Ferric aerobactin synthesis IutA | Biosythesis of aerobactin, an iron acquisition siderophore. Aerobactin production is associated with hyper-virulent *K. pneumoniae*. | 1-iutA-F<br>1-iutA-R | GGGCTCAATTCCGACCGTAT<br>CGTCGGGAACGGATAGAAGG | 141 |

Example 42. Molecular Docking of SP-azaBIMs to *Salmonella* Sensor Kinase PhoQ Catalytic Domain Methods Docking studies of the SP-azaBIM ligands and the sensor histidine kinase PhoQ were performed using the Maestro suite (Maestro version 11.7, Schrödinger Release 2018-4) using Glide score as the scoring function.

Library preparation: The chemical structures of the SP-azaBIMs were drawn and refined using the Ligprep module of the Maestro Suite v11.7. The 2D flat file was converted into 3D structures with accurate chiralities. The ionization states were generated for pH 7.0±2.0 by the EPIK module and tautomers and conformations were generated using the OPLS3 force field. Ring conformations with the lowest energy state were selected.

Protein preparation: The chosen molecular targets for molecular docking was the catalytic ATP (CA) binding domain *Salmonella typhimurium* PhoQ (PDB ID: 3CGY). This was obtained as crystal structures from the Protein Data Bank (PDB). The selected chains were edited for missing hydrogen and for assigning proper bond orders. Both the Prime feature and EPIK at pH=7 tools were used to fix the missing side chains and their respective generate protonation states. All the polar hydrogens were displayed in the protein chains and the protein structure was minimized using the OPLS3 force field to the default value of 0.30 Root Mean Square Deviation (RMSD).

Receptor Grid Generation: The co-crystallized ligand from the PDB protein structure was used to identify the receptor site for this study's docking protocol, with the ligand being subsequently removed from the active site. Both the atomic size (1.0 Å) and partial atomic charges (0.25) were left at the defaults. Based on the size of the ligands and the active site both internal and external receptor grid boxes of 10×10×10 and 20×20×20 Å were generated and following this protocol, all prepared ligands were docked into this grid structure for each prepared protein.

Molecular docking analysis: The optimized structures of the ligand library were docked with Schrodinger's GLIDE software using the extra precision (XP) scoring functions with both flexible protein and ligands. There were no constraints to define the ligand-receptor interactions and the output was set to pose viewer to manually inspect the docking results for proper orientations of the ligands within the receptor sites. To assess the ligands binding modes within the active site of the protein a comparison was made between both the docking score (DS) and analysis of the drug's binding mode. The DS consisted of a sum of the Glide Score but also considers the EPIK state penalty of each ligand. The DS is a measure of the binding affinity, in terms of the interaction energy between the ligand and protein and valued in kcal $mol^{-1}$ with more negative values being preferred. The threshold set for successful docking was ~7.0 kcal $mol^{-1}$ as this limit is normally used as a determinant of good ligand binding in virtual screening protocols.

Results

Like the SP-BIMs, we theorized that the SP-azaBIMs might occupy the catalytic binding domain/ATP-binding pocket of the histidine kinases and interact with the key amino acid residues within the pocket involved in binding the natural ligand. This, in turn, would inhibit the autophosphorylation of a conserved histidine residue of the protein which, via a cascade of reactions, ultimately controls the expression of certain downstream genes.

To determine whether PhoQ histidine kinase enzyme was in fact one of its molecular targets, the binding modes of the SP-azaBIMs were predicted and visually inspected using the Glide program as part of the Maestro molecular docking suite. To validate the docking protocol, the co-crystalized ligand (Radicicol) was re-docked into the ATP-binding and catalytic (CA) domain of PhoQ.

Based on the results of the docking screens, many of the SP-6azaBIM and SP7azaBIM candidate molecules displayed better Glide docking scores (GScore) to the CA domain of 3CGY than the cognate ligand (Table 15). A visual representation of the binding poses of the top 3 binders along with the cognate ligand (radicicol) are displayed in FIG. 5. It should be noted that the SP-6azaBIMs were better tighter binders than the SP-7azaBIMs. In all cased it was apparent that the two azaindole moieties were fitted within the hydrophobic pocket of the binding site, whereas the substituted phenyl rings were within the solvent exposed regions of the pocket. Key interactions were observed via the pyrrole NH- as H-bond donors to Asn 390 and Pro 419 and H-bond acceptors of the pyridine N to Asp 416 and Val 445. This may result in inhibition of autophosphorylation of the conserved His residue which then prevents phosphorylation of the response regulator, thereby switching-off genes responsible for bacterial virulence and resistance. The active SP-BIMs demonstrated the capacity to reverse bacterial resistance to several antibiotics and suppress virulence factors in MRSA, and thus may be excellent candidates for development of adjuvants for antibiotics.

TABLE 15
| Docking scores for the SP-azaBIM compounds | | |
|---|---|---|
| Compound Name | Structure | Glide Docking Score |
| SP-6azaBIM 4 | 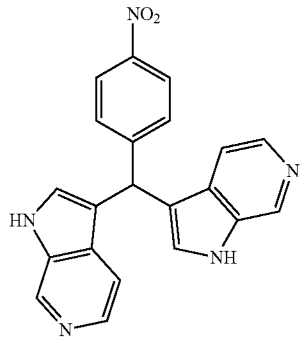 [SMILES: O=[N+]([O-])c1ccc(C(c2c[nH]c3cnccc23)c2c[nH]c3cnccc23)cc1] | −9.05 |
| SP-6azaBIM 9 | 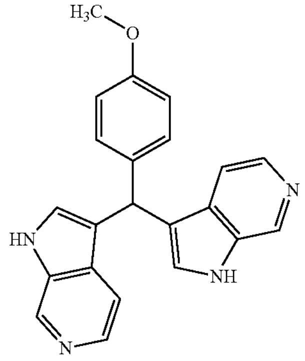 [SMILES: COc1ccc(C(c2c[nH]c3cnccc23)c2c[nH]c3cnccc23)cc1] | −8.817 |
| SP-6aza-BIM 5 | 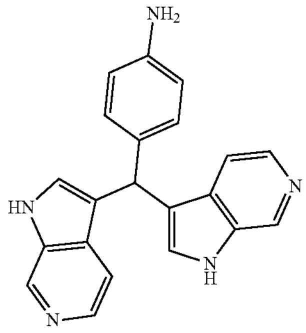 [SMILES: Nc1ccc(C(c2c[nH]c3cnccc23)c2c[nH]c3cnccc23)cc1] | −8.671 |
| SP-6aza-BIM 2 | 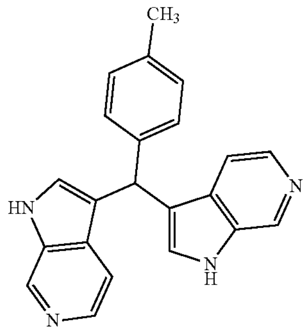 [SMILES: Cc1ccc(C(c2c[nH]c3cnccc23)c2c[nH]c3cnccc23)cc1] | −8.417 |

TABLE 15-continued
| Docking scores for the SP-azaBIM compounds | | |
|---|---|---|
| Compound Name | Structure | Glide Docking Score |
| SP-6aza-BIM 1 | 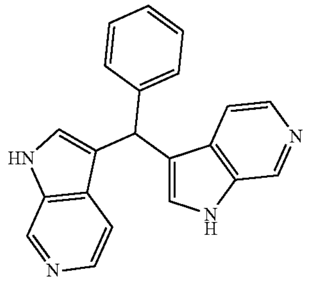 [SMILES: c1ccc(C(c2c[nH]c3cnccc23)c2c[nH]c3cnccc23)cc1] | −8.427 |
| SP-6aza-BIM 6 | 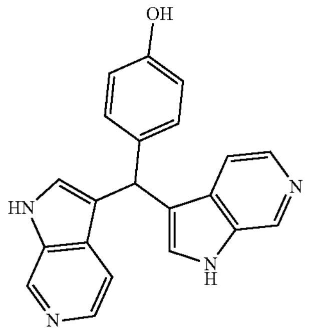 [SMILES: Oc1ccc(C(c2c[nH]c3cnccc23)c2c[nH]c3cnccc23)cc1] | −8.049 |
| SP-6aza-BIM 8 | 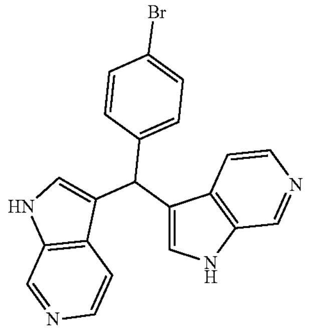 [SMILES: Brc1ccc(C(c2c[nH]c3cnccc23)c2c[nH]c3cnccc23)cc1] | −7.703 |
| SP-6aza-BIM 10 | 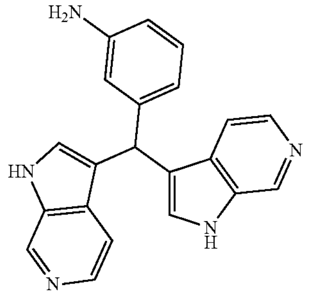 | −8.134 |

TABLE 15-continued
| Docking scores for the SP-azaBIM compounds | | |
|---|---|---|
| Compound Name | Structure | Glide Docking Score |
| SP-6aza-BIM 3 | 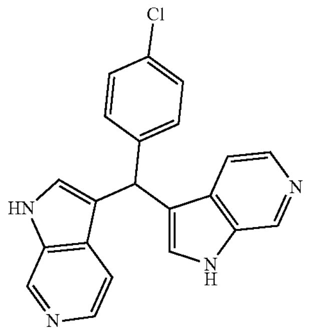 [SMILES: Clc1ccc(C(c2c[nH]c3cnccc23)c2c[nH]c3cnccc23)cc1] | −7.919 |
| SP-6aza-BIM 7 | 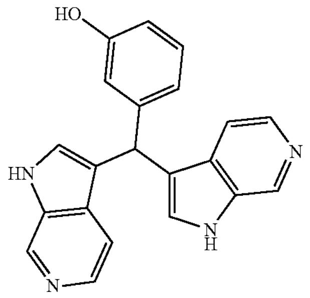 [SMILES: Oc1cccc(C(c2c[nH]c3cnccc23)c2c[nH]c3cnccc23)c1] | −7.091 |
| SP-6aza-BIM 2 | 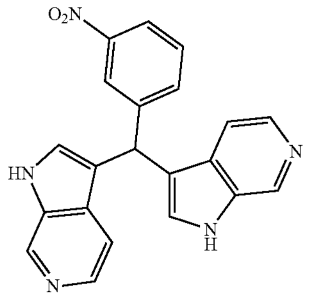 [SMILES: O=[N+]([O-])c1cccc(C(c2c[nH]c3cnccc23)c2c[nH]c3cnccc23)c1] | −7.445 |
| SP-7aza-BIM 3 | 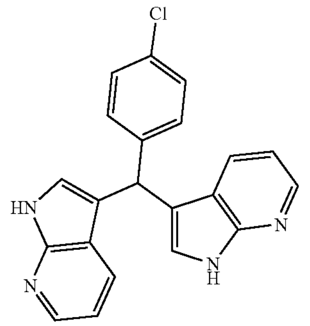 [SMILES: Clc1ccc(C(c2c[nH]c3ncccc23)c2c[nH]c3ncccc23)cc1] | −6.306 |

TABLE 15-continued
| Docking scores for the SP-azaBIM compounds | | |
|---|---|---|
| Compound Name | Structure | Glide Docking Score |
| SP-7aza-BIM 2 | 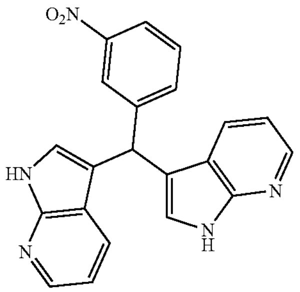 [SMILES: O=[N+]([O-])c1cccc(C(c2c[nH]c3ncccc23)c2c[nH]c3ncccc23)c1] | −5.422 |
| SP-7aza-BIM 5 | 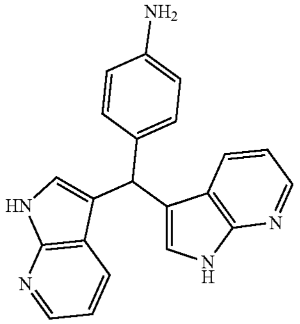 [SMILES: Nc1ccc(C(c2c[nH]c3ncccc23)c2c[nH]c3ncccc23)cc1] | −5.363 |
| SP-7aza-BIM 7 | 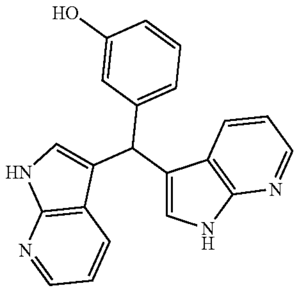 [SMILES: Oc1cccc(C(c2c[nH]c3ncccc23)c2c[nH]c3ncccc23)c1] | −5.24 |
| SP 7aza BIM 1 | 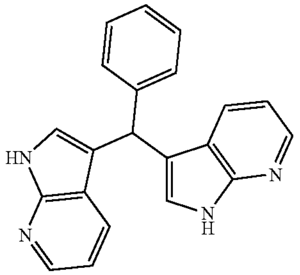 [SMILES: c1ccc(C(c2c[nH]c3ncccc23)c2c[nH]c3ncccc23)cc1] | −6.126 |
| Radicicol | 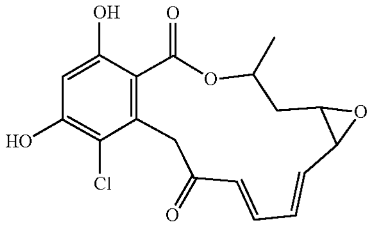 [SMILES: CC1CC2OC2/C=C/C=C/C(=O)Cc2c(Cl)c(O)cc(O)c2C(=O)O1] | −6.126 |

Example 43. Antibacterial Activity of Substituted Phenyl Azaindole Methanol

Method

Antibacterial activity of the synthesized compounds was determined following guidelines established by the Clinical and Laboratory Standards Institute M07-A10 (CLSI 2015), following the broth microdilution method. Briefly, the test articles were dissolved in 100% DMSO, diluted by 2-fold serial titrations in the same vehicle (100% DMSO), for a total of 11 concentrations. A 4 μL aliquot of each dilution was then added to 196 μL of broth medium seeded with the bacterial suspension in wells of a 96 well plate (bacterial count: $2\times10^5$ to $8\times10^5$ colony forming units/mL final). The highest test substance concentration was 1028 μg/mL, and the final vehicle concentration was 2 percent. Following incubation, the test plate was visually examined, and each well was scored for growth or complete inhibition of growth. The minimum inhibitory concentration was determined as the lowest concentration were no growth of the bacterial was observed. Each test article was assayed in duplicate.

Results

Based on the results of the broth microdilution assay (Table 16), none of the compounds displayed any direct antibacterial activity at concentrations lower than 1024 μg/mL.

TABLE 16

Antibacterial activity of substituted phenyl-azaindole derivatives

| | | Minimum inhibitory concentration (μg/mL) | | | | |
|---|---|---|---|---|---|---|
| Chemical name | Code | Methicillin resistant *Staphylococcus aureus* | Vancomycin resistant *Enterococcus faecalis* | Carbapenem resistant *Klebsiella pneumoniae* | Multidrug resistant *Pseudomonas aeruginosa* | Carbapenem resistant *Acinetobacter baumannii* |
| (2-nitrophenyl)(1H-pyrrolo[2,3-c]pyridin-3-yl)methanol | 2NO2-6aza-OH | <1024 | <1024 | <1024 | <1024 | <1024 |
| (2-nitrophenyl)(1H-pyrrolo[2,3-b]pyridin-3-yl)methanol | 2NO2-7aza-OH | <1024 | <1024 | <1024 | <1024 | <1024 |
| (5-bromo-1H-pyrrolo[2,3-c]pyridin-3-yl)(3,4-dimethoxyphenyl)methanol | 3,4 Di methoxy 5Br-6aza-OH | <1024 | <1024 | <1024 | <1024 | <1024 |
| (4-bromophenyl)(1H-pyrrolo[2,3-c]pyridin-3-yl)methanol | 3Br-6aza-OH | <1024 | <1024 | <1024 | <1024 | <1024 |
| (3-aminophenyl)(1H-pyrrolo[2,3-c]pyridin-3-yl)methanol | 3NH2-6aza-OH | <1024 | <1024 | <1024 | <1024 | <1024 |
| (5-bromo-7-chloro-1H-pyrrolo[2,3-c]pyridin-3-yl)(3-nitrophenyl)methanol | 3NO2-5Br-7Cl-6aza-OH | <1024 | <1024 | <1024 | <1024 | <1024 |
| (5-chloro-1H-pyrrolo[2,3-c]pyridin-3-yl)(3-nitrophenyl)methanol | 3NO2-5Cl-6aza-OH | <1024 | <1024 | <1024 | <1024 | <1024 |
| (5-chloro-1H-pyrrolo[2,3-b]pyridin-3-yl)(3-nitrophenyl)methanol | 3NO2-5Cl-7aza-OH | <1024 | <1024 | <1024 | <1024 | <1024 |
| (5-fluoro-1H-pyrrolo[2,3-b]pyridin-3-yl)(3-nitrophenyl)methanol | 3NO2-5Fl-7aza-OH | <1024 | <1024 | <1024 | <1024 | <1024 |
| (3-nitrophenyl)(1H-pyrrolo[2,3-c]pyridin-3-yl)methanol | 3NO2-6aza-OH | <1024 | <1024 | <1024 | <1024 | <1024 |
| (3-nitrophenyl)(1H-pyrrolo[2,3-b]pyridin-3-yl)methanol | 3NO2-7aza-OH | <1024 | <1024 | <1024 | <1024 | <1024 |
| (7-chloro-1H-pyrrolo[2,3-c]pyridin-3-yl)(3-nitrophenyl)methanol | 3NO2-7Cl-6aza | <1024 | <1024 | <1024 | <1024 | <1024 |
| 3,3'-((3-nitrophenyl)methylene)bis(1H-pyrrolo[2,3-c]pyridine) | 3NO2-Bis-6aza | <1024 | <1024 | <1024 | <1024 | <1024 |
| (5-bromo-1H-pyrrolo[2,3-c]pyridin-3-yl)(4-bromophenyl)methanol | 4Br-5Br-6aza-OH | <1024 | <1024 | <1024 | <1024 | <1024 |
| (4-bromophenyl)(5-chloro-1H-pyrrolo[2,3-c]pyridin-3-yl)methanol | 4Br-5Cl-6aza-OH | <1024 | <1024 | <1024 | <1024 | <1024 |
| (4-bromophenyl)(5-chloro-1H-pyrrolo[2,3-b]pyridin-3-yl)methanol | 4Br-5Cl-7aza-OH | <1024 | <1024 | <1024 | <1024 | <1024 |
| (4-bromophenyl)(1H-pyrrolo[2,3-c]pyridin-3-yl)methanol | 4Br-6aza-OH | <1024 | <1024 | <1024 | <1024 | <1024 |
| (4-bromophenyl)(7-chloro-1H-pyrrolo[2,3-c]pyridin-3-yl)methanol | 4Br-7Cl-6aza-OH | <1024 | <1024 | <1024 | <1024 | <1024 |
| 3,3'-((4-bromophenyl)methylene)bis(1H-pyrrolo[2,3-c]pyridine) | 4Br-Bis-6aza | <1024 | <1024 | <1024 | <1024 | <1024 |
| 4-aminophenyl)(1H-pyrrolo[2,3-c]pyridin-3-yl)methanol | 4NH2-6aza-OH | <1024 | <1024 | <1024 | <1024 | <1024 |
| (5-bromo-1H-pyrrolo[2,3-c]pyridin-3-yl)(4-nitrophenyl)methanol | 4NO2-5Br-6aza-OH | <1024 | <1024 | <1024 | <1024 | <1024 |
| (5-bromo-7-chloro-1H-pyrrolo[2,3-c]pyridin-3-yl)(4-nitrophenyl)methanol | 4NO2-5Br-7Cl-6aza-OH | <1024 | <1024 | <1024 | <1024 | <1024 |
| (5-chloro-1H-pyrrolo[2,3-c]pyridin-3-yl)(4-nitrophenyl)methanol | 4NO2-5Cl-6aza-OH | <1024 | <1024 | <1024 | <1024 | <1024 |
| (5-chloro-1H-pyrrolo[2,3-b]pyridin-3-yl)(4-nitrophenyl)methanol | 4NO2-5Cl-7aza-OH | <1024 | <1024 | <1024 | <1024 | <1024 |
| (5-fluoro-1H-pyrrolo[2,3-b]pyridin-3-yl)(4-nitrophenyl)methanol | 4NO2-5Fl-7aza-OH | <1024 | <1024 | <1024 | <1024 | <1024 |
| (4-nitrophenyl)(1H-pyrrolo[2,3-c]pyridin-3-yl)methanol | 4NO2-6aza-OH | <1024 | <1024 | <1024 | <1024 | <1024 |
| (4-nitrophenyl)(1H-pyrrolo[2,3-b]pyridin-3-yl)methanol | 4NO2-7aza-OH | <1024 | <1024 | <1024 | <1024 | <1024 |

TABLE 16-continued

Antibacterial activity of substituted phenyl-azaindole derivatives

| Chemical name | Code | Minimum inhibitory concentration (μg/mL) Methicillin resistant *Staphylococcus aureus* | Vancomycin resistant *Enterococcus faecalis* | Carbapenem resistant *Klebsiella pneumoniae* | Multidrug resistant *Pseudomonas aeruginosa* | Carbapenem resistant *Acinetobacter baumannii* |
|---|---|---|---|---|---|---|
| (7-chloro-1H-pyrrolo[2,3-c]pyridin-3-yl)(4-nitrophenyl)methanol | 4NO2-7Cl-6aza-OH | <1024 | <1024 | <1024 | <1024 | <1024 |
| 4-((5-chloro-1H-pyrrolo[2,3-c]pyridin-3-yl)(hydroxy)methyl)phenol | 4OH-5Cl-6aza-OH | <1024 | <1024 | <1024 | <1024 | <1024 |
| 4-((5-fluoro-1H-pyrrolo[2,3-b]pyridin-3-yl)(hydroxy)methyl)phenol | 4OH-5Fl-7aza-OH | <1024 | <1024 | <1024 | <1024 | <1024 |
| 4-(hydroxy(1H-pyrrolo[2,3-c]pyridin-3-yl)methyl)phenol | 4OH-6aza-OH | <1024 | <1024 | <1024 | <1024 | <1024 |
| 4-(hydroxy(1H-pyrrolo[2,3-b]pyridin-3-yl)methyl)phenol | 4OH-7aza-OH | <1024 | <1024 | <1024 | <1024 | <1024 |
| 4-(bis(5-chloro-1H-pyrrolo[2,3-c]pyridin-3-yl)methyl)phenol | 4OH-Bis 5Cl 6aza | <1024 | <1024 | <1024 | <1024 | <1024 |
| 4-(bis(5-chloro-1H-pyrrolo[2,3-b]pyridin-3-yl)methyl)phenol | 4OH-Bis 5Cl 7aza | <1024 | <1024 | <1024 | <1024 | <1024 |
| 4-(bis(1H-pyrrolo[2,3-c]pyridin-3-yl)methyl)phenol | 4OH-Bis-6aza | <1024 | <1024 | <1024 | <1024 | <1024 |
| 3-(hydroxy(1H-pyrrolo[2,3-c]pyridin-3-yl)methyl)benzaldehyde | ISO-6aza-OH | <1024 | <1024 | <1024 | <1024 | <1024 |
| 3-((7-chloro-1H-pyrrolo[2,3-c]pyridin-3-yl)(hydroxy)methyl)benzaldehyde | iso-7Cl-6aza-OH | <1024 | <1024 | <1024 | <1024 | <1024 |

Example 43. Antibiotic Adjuvant Assessment Substituted Phenyl Azaindole Derivatives Phenyl azaindole compounds are also tested for their adjuvant activities and the method is shown in Example 39. Results are shown in Table 17.

TABLE 17

Rescue concentrations of substituted phenyl azaindole derivatives.

| Code | MRSA Amoxicillin (2 μg/mL) | *K. pneumoniae* Imipenem (1 μg/mL) | *K. pneumoniae* Ciprofloxacin (1 μg/mL) | *P. aeruginosa* Imipenem (1 μg/mL) |
|---|---|---|---|---|
| 2NO2-6aza-OH | 256 | 128 | 256 | <256 |
| 2NO2-7aza-OH | 256 | <256 | <256 | <256 |
| 3,4 Di methoxy 5Br-6aza-OH | 2 | <256 | <256 | <256 |
| 3Br-6aza-OH | 1 | 4 | 4 | 32 |
| 3NH2-6aza-OH | 8 | 32 | 64 | 32 |
| 3NO2—5Br—7Cl-6aza-OH | 16 | <256 | <256 | <256 |
| 3NO2—5Cl-6aza-OH | <256 | <256 | <256 | <256 |
| 3NO2—5Cl-7aza-OH | <256 | <256 | <256 | <256 |
| 3NO2-5Fl-7aza-OH | 128 | <256 | <256 | <256 |
| 3NO2-6aza-OH | 64 | 256 | 128 | <256 |
| 3NO2-7aza-OH | <256 | <256 | <256 | <256 |
| 3NO2—7Cl-6aza-OH | 32 | <256 | <256 | <256 |
| 3NO2-Bis-6aza | <256 | <256 | <256 | <256 |
| 4Br—5Br-6aza-OH | 4 | <256 | <256 | <256 |
| 4Br—5Cl-6aza-OH | 0.5 | <256 | <256 | <256 |
| 4Br—5Cl-7aza-OH | 8 | 32 | 32 | 256 |
| 4Br-6aza-OH | 32 | 8 | 4 | 16 |
| 4Br—7Cl-6aza-OH | 2 | <256 | <256 | <256 |
| 4Br-Bis-6aza | 0.5 | 4 | 4 | 32 |
| 4NH2-6aza-OH | 8 | 16 | 64 | 128 |
| 4NO2—5Br-6aza-OH | 32 | <256 | <256 | <256 |
| 4NO2—5Br—7Cl-6aza-OH | 16 | <256 | <256 | <256 |
| 4NO2—5Cl-6aza-OH | <256 | <256 | <256 | 128 |
| 4NO2—5Cl-7aza-OH | 32 | <256 | <256 | <256 |
| 4NO2-5Fl-7aza-OH | 16 | <256 | <256 | <256 |
| 4NO2-6aza-OH | 128 | 128 | 128 | <256 |
| 4NO2-7aza-OH | 32 | <256 | <256 | <256 |
| 4NO2—7Cl-6aza-OH | 8 | <256 | <256 | <256 |
| 4OH—5Cl-6aza-OH | 16 | 256 | <256 | <256 |
| 4OH-5Fl-7aza-OH | 16 | <256 | <256 | 256 |

TABLE 17-continued

| Rescue concentrations of substituted phenyl azaindole derivatives. | | | | |
|---|---|---|---|---|
| | MRSA | *K. pneumoniae* | | *P. aeruginosa* |
| Code | Amoxicillin (2 μg/mL) | Imipenem (1 μg/mL) | Ciprofloxacin (1 μg/mL) | Imipenem (1 μg/mL) |
| 4OH-6aza-OH | 32 | <256 | <256 | 256 |
| 4OH-7aza-OH | 128 | <256 | <256 | <256 |
| 4OH-Bis 5Cl 6aza | 8 | <256 | <256 | <256 |
| 4OH-Bis 5Cl 7aza | 2 | <256 | <256 | <256 |
| 4OH-Bis-6aza | 8 | <256 | <256 | 256 |
| Iso-6aza-OH | 64 | <256 | <256 | <256 |
| Iso-7Cl-6aza-OH | 32 | <256 | <256 | <256 |

The invention claimed is:

1. A compound of Formula 2 or a pharmaceutically-acceptable salt thereof,

Ib

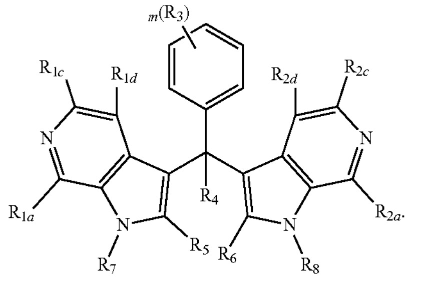

wherein $R_{1a}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{1c}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{1d}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{2a}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{2c}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

$R_{2d}$ is H, halogen, OH, CN, $OCF_3$, ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $NO_2$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, wherein said heterocycle contains at least one heteroatom selected from the group consisting of nitrogen, oxygen, and sulfur and is optionally substituted by alkyl or $OR_a$;

each occurrence of $R_3$ is independently halogen, OH, CN, CHO, $NO_2$, $OCF_3$, ($C_1$ to $C_6$) alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, aryl, 3-7-membered heterocycle, ($C_1$ to $C_6$)alkylthio, $NR_aR_b$, $(CH_2)_p$($C_3$ to $C_7$)cycloalkyl, $(CH_2)_pOR_a$, $(CH_2)_pSR_a$, $(CH_2)_pNR_aR_b$, $COOR_a$, or $CONR_aR_b$, in which said heterocycle comprises at least one heteroatom selected from the group consisting of nitrogen, oxygen and sulfur and is optionally substituted by alkyl or $OR_a$;

or alternatively two $R_3$ taken together with the ring atoms they are connected to form a 3-7-membered aromatic or heteroaromatic ring that is optionally substituted by 1-3 substituents each independently selected from the group consisting of halogen, OH, CN, ($C_1$ to $C_4$)alkyl, ($C_1$ to $C_4$)haloalkyl, and ($C_1$ to $C_4$)alkoxy;

$R_4$ is H, halogen, OH, CN, $NO_2$, $OCF_3$, ($C_1$ to $C_6$) alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, $(CH_2)_p$($C_3$ to $C_7$)cycloalkyl, $(CH_2)_pOR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_5$ is H, halogen, OH, CN, $OCF_3$, ($C_1$ to $C_6$) alkyl, ($C_1$ to $C_6$)alkoxy, ($C_3$ to $C_7$)cycloalkyl, 3-7-membered heterocycle, $NR_aR_b$, $(CH_2)_p$($C_3$ to $C_7$)cycloalkyl, $(CH_2)_pOR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_6$ is H, halogen, OH, CN, $OCF_3$, ($C_1$ to $C_6$) alkyl, ($C_1$ to $C_6$)alkoxy, ($C_3$ to $C_7$)cycloalkyl, 3-7-membered heterocycle, $NR_aR_b$, $(CH_2)_p$($C_3$ to $C_7$)cycloalkyl, $(CH_2)_pOR_a$, $(CH_2)_pSR_a$, or $(CH_2)_pNR_aR_b$, in which said heterocycle comprises at least one heteroatom selected from the group consisting of nitrogen, oxygen and sulfur and is optionally substituted by alkyl or $OR_a$;

$R_7$ is H, ($C_1$ to $C_6$) alkyl, ($C_3$ to $C_7$)cycloalkyl, 3-7-membered heterocycle, $COR_a$, $CONR_aR_b$, or $SO_2R_a$; in which said heterocycle comprises at least one heteroatom selected from the group consisting of nitrogen, oxygen and sulfur and is optionally substituted by alkyl or $OR_a$;

$R_8$ is H, ($C_1$ to $C_6$) alkyl, ($C_3$ to $C_7$)cycloalkyl, 3-7-membered heterocycle, $COR_a$, $CONR_aR_b$, or $SO_2R_a$; in which said heterocycle comprises at least one heteroatom selected from the group consisting of nitrogen, oxygen and sulfur and is optionally substituted by alkyl or $OR_a$;

each occurrence of $R_a$ and $R_b$ are each independently H, ($C_1$ to $C_6$)alkyl, ($C_2$ to $C_6$)alkenyl, or ($C_3$ to $C_7$)cycloalkyl;

the alkyl, alkenyl, alkynal, alkoxy, cycloalkyl, aryl, heterocycle, and alkylthio in $R_{1a}$, $R_{1b}$, $R_{1c}$, $R_{1d}$, $R_{2a}$, $R_{2b}$, $R_{2c}$, $R_{2a}$, $R_3$, $R_4$, $R_5$, $R_6$, $R_7$, or $R_8$, where applicable, are optionally substituted by 1-3 substituents each independently selected from the group consisting of halogen, OH, CN, ($C_1$ to $C_4$)alkyl, ($C_1$ to $C_4$)haloalkyl, and ($C_1$ to $C_4$)alkoxy;

m is an integer from 1-5; and each occurrence of p is independently an integer from 1-4.

2. The compound according to claim 1, wherein $R_{1a}$ is H, halogen, OH, CN, $OCF_3$, $NR_aR_b$, $NO_2$, $COOR_a$, or $CONR_aR_b$.

3. The compound according to claim 1, wherein $R_{1a}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

4. The compound according to claim 1, wherein $R_{1a}$ is ($C_3$ to $C_7$)cycloalkyl, 3-7-membered heterocycle, or $(CH_2)_p$($C_3$ to $C_7$)cycloalkyl.

5. The compound according to claim 1, wherein $R_{1a}$ is H, OH, $OCH_3$, F, Cl, or Br.

6. The compound according to claim 1, wherein $R_{1c}$ is H, halogen, OH, CN, $OCF_3$, $NR_aR_b$, $NO_2$, $COOR_a$, or $CONR_aR_b$.

7. The compound according to claim 1, wherein $R_{1c}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

8. The compound according to claim 1, wherein $R_{1c}$ is ($C_3$ to $C_7$)cycloalkyl, 3-7-membered heterocycle, or $(CH_2)_p$($C_3$ to $C_7$)cycloalkyl.

9. The compound according to claim 1, wherein $R_{1c}$ is H, OH, $OCH_3$, F, Cl, or Br.

10. The compound according to claim 1, wherein $R_{1d}$ is H, halogen, OH, CN, $OCF_3$, $NR_aR_b$, $NO_2$, $COOR_a$, or $CONR_aR_b$.

11. The compound according to claim 1, wherein $R_{1d}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

12. The compound according to claim 1, wherein $R_{1d}$ is ($C_3$ to $C_7$)cycloalkyl, 3-7-membered heterocycle, or $(CH_2)_p$($C_3$ to $C_7$)cycloalkyl.

13. The compound according to claim 1, wherein $R_{1d}$ is H, OH, $OCH_3$, F, Cl, or Br.

14. The compound according to claim 1, wherein $R_{2a}$ is H, halogen, OH, CN, $OCF_3$, $NR_aR_b$, $NO_2$, $COOR_a$, or $CONR_aR_b$.

15. The compound according to claim 1, wherein $R_{2a}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

16. The compound according to claim 1, wherein $R_{2a}$ is ($C_3$ to $C_7$)cycloalkyl, 3-7-membered heterocycle, or $(CH_2)_p$($C_3$ to $C_7$)cycloalkyl.

17. The compound according to claim 1, wherein $R_{2a}$ is H, OH, $OCH_3$, F, Cl, or Br.

18. The compound according to claim 1, wherein $R_{2c}$ is H, halogen, OH, CN, $OCF_3$, $NR_aR_b$, $NO_2$, $COOR_a$, or $CONR_aR_b$.

19. The compound according to claim 1, wherein $R_{2c}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

20. The compound according to claim 1, wherein $R_{2c}$ is ($C_3$ to $C_7$)cycloalkyl, 3-7-membered heterocycle, or $(CH_2)_p$($C_3$ to $C_7$)cycloalkyl.

21. The compound according to claim 1, wherein $R_{2c}$ is H, OH, $OCH_3$, F, Cl, or Br.

22. The compound according to claim 1, wherein $R_{2d}$ is H, halogen, OH, CN, $OCF_3$, $NR_aR_b$, $NO_2$, $COOR_a$, or $CONR_aR_b$.

23. The compound according to claim 1, wherein $R_{2d}$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

24. The compound according to claim 1, wherein $R_{2d}$ is ($C_3$ to $C_7$)cycloalkyl, 3-7-membered heterocycle, or $(CH_2)_p$($C_3$ to $C_7$)cycloalkyl.

25. The compound according to claim 1, wherein $R_{2d}$ is H, OH, $OCH_3$, F, Cl, or Br.

26. The compound according to claim 1, wherein at least one occurrence of $R_3$ is halogen, OH, CN, $OCF_3$, CHO, $NO_2$, $NH_2$, $COOR_a$, or $CONR_aR_b$.

27. The compound according to claim 1, wherein at least one occurrence of $R_3$ is ($C_1$ to $C_6$)alkyl, halogenated ($C_1$ to $C_6$)alkyl, ($C_2$ to $C_6$)alkenyl, ($C_2$ to $C_6$)alkynyl, ($C_1$ to $C_6$)alkoxy, ($C_1$ to $C_6$)alkylthio, $(CH_2)_pOR_a$, $(CH_2)_pSR_a$, or $(CH_2)_pNR_aR_b$.

28. The compound according to claim 1, wherein at least one occurrence of $R_3$ is ($C_3$ to $C_7$)cycloalkyl, 3-7-membered heterocycle, or $(CH_2)_p$($C_3$ to $C_7$)cycloalkyl.

29. The compound according to claim 1, wherein at least one occurrence of $R_3$ is OH, $OCH_3$, F, Cl, or Br.

30. The compound according to claim 1, wherein at least one occurrence of $R_3$ is OH.

31. The compound according to claim 1, wherein at least one occurrence of $R_3$ is Br, F, or Cl.

32. The compound according to claim 1, wherein at least one occurrence of $R_3$ is $NO_2$ or $NH_2$.

33. The compound according to claim 1, wherein at least one occurrence of $R_3$ is $CH_3$, $CH_2CH_3$, $CH(CH_3)_2$, $CH_2CH_2CH_3$, $OCH_3$, $OCH_2CH_3$, $OCH(CH_3)_2$, $OCH_2CH_2CH_3$, or CHO.

34. The compound according to claim 1, wherein m is 1.

35. The compound according to claim 1, wherein m is 2.

36. The compound according to claim 1, wherein m is 3.

37. The compound according to claim 1, wherein the structural moiety

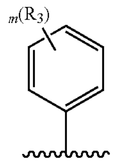

has the structure of

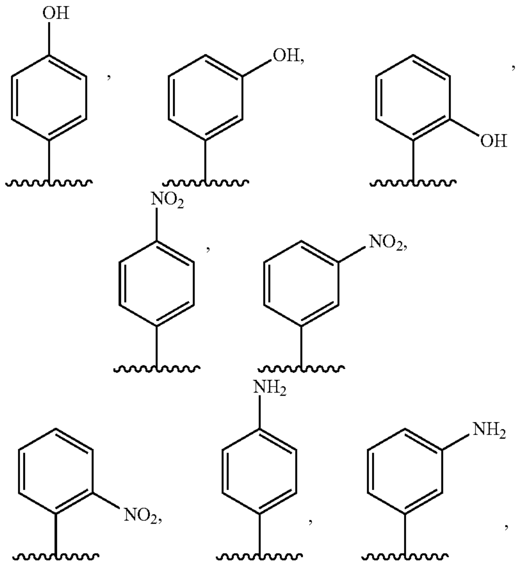

-continued

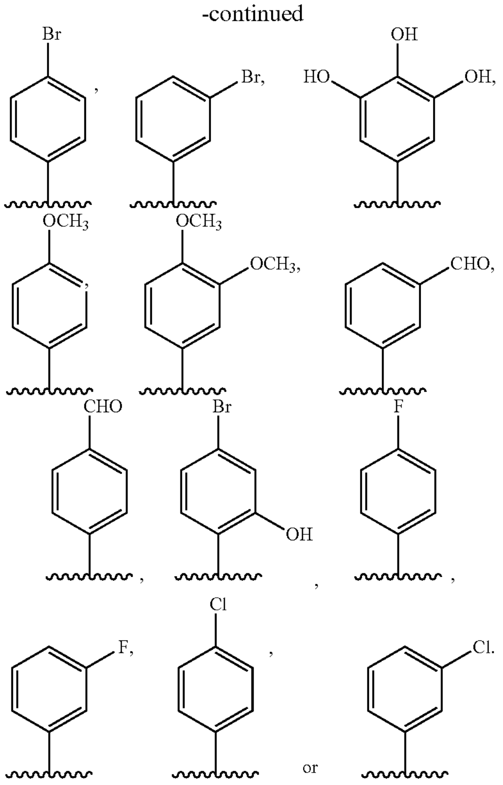

38. The compound according to claim 1, wherein $R_4$ is H, halogen, OH, CN, $OCF_3$, $NR_aR_b$, ($C_1$ to $C_6$) alkyl, ($C_1$ to $C_6$)alkoxy, $(CH_2)_pOR_a$, $(CH_2)_pSR_a$, or $(CH_2)_pNR_aR_b$.

39. The compound according to claim 1, wherein $R_4$ is H, Cl, F, Br, OH, $CH_3$, $OCH_3$, $OCF_3$, or $CH_2CH_3$.

40. The compound according to claim 1, wherein $R_5$ is H, halogen, OH, CN, $OCF_3$, $NR_aR_b$, ($C_1$ to $C_6$) alkyl, ($C_1$ to $C_6$)alkoxy, $(CH_2)_pOR_a$, $(CH_2)_pSR_a$, or $(CH_2)_pN_RaR_b$.

41. The compound according to claim 1, wherein $R_5$ is H, Cl, F, Br, $CH_3$, $OCH_3$, $OCF_3$, or $CH_2CH_3$.

42. The compound according to claim 1, wherein $R_6$ is H, halogen, OH, CN, $OCF_3$, $NR_aR_b$, ($C_1$ to $C_6$) alkyl, ($C_1$ to $C_6$)alkoxy, $(CH_2)_pOR_a$, $(CH_2)_pSR_a$, or $(CH_2)_pNR_aR_b$.

43. The compound according to claim 1, wherein $R_6$ is H, Cl, F, Br, $CH_3$, $OCH_3$, $OCF_3$, or $CH_2CH_3$.

44. The compound according to claim 1, wherein $R_7$ is H, ($C_1$ to $C_6$) alkyl, ($C_3$ to $C_7$)cycloalkyl, $COR_a$, $CONR_aR_b$, or $SO_2R_a$.

45. The compound according to claim 1, wherein $R_7$ is H, $CH_3$, $CH_2CH_3$, C(=O)$CH_3$, or C(=O)$NHCH_3$.

46. The compound according to claim 1, wherein $R_8$ is H, ($C_1$ to $C_6$) alkyl, ($C_3$ to $C_7$)cycloalkyl, $COR_a$, $CONR_aR_b$, or $SO_2R_a$.

47. The compound according to claim 1, wherein $R_8$ is H, $CH_3$, $CH_2CH_3$, C(=O)$CH_3$, or C(=O)$NHCH_3$.

48. The compound according to claim 1, wherein at least one occurrence of p is 1.

49. The compound according to claim 1, wherein at least one occurrence of p is 2 or 3.

50. The compound according to claim 1, wherein $R_{1a}$ is independently H, halogen, OH, CN, $OCF_3$, ($C_1$ to $C_6$) alkyl, or ($C_1$ to $C_6$)alkoxy; $R_{1c}$ is independently H, halogen, OH, CN, $OCF_3$, ($C_1$ to $C_6$) alkyl, or ($C_1$ to $C_6$)alkoxy; $R_{1d}$ is independently H, halogen, OH, CN, $OCF_3$, ($C_1$ to $C_6$) alkyl, or ($C_1$ to $C_6$)alkoxy; $R_{2a}$ is independently H, halogen, OH, CN, $OCF_3$, ($C_1$ to $C_6$) alkyl, or ($C_1$ to $C_6$)alkoxy; $R_{2c}$ is independently H, halogen, OH, CN, $OCF_3$, ($C_1$ to $C_6$) alkyl, or ($C_1$ to $C_6$)alkoxy; and $R_{2d}$ is independently H, halogen, OH, CN, $OCF_3$, ($C_1$ to $C_6$) alkyl, or ($C_1$ to $C_6$)alkoxy.

51. The compound according to claim 50, wherein each occurrence of $R_3$ is independently OH, halogen, CN, $NH_2$, $NO_2$, $OCF_3$, ($C_1$ to $C_6$) alkyl, ($C_1$ to $C_6$)alkoxy, or CHO; $R_4$ is H, halogen, OH, CN, $OCF_3$, ($C_1$ to $C_6$) alkyl, or ($C_1$ to $C_6$)alkoxy; $R_5$ is H, halogen, OH, CN, $OCF_3$, ($C_1$ to $C_6$) alkyl, or ($C_1$ to $C_6$)alkoxy; $R_6$ is H, halogen, OH, CN, $OCF_3$, ($C_1$ to $C_6$) alkyl, or ($C_1$ to $C_6$)alkoxy; $R_7$ is H, ($C_1$ to $C_6$) alkyl, $COR_a$, or $CONR_aR_b$; and $R_8$ is H, ($C_1$ to $C_6$) alkyl, $COR_a$, or $CONR_aR_b$.

52. The compound according to claim 1, wherein the compound is selected from the group consisting of compounds 34-37 and 39-59 as shown in Table A,

TABLE A

| Compound No. | Compound Structure |
|---|---|
| 34 | 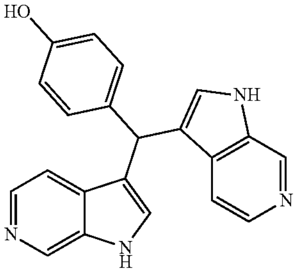 [SMILES: Oc1ccc(C(c2c[nH]c3cnccc23)c2c[nH]c3cnccc23)cc1] |
| 35 | 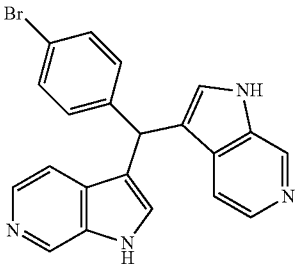 [SMILES: Brc1ccc(C(c2c[nH]c3cnccc23)c2c[nH]c3cnccc23)cc1] |
| 36 | 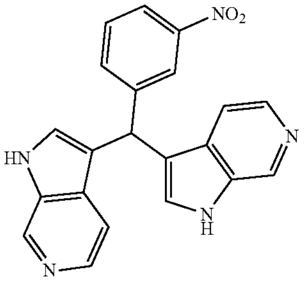 [SMILES: O=[N+]([O-])c1cccc(C(c2c[nH]c3cnccc23)c2c[nH]c3cnccc23)c1] |
| 37 | 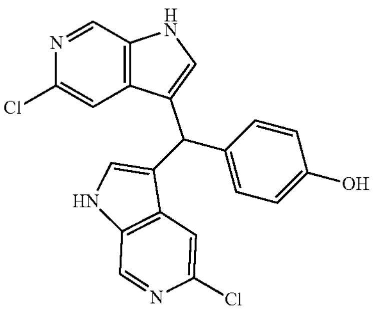 [SMILES: Oc1ccc(C(c2c[nH]c3cnc(Cl)cc23)c2c[nH]c3cnc(Cl)cc23)cc1] |

TABLE A-continued

| Compound No. | Compound Structure |
|---|---|
| 39 | 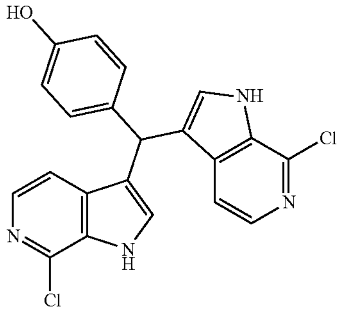 |
| 40 | 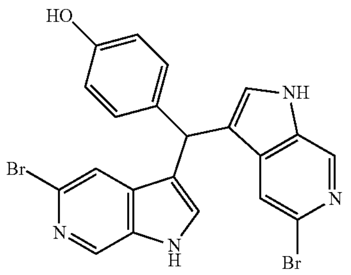 [SMILES: Oc1ccc(C(c2c[nH]c3cnc(Br)cc23)c2c[nH]c3cnc(Br)cc23)cc1] |
| 41 | 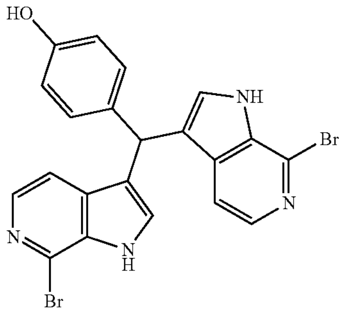 [SMILES: Oc1ccc(C(c2c[nH]c3c(Br)nccc23)c2c[nH]c3c(Br)nccc23)cc1] |
| 42 | 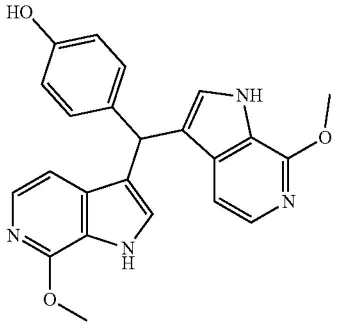 [SMILES: COc1nccc2c(C(c3ccc(O)cc3)c3c[nH]c4c(OC)nccc34)c[nH]c12] |
| 43 | 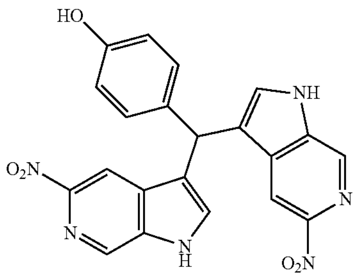 [SMILES: O=[N+]([O-])c1cc2c(C(c3ccc(O)cc3)c3c[nH]c4cnc([N+](=O)[O-])cc34)c[nH]c2cn1] |

TABLE A-continued
| Compound No. | Compound Structure |
| --- | --- |
| 44 | 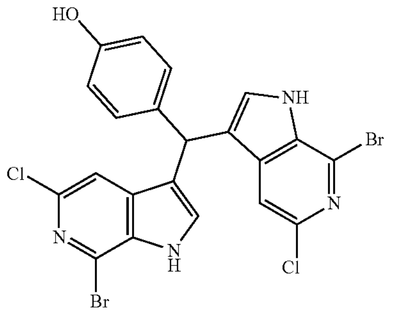 [SMILES: Oc1ccc(C(c2c[nH]c3c(Br)nc(Cl)cc23)c2c[nH]c3c(Br)nc(Cl)cc23)cc1] |
| 45 | 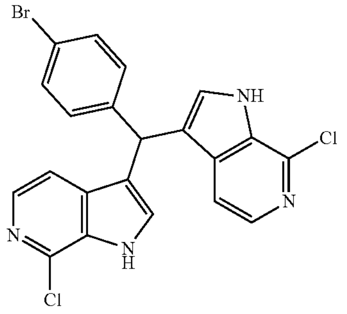 [SMILES: Clc1nccc2c(C(c3ccc(Br)cc3)c3c[nH]c4c(Cl)nccc34)c[nH]c12] |
| 46 | 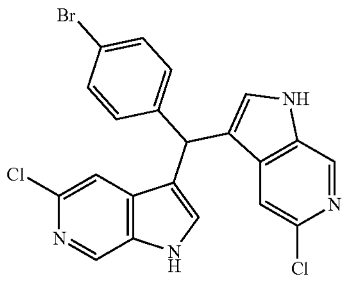 [SMILES: Clc1cc2c(C(c3ccc(Br)cc3)c3c[nH]c4cnc(Cl)cc34)c[nH]c2cn1] |
| 47 | 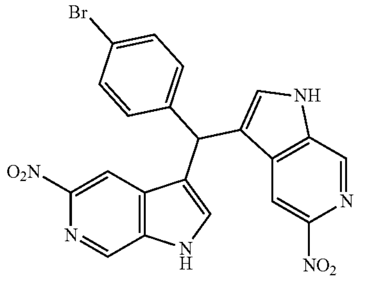 [SMILES: O=[N+]([O-])c1cc2c(C(c3ccc(Br)cc3)c3c[nH]c4cnc([N+](=O)[O-])cc34)c[nH]c2cn1] |
| 48 | 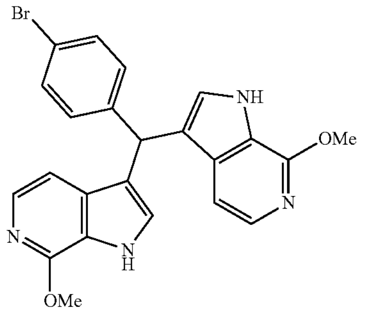 [SMILES: COc1nccc2c(C(c3ccc(Br)cc3)c3c[nH]c4c(OC)nccc34)c[nH]c12] |
TABLE A-continued
| Compound No. | Compound Structure |
| --- | --- |
| 49 | 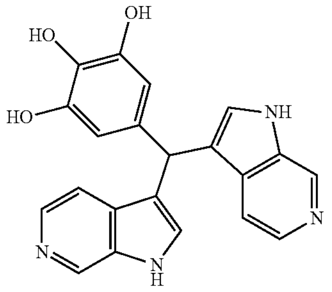 [SMILES: Oc1cc(C(c2c[nH]c3cnccc23)c2c[nH]c3cnccc23)cc(O)c1O] |
| 50 | 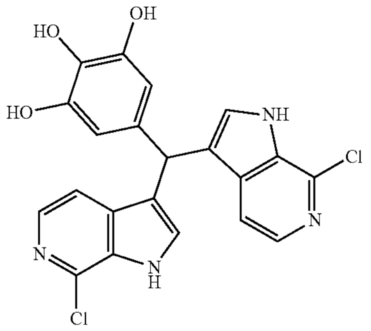 [SMILES: Oc1cc(C(c2c[nH]c3c(Cl)nccc23)c2c[nH]c3c(Cl)nccc23)cc(O)c1O] |
| 51 | 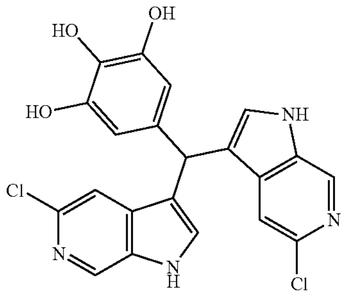 [SMILES: Oc1cc(C(c2c[nH]c3cnc(Cl)cc23)c2c[nH]c3cnc(Cl)cc23)cc(O)c1O] |
| 52 | 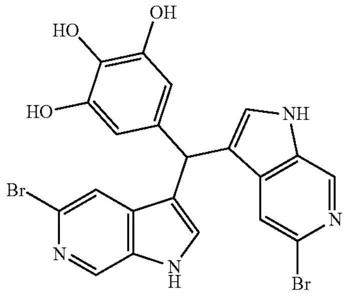 |
| 53 | 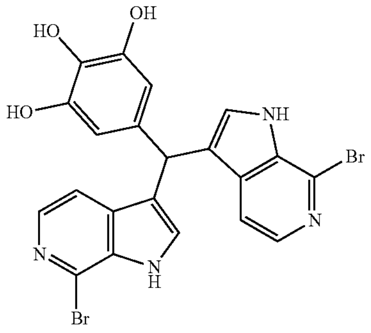 [SMILES: Oc1cc(C(c2c[nH]c3c(Br)nccc23)c2c[nH]c3c(Br)nccc23)cc(O)c1O] |

TABLE A-continued

| Compound No. | Compound Structure |
|---|---|
| 54 | 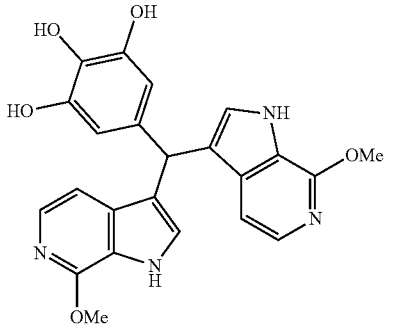 [SMILES: COc1nccc2c(C(c3cc(O)c(O)c(O)c3)c3c[nH]c4c(OC)nccc34)c[nH]c12] |
| 55 | 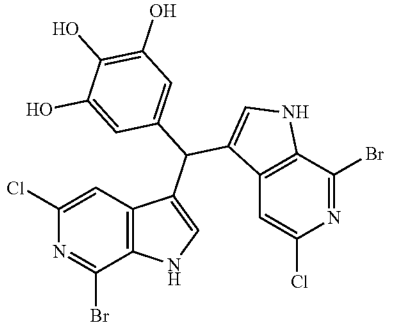 [SMILES: Oc1cc(C(c2c[nH]c3c(Br)nc(Cl)cc23)c2c[nH]c3c(Br)nc(Cl)cc23)cc(O)c1O] |
| 56 | 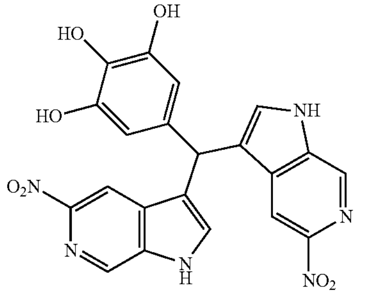 [SMILES: O=[N+]([O-])c1cc2c(C(c3cc(O)c(O)c(O)c3)c3c[nH]c4cnc([N+](=O)[O-])cc34)c[nH]c2cn1] |
| 57 | 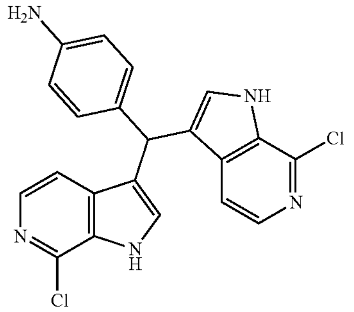 |
| 58 | 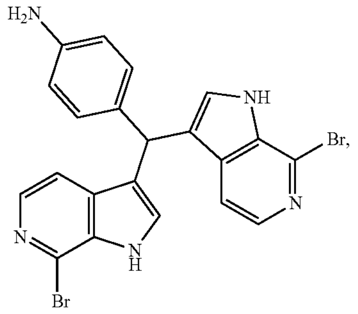 and |

TABLE A-continued

| Compound No. | Compound Structure |
|---|---|
| 59 | 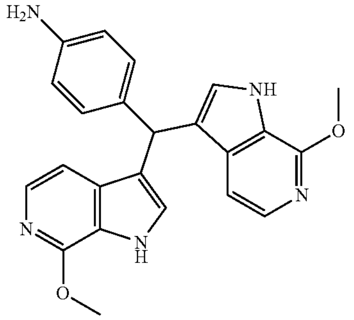 [SMILES: COc1nccc2c(C(c3ccc(N)cc3)c3c[nH]c4c(OC)nccc34)c[nH]c12] |

53. A pharmaceutical composition comprising at least one compound according to claim 1 or a pharmaceutically-acceptable salt thereof.

54. The pharmaceutical composition according to claim 53, further comprising an antimicrobial agent.

55. The pharmaceutical composition according to claim 54, wherein the antimicrobial agent is an antibacterial agent.

56. The pharmaceutical composition according to claim 54, wherein the antimicrobial agent is an antifungal agent.

57. The pharmaceutical composition according to claim 54, wherein the antimicrobial agent is a macrolide, a folic acid synthesis inhibitor, a fluoroquinolone, an aminoglycoside, a monobactam, a cephalosporin, a glycopeptide, a β-lactam, a carbapenem, or a tetracycline.

58. The pharmaceutical composition according to claim 54, wherein the antimicrobial agent is selected from the group consisting of ampicillin, imipenem, cephalexin, erythromycin, aztreonam, trimethoprim, streptomycin, ciprofloxacin, meropenem, vancomycin, doxycycline, chloramphenicol, and kanamycin.

59. The pharmaceutical composition according to claim 54, wherein the compound is selected from the group consisting of compounds 34-37 and 39-59 as shown in Table A, and the antimicrobial agent is selected from the group consisting of ampicillin, imipenem, cephalexin, erythromycin, streptomycin, ciprofloxacin, meropenem, vancomycin, doxycycline, and kanamycin,

TABLE A

| Compound No. | Compound Structure |
|---|---|
| 34 | 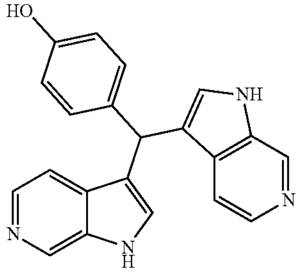 [SMILES: Oc1ccc(C(c2c[nH]c3cnccc23)c2c[nH]c3cnccc23)cc1] |

TABLE A-continued
| Compound No. | Compound Structure |
|---|---|
| 35 | 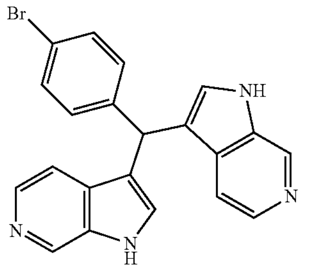 [SMILES: Brc1ccc(C(c2c[nH]c3cnccc23)c2c[nH]c3cnccc23)cc1] |
| 36 | 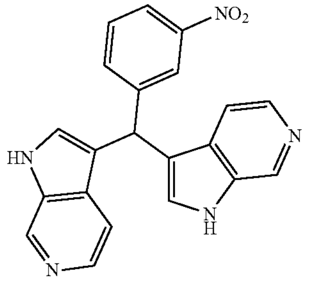 [SMILES: O=[N+]([O-])c1cccc(C(c2c[nH]c3cnccc23)c2c[nH]c3cnccc23)c1] |
| 37 | 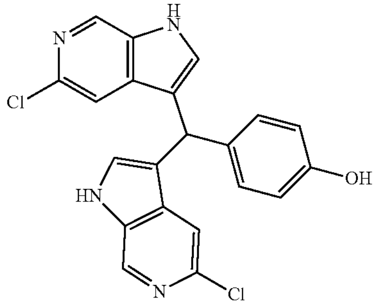 [SMILES: Oc1ccc(C(c2c[nH]c3cnc(Cl)cc23)c2c[nH]c3cnc(Cl)cc23)cc1] |
| 39 | 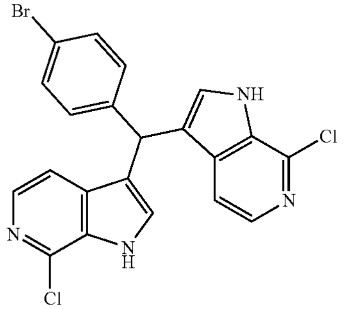 [SMILES: Clc1nccc2c(C(c3ccc(Br)cc3)c3c[nH]c4c(Cl)nccc34)c[nH]c12] |
| 40 | 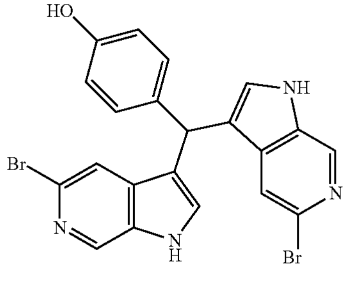 |
TABLE A-continued
| Compound No. | Compound Structure |
|---|---|
| 41 | 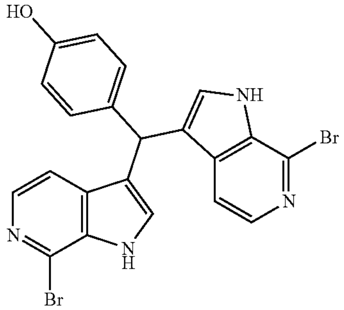 [SMILES: Oc1ccc(C(c2c[nH]c3c(Br)nccc23)c2c[nH]c3c(Br)nccc23)cc1] |
| 42 | 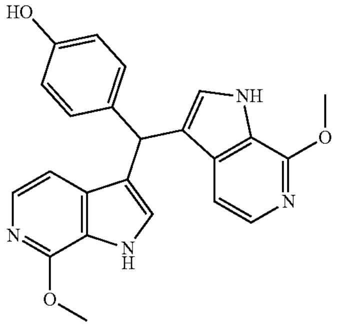 [SMILES: COc1nccc2c(C(c3ccc(O)cc3)c3c[nH]c4c(OC)nccc34)c[nH]c12] |
| 43 | 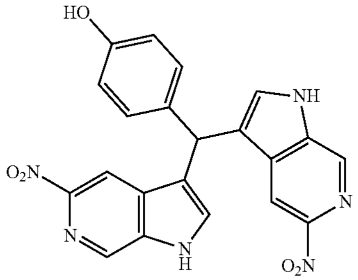 [SMILES: O=[N+]([O-])c1cc2c(C(c3ccc(O)cc3)c3c[nH]c4cnc([N+](=O)[O-])cc34)c[nH]c2cn1] |
| 44 | 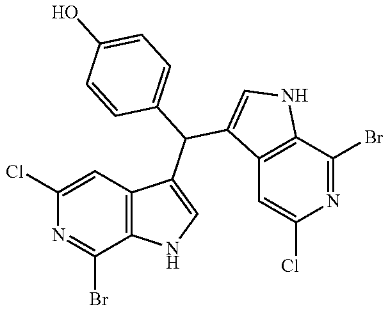 [SMILES: Oc1ccc(C(c2c[nH]c3c(Br)nc(Cl)cc23)c2c[nH]c3c(Br)nc(Cl)cc23)cc1] |
| 45 | 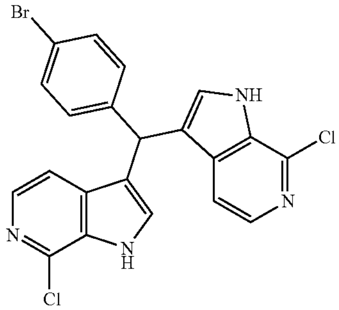 [SMILES: Clc1nccc2c(C(c3ccc(Br)cc3)c3c[nH]c4c(Cl)nccc34)c[nH]c12] |

TABLE A-continued
| Compound No. | Compound Structure |
| --- | --- |
| 46 | 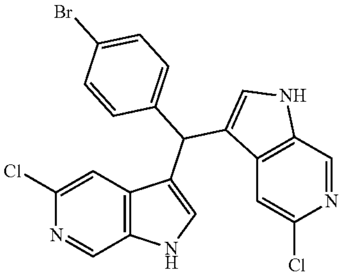 [SMILES: Clc1cc2c(C(c3ccc(Br)cc3)c3c[nH]c4cnc(Cl)cc34)c[nH]c2cn1] |
| 47 | 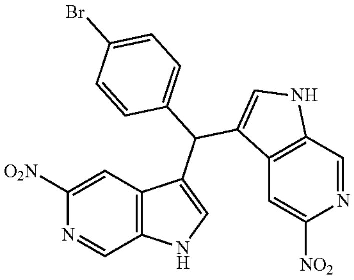 [SMILES: O=[N+]([O-])c1cc2c(C(c3ccc(Br)cc3)c3c[nH]c4cnc([N+](=O)[O-])cc34)c[nH]c2cn1] |
| 48 | 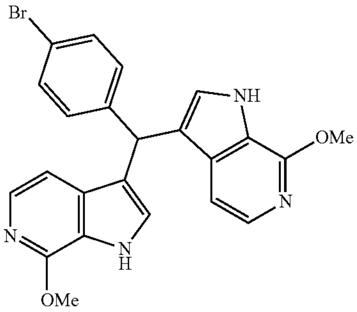 [SMILES: COc1nccc2c(C(c3ccc(Br)cc3)c3c[nH]c4c(OC)nccc34)c[nH]c12] |
| 49 | 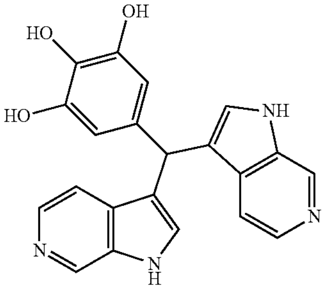 [SMILES: Oc1cc(C(c2c[nH]c3cnccc23)c2c[nH]c3cnccc23)cc(O)c1O] |
| 50 | 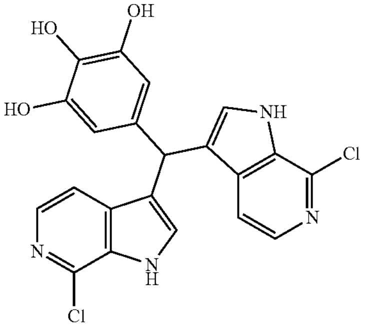 [SMILES: Oc1cc(C(c2c[nH]c3c(Cl)nccc23)c2c[nH]c3c(Cl)nccc23)cc(O)c1O] |
TABLE A-continued
| Compound No. | Compound Structure |
| --- | --- |
| 51 | 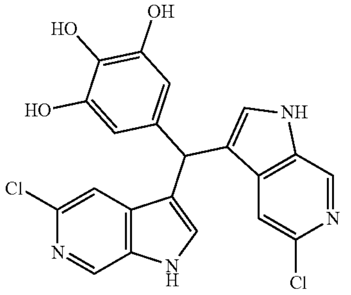 [SMILES: Oc1cc(C(c2c[nH]c3cnc(Cl)cc23)c2c[nH]c3cnc(Cl)cc23)cc(O)c1O] |
| 52 | 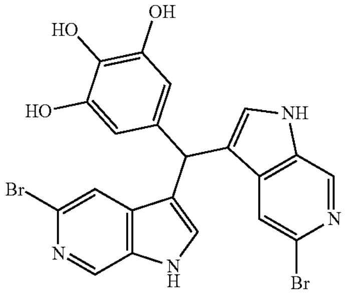 |
| 53 | 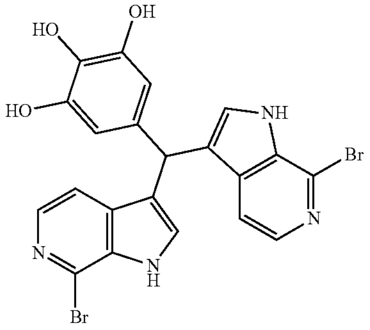 [SMILES: Oc1cc(C(c2c[nH]c3c(Br)nccc23)c2c[nH]c3c(Br)nccc23)cc(O)c1O] |
| 54 | 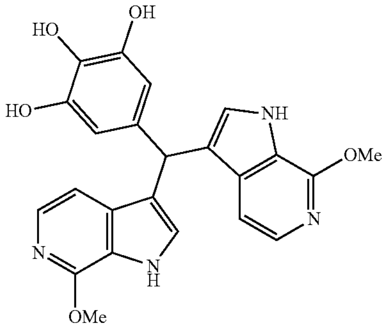 [SMILES: COc1nccc2c(C(c3cc(O)c(O)c(O)c3)c3c[nH]c4c(OC)nccc34)c[nH]c12] |
| 55 | 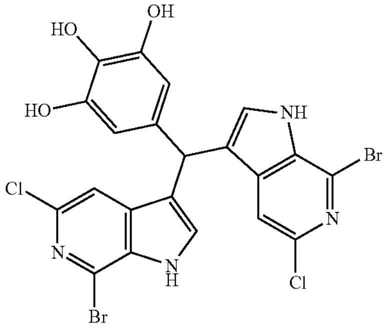 [SMILES: Oc1cc(C(c2c[nH]c3c(Br)nc(Cl)cc23)c2c[nH]c3c(Br)nc(Cl)cc23)cc(O)c1O] |

TABLE A-continued
| Compound No. | Compound Structure |
|---|---|
| 56 | 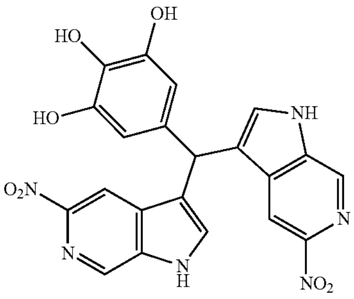 [SMILES: O=[N+]([O-])c1cc2c(C(c3cc(O)c(O)c(O)c3)c3c[nH]c4cnc([N+](=O)[O-])cc34)c[nH]c2cn1] |
| 57 | 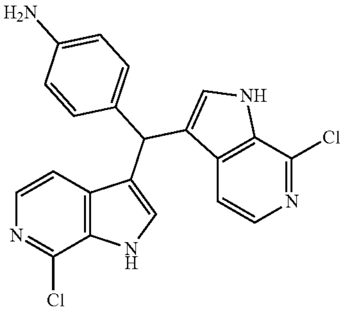 |
| 58 | 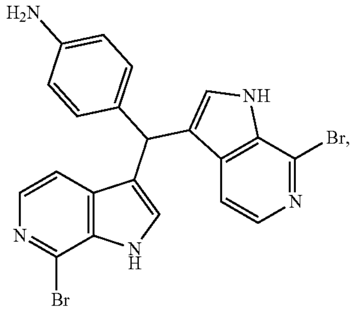 [SMILES: Nc1ccc(C(c2c[nH]c3c(Br)nccc23)c2c[nH]c3c(Br)nccc23)cc1], and |
| 59 | 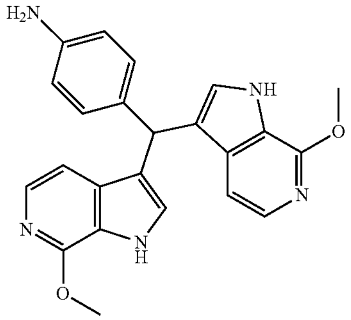 [SMILES: COc1nccc2c(C(c3ccc(N)cc3)c3c[nH]c4c(OC)nccc34)c[nH]c12] |
60. The pharmaceutical composition according to claim 53, further comprising one or more pharmaceutically acceptable excipients.
* * * * *

SEQUENCE LISTING

```
Sequence total quantity: 30
SEQ ID NO: 1           moltype = DNA  length = 20
FEATURE                Location/Qualifiers
source                 1..20
                       mol_type = other DNA
                       organism = synthetic construct
SEQUENCE: 1
caaagaacat accgggcagc                                                  20

SEQ ID NO: 2           moltype = DNA  length = 20
FEATURE                Location/Qualifiers
source                 1..20
                       mol_type = other DNA
                       organism = synthetic construct
SEQUENCE: 2
cgttcaggat cggctcgtta                                                  20

SEQ ID NO: 3           moltype = DNA  length = 20
FEATURE                Location/Qualifiers
source                 1..20
                       mol_type = other DNA
                       organism = synthetic construct
SEQUENCE: 3
cagaccttta cccgcgtctt                                                  20

SEQ ID NO: 4           moltype = DNA  length = 20
FEATURE                Location/Qualifiers
source                 1..20
                       mol_type = other DNA
                       organism = synthetic construct
SEQUENCE: 4
actgtggttc tctttgcggt                                                  20

SEQ ID NO: 5           moltype = DNA  length = 20
FEATURE                Location/Qualifiers
source                 1..20
                       mol_type = other DNA
                       organism = synthetic construct
SEQUENCE: 5
agaaagagac cggccattcc                                                  20

SEQ ID NO: 6           moltype = DNA  length = 20
FEATURE                Location/Qualifiers
source                 1..20
                       mol_type = other DNA
                       organism = synthetic construct
SEQUENCE: 6
tgctgcgact cgaaaccata                                                  20

SEQ ID NO: 7           moltype = DNA  length = 20
FEATURE                Location/Qualifiers
source                 1..20
                       mol_type = other DNA
                       organism = synthetic construct
SEQUENCE: 7
tcaacgggaa acgtcttgct                                                  20

SEQ ID NO: 8           moltype = DNA  length = 20
```

```
FEATURE                Location/Qualifiers
source                 1..20
                       mol_type = other DNA
                       organism = synthetic construct
SEQUENCE: 8
tcgcgagccc atttataccc                                              20

SEQ ID NO: 9           moltype = DNA  length = 20
FEATURE                Location/Qualifiers
source                 1..20
                       mol_type = other DNA
                       organism = synthetic construct
SEQUENCE: 9
agcaacgatt ccgtcacact                                              20

SEQ ID NO: 10          moltype = DNA  length = 20
FEATURE                Location/Qualifiers
source                 1..20
                       mol_type = other DNA
                       organism = synthetic construct
SEQUENCE: 10
ccccaccact cgacgatatg                                              20

SEQ ID NO: 11          moltype = DNA  length = 20
FEATURE                Location/Qualifiers
source                 1..20
                       mol_type = other DNA
                       organism = synthetic construct
SEQUENCE: 11
cgccactctc ccaatcagtt                                              20

SEQ ID NO: 12          moltype = DNA  length = 20
FEATURE                Location/Qualifiers
source                 1..20
                       mol_type = other DNA
                       organism = synthetic construct
SEQUENCE: 12
aaaagacgag cacggagaca                                              20

SEQ ID NO: 13          moltype = DNA  length = 20
FEATURE                Location/Qualifiers
source                 1..20
                       mol_type = other DNA
                       organism = synthetic construct
SEQUENCE: 13
agatcagttg ggtgcacgag                                              20

SEQ ID NO: 14          moltype = DNA  length = 20
FEATURE                Location/Qualifiers
source                 1..20
                       mol_type = other DNA
                       organism = synthetic construct
SEQUENCE: 14
ggggcgaaaa ctctcaagga                                              20

SEQ ID NO: 15          moltype = DNA  length = 20
FEATURE                Location/Qualifiers
source                 1..20
                       mol_type = other DNA
                       organism = synthetic construct
SEQUENCE: 15
gcagccgctt gagcaaatta                                              20

SEQ ID NO: 16          moltype = DNA  length = 20
FEATURE                Location/Qualifiers
source                 1..20
                       mol_type = other DNA
                       organism = synthetic construct
SEQUENCE: 16
tgctcatcat gggaaagcgt                                              20

SEQ ID NO: 17          moltype = DNA  length = 20
FEATURE                Location/Qualifiers
source                 1..20
                       mol_type = other DNA
                       organism = synthetic construct
SEQUENCE: 17
atcgccgtct agttctgctg                                              20
```

-continued

```
SEQ ID NO: 18           moltype = DNA  length = 20
FEATURE                 Location/Qualifiers
source                  1..20
                        mol_type = other DNA
                        organism = synthetic construct
SEQUENCE: 18
tatccatcgc gtacacaccg                                              20

SEQ ID NO: 19           moltype = DNA  length = 20
FEATURE                 Location/Qualifiers
source                  1..20
                        mol_type = other DNA
                        organism = synthetic construct
SEQUENCE: 19
gcgataaatg gctggtgctg                                              20

SEQ ID NO: 20           moltype = DNA  length = 20
FEATURE                 Location/Qualifiers
source                  1..20
                        mol_type = other DNA
                        organism = synthetic construct
SEQUENCE: 20
tccgttattg ttgacggcga                                              20

SEQ ID NO: 21           moltype = DNA  length = 20
FEATURE                 Location/Qualifiers
source                  1..20
                        mol_type = other DNA
                        organism = synthetic construct
SEQUENCE: 21
cggagaacaa aatcggcgtc                                              20

SEQ ID NO: 22           moltype = DNA  length = 20
FEATURE                 Location/Qualifiers
source                  1..20
                        mol_type = other DNA
                        organism = synthetic construct
SEQUENCE: 22
aaaccacagg gcatactggg                                              20

SEQ ID NO: 23           moltype = DNA  length = 20
FEATURE                 Location/Qualifiers
source                  1..20
                        mol_type = other DNA
                        organism = synthetic construct
SEQUENCE: 23
gatatcccgg cgaacaaggt                                              20

SEQ ID NO: 24           moltype = DNA  length = 20
FEATURE                 Location/Qualifiers
source                  1..20
                        mol_type = other DNA
                        organism = synthetic construct
SEQUENCE: 24
tcctgcatgt cgtggatcag                                              20

SEQ ID NO: 25           moltype = DNA  length = 20
FEATURE                 Location/Qualifiers
source                  1..20
                        mol_type = other DNA
                        organism = synthetic construct
SEQUENCE: 25
cgacctctcc acgcagattt                                              20

SEQ ID NO: 26           moltype = DNA  length = 20
FEATURE                 Location/Qualifiers
source                  1..20
                        mol_type = other DNA
                        organism = synthetic construct
SEQUENCE: 26
cggtgcctga aaaactcgac                                              20

SEQ ID NO: 27           moltype = DNA  length = 20
FEATURE                 Location/Qualifiers
source                  1..20
                        mol_type = other DNA
                        organism = synthetic construct
SEQUENCE: 27
ccgaaagagc agagcgatga                                              20
```

-continued

```
SEQ ID NO: 28           moltype = DNA  length = 20
FEATURE                 Location/Qualifiers
source                  1..20
                        mol_type = other DNA
                        organism = synthetic construct
SEQUENCE: 28
ccagcacggt atcgtcttca                                          20

SEQ ID NO: 29           moltype = DNA  length = 20
FEATURE                 Location/Qualifiers
source                  1..20
                        mol_type = other DNA
                        organism = synthetic construct
SEQUENCE: 29
gggctcaatt ccgaccgtat                                          20

SEQ ID NO: 30           moltype = DNA  length = 20
FEATURE                 Location/Qualifiers
source                  1..20
                        mol_type = other DNA
                        organism = synthetic construct
SEQUENCE: 30
cgtcgggaac ggatagaagg                                          20
```